(12) United States Patent
Murphy et al.

(10) Patent No.: US 9,688,957 B2
(45) Date of Patent: *Jun. 27, 2017

(54) HYDROGEL COMPOSITIONS FOR USE IN PROMOTING TUBULOGENESIS

(71) Applicant: Wisconsin Alumni Research Foundation, Madison, WI (US)

(72) Inventors: William L. Murphy, Waunakee, WI (US); Ngoc Nhi Le, Norcross, GA (US); Michael P. Schwartz, Madison, WI (US); Eric Huy Dang Nguyen, Madison, WI (US); Stefan Zorn, Madison, WI (US); Hamisha Ardalani, Madison, WI (US); Matthew Zanotelli, Muskego, WI (US); Matthew Brian Parlato, Madison, WI (US); David Gregory Belair, Madison, WI (US); William T. Daly, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 14/684,062

(22) Filed: Apr. 10, 2015

(65) Prior Publication Data

US 2015/0291929 A1 Oct. 15, 2015

Related U.S. Application Data

(60) Provisional application No. 61/978,032, filed on Apr. 10, 2014.

(51) Int. Cl.
| | |
|---|---|
| *C12N 5/00* | (2006.01) |
| *C12N 5/0735* | (2010.01) |
| *G01N 33/483* | (2006.01) |
| *B01J 19/00* | (2006.01) |
| *G01N 21/64* | (2006.01) |

(52) U.S. Cl.
CPC ....... *C12N 5/0606* (2013.01); *G01N 33/4833* (2013.01); *B01J 19/0046* (2013.01); *B01J 2219/00596* (2013.01); *C12N 2533/20* (2013.01); *C12N 2533/30* (2013.01); *C12N 2537/10* (2013.01); *G01N 21/6452* (2013.01); *G01N 2610/00* (2013.01)

(58) Field of Classification Search
CPC .................................................. C12N 5/0606
See application file for complete search history.

(56) References Cited

U.S. PATENT DOCUMENTS

| | | |
|---|---|---|
| 2005/0019843 A1 | 1/2005 | Chen et al. |
| 2012/0149781 A1 | 6/2012 | Lee et al. |
| 2012/0225814 A1 | 9/2012 | Hanjaya-Putra et al. |
| 2013/0210147 A1 | 8/2013 | Jeannin et al. |
| 2013/0260464 A1 | 10/2013 | Vannier et al. |
| 2013/0296177 A1 | 11/2013 | Koepsel et al. |
| 2014/0017284 A1 | 1/2014 | Yang et al. |
| 2014/0018263 A1 | 1/2014 | Levkin et al. |
| 2015/0104812 A1 | 4/2015 | Grevesse et al. |

OTHER PUBLICATIONS

Shih et al. Biomacromolecules, 2012, 13:2003-2012.*
Kyburz et al., Three-dimensional hMSC motility within peptide-functionalized PEG-based hydrogels of varying adhesivity and crosslinking density, Acta Biomaterialia, vol. 9, No. 5, pp. 6381-6392, 2013.
Leslie-Barbick et al., The promotion of microvasculature formation in poly(ethylene glycol) diacrylate hydrogels by an immobilized VEGF-mimetic peptide, Biomaterials, vol. 32, No. 25, pp. 5782-5789, 2011.
Love et al., Self-Assembled Monolayers of Thiolates on Metals as a Form of Nanotechnology, Chem. Rev. 2005, 105:1103-1169.
Strolher et al., Synthesis and Characterization of DNA-Modified Silicon (III) Surfaces, J. Am. Chem. Soc. 2000, 122:1205-1209.
Schwartz et al., , Chemical modification of silicon surfaces for biological applications, 2005 Phys. Stat. Sol. (a) 202 (8):1380-1384.
Strother et al., Photochemical Functionalization of Diamond Films, Langmuir, 2002, 18:968-971.
Polizzotti et al., Three-Dimensional Biochemical Patterning of Click-Based Composit Hydrogels via Thiolene Photopolymerization, Biomacromolecules 2008, 9:1084-1087.
Fairbanks et al., A Versatile Synthetic Extracellular Matrix Mimic via Thiol-Norbornene Photopolymerization, Adv. Mater. 2009, 21:5005-5010.
Nagase and Fields, Human Matrix Metalloproteinase Specificity Studies Using Collagen Sequence-Based Synthetic Peptides, Biopolymers 1996, 40:399-416.
Toepke et al., Characterization of Thiol-Ene Crosslinked PEG Hydrogels, 2013, Macromol. Mater. Eng., 298:699-703.
Impellitteri et al., Specific VEGF sequestering and release using peptide-functionalized hydrogel microspheres, Biomaterials 2012, 33:3475-84.
Belair and Murphy, Specific VEGF sequestering to biomaterials: Influence of serum stability, Acta Biomater, 2013.
Gould et al., Small Peptide Functionalized Thiol-Ene Hydrogels as Culture Substrates for Understanding Valvular Interstitial Cell Activation and de novo Tissue Deposition, Acta Biomater 2012, 8:3201-3209.
Seo et al., Attachment of hydrogel microstructures and proteins to glass via thiol-terminated silanes, Colloids Surf B Biointerfaces 2012, 98:1-6.

(Continued)

*Primary Examiner* — Bin Shen
(74) *Attorney, Agent, or Firm* — Stinson Leonard Street LLC

(57) ABSTRACT

Hydrogel Compositions and methods of using hydrogel compositions are disclosed. Advantageously, the hydrogel compositions offer the ability to rapidly screen substrate components for influencing cell attachment, spreading, proliferation, migration, and differentiation. In particularly suitable embodiments, the hydrogel compositions of the present disclosure may be used to promote tubulogenesis of endothelial cells.

19 Claims, 52 Drawing Sheets
(19 of 52 Drawing Sheet(s) Filed in Color)

(56) References Cited

OTHER PUBLICATIONS

Halliwell et al., A Factorial Analysis of Silanization Conditions for the Immobilization of Oligonucletotides on Glass Surfaces, Anal Chem 2001, 73:2476-2483.

Cras et al., Comparison of chemical cleaning methods of glass in preparation for silanization, Biosens Bioelectron 1999, 14:683-688.

Vistas et al., Silanization of glass chips—A factorial approach for optimization, Appl Surf Sci 2013, 286:314-318.

Jo et al., Three-Dimensional Micro-Channel Fabrication in Polydimethylsiloxane (PDMS) Elastomer, 2000 J Microelectromechanical Syst. 9:76-81.

Prime and Whitesides, Adsorption of Proteins onto Surfaces Containing End-Attached Oligo(ethylene oxide): A Model System Using Self-Assembled Monolayers, 1993 J. Am. Chem. Soc. 115:10714-10721.

Engler et al., Matrix Elasticity Directs Stem Cell Lineage Specification, Cell 126:677 (2006).

Nguyen et al. "Differential effects of cell adhesion, modulus and VEGFR-2 inhibition on capillary network formation in synthetic hydrogel arrays," Biomaterials, 35, 2014, pp. 2149-2161.

Hansen et al., "Biomaterial arrays with defined adhesion ligand densities and matrix stiffness identify distinct phenotypes for tumorigenic and non-tumorigenic human mesenchymal cell types," Biomaterials Science, Royal Society of Chemistry, Published Jan. 22, 2014, 12 pages.

Raza, Asad et al., 'The influence of matrix degradation and functionality on cell survival and morphogenesis in PEG-based hydrogels', Macromolecular Bioscience, 2013, vol. 13, No. 8, pp. 1048-1058.

Banerjee, Akhilesh et al., 'The influence of hydrogel modulus on the proliferation and differentiation of encapsulated neural stem cells', Biomaterials, 2009, vol. 30, No. 27, pp. 4695-4699.

Hern et al., Incorporation of adhesion peptides into nonadhesive hydrogels useful for tissue resurfacing, Journal of Biomed Mater Res, 1998, vol. 39, No. 2, pp. 266-276.

Liu, et al., Covalently immobilized biomolecule gradient on hydrogel surface using a gradient generating microfluidic device for a quantitative mesenchymal stem cell study, Biomicrofluidics 6, 024111, 2012.

Pishko, Michael V., Microfabricated Cell-based biosensor Arrays, Engineering in Medicine and Biology 27th Annual Conference, Shanghai, China, Sep. 1-4, 2005.

Porter et al., Covalently grafted VEGF 165 in Hydrogel models upregulates the cellular pathways associated with angiogenesis, Am J. Physiol Cell Physiol, vol. 301, pp. C1086-C1092, 2011.

\* cited by examiner

EGM2 Growth Medium

SU5416 Supplemented Medium

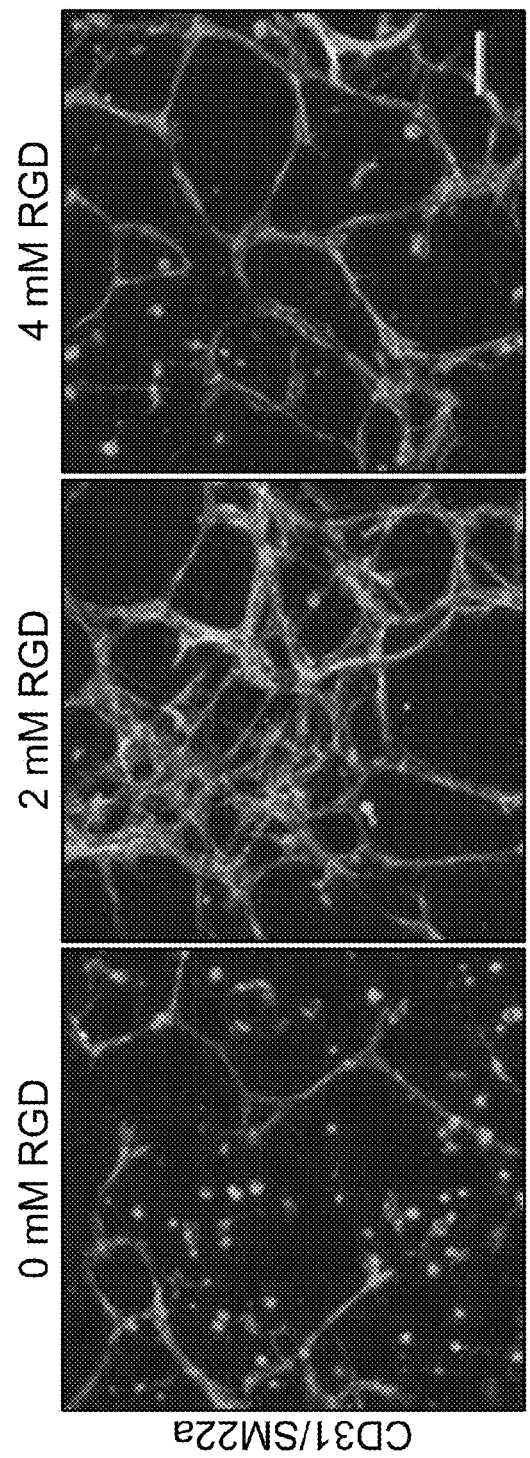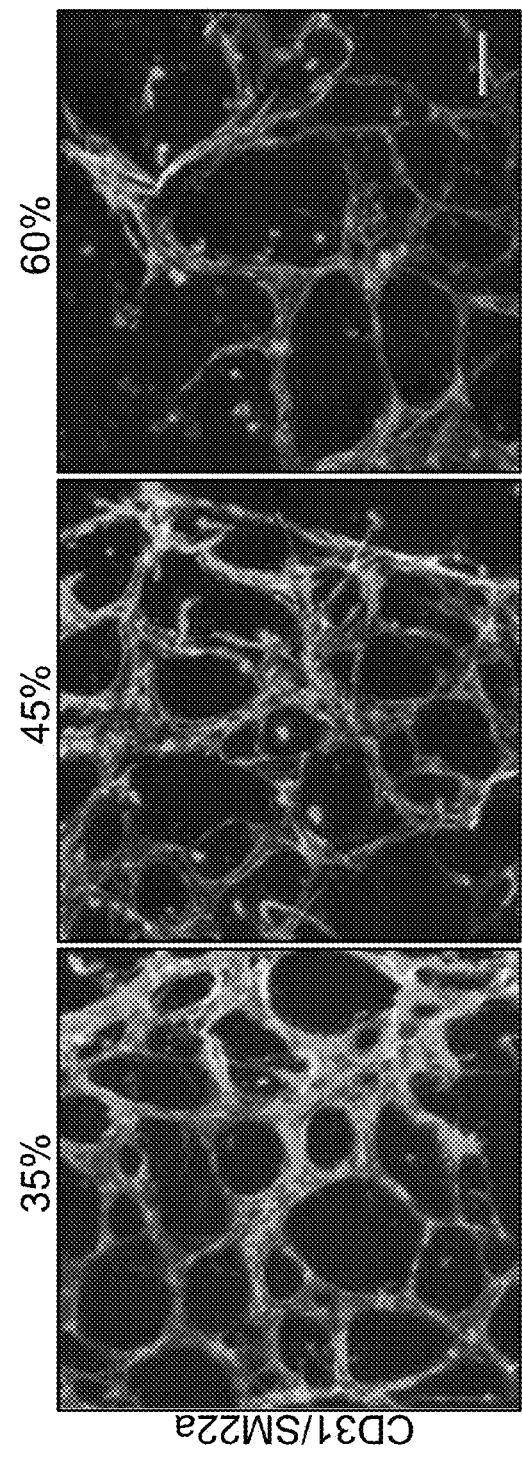
FIG. 23A
FIG. 23B 0.25 mM cycRGD, 0 mM VBP
Stable tubule networks at 24 hours 0.25 mM cycRGD, 0.3 mM VBP
Stable tubule networks at 24 hours 0.25 mM cycRGD-Stable tubule
networks at 24 hours Unstable networks,
inhibited with Sunitinib 0.25 mM cycRGD, No VBP or
scrambled VBP Stable
tubule networks at 24 hours 0.25 mM cycRGD, 0No VBP or
scrambled VBP Stable tubule
networks at 48 hours

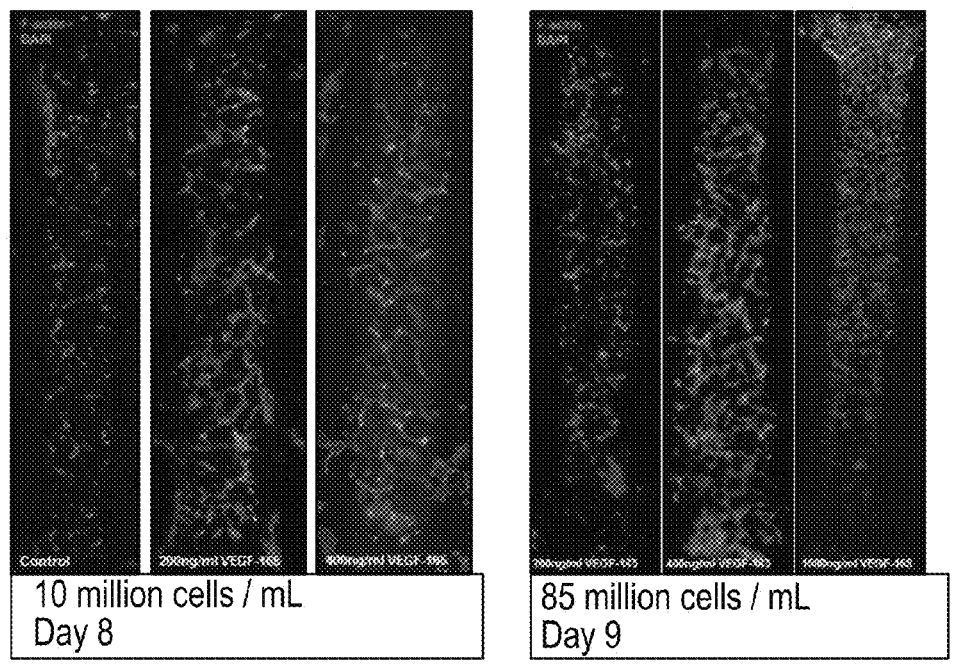
FIG. 31A   FIG. 31B
FIG. 32A
FIG. 32B
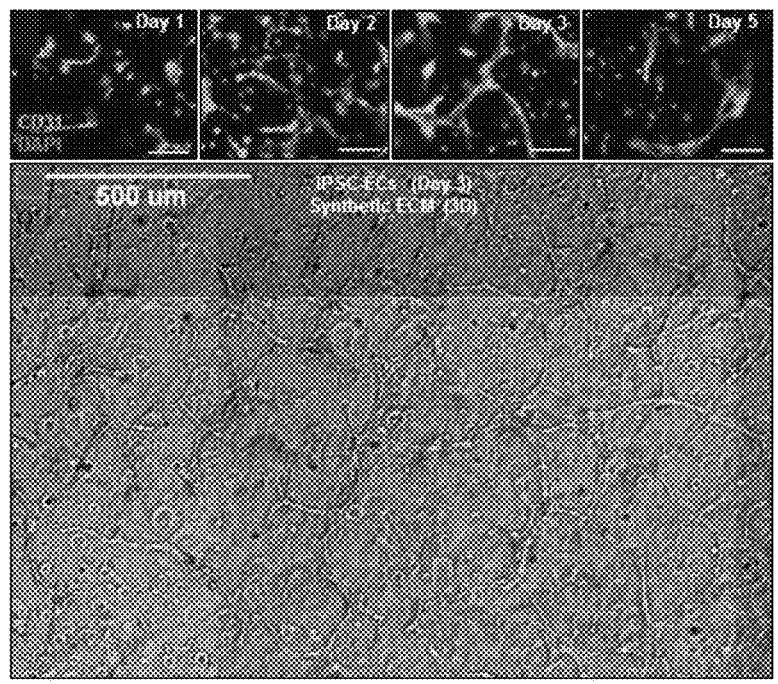

SEQUENCE LISTING

```
<160> NUMBER OF SEQ ID NOS: 47

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Arg Gly Asp Ser
1

<210> SEQ ID NO 2
<211> LENGTH: 5
<212> TYPE: PRT
<213> ORGANISM: Artificial Sequence
```

```
<220> FEATURE:
<223> OTHER INFORMATION: Synthetic

<400> SEQUENCE: 2

Cys Arg Gly Asp Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Gly Arg Gly Asp Ser Pro
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

Pro His Ser Arg Asn
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Gly Trp Gly Gly Arg Gly Asp Ser Pro
1               5

<210> SEQ ID NO 6
<211> LENGTH: 13
<212> TYPE: PRT
<213> ORGANISM: Artificial Sequence
<220> FEATURE:
<223> OTHER INFORMATION: Synthetic

<400> SEQUENCE: 6

Ser Ile Asp Gln Val Glu Pro Tyr Ser Ser Thr Ala Gln
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic

<400> SEQUENCE: 7

Gly Arg Asn Ile Ala Glu Ile Ile Lys Asp Ile
1               5                   10

<210> SEQ ID NO 8
<211> LENGTH: 9
<212> TYPE: PRT
<213> ORGANISM: Artificial Sequence
<220> FEATURE:
```

```
<223> OTHER INFORMATION: Synthetic

<400> SEQUENCE: 8

Asp Ile Thr Tyr Val Arg Leu Lys Phe
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Asp Ile Thr Val Thr Leu Asn Arg Leu
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Gly Arg Tyr Val Val Leu Pro Arg
1               5

<210> SEQ ID NO 11
<211> LENGTH: 13
<212> TYPE: PRT
<213> ORGANISM: Artificial Sequence
<220> FEATURE:
<223> OTHER INFORMATION: Synthetic

<400> SEQUENCE: 11

Gly Asn Arg Trp His Ser Ile Tyr Ile Thr Arg Phe Gly
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

Gly Ala Ser Ile Lys Val Ala Val Ser Ala Asp Arg
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Gly Thr Thr Val Lys Tyr Ile Phe Arg
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic
```

<400> SEQUENCE: 14

Gly Ser Ile Lys Ile Arg Gly Thr Tyr Ser
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

Gly Ser Ile Asn Asn Asn Arg
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Ser Asp Pro Gly Tyr Ile Gly Ser Arg
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic

<400> SEQUENCE: 17

Tyr Ile Gly Ser Arg
1               5

<210> SEQ ID NO 18
<211> LENGTH: 14
<212> TYPE: PRT
<213> ORGANISM: Artificial Sequence
<220> FEATURE:
<223> OTHER INFORMATION: Synthetic

<400> SEQUENCE: 18

Gly Thr Pro Gly Pro Gln Gly Ile Ala Gly Gln Gly Val Val
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Synthetic

<400> SEQUENCE: 19

Gly Thr Pro Gly Pro Gln Gly Ile Ala Gly Gln Arg Val Val
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Synthetic

```
<400> SEQUENCE: 20

Met Asn Tyr Tyr Ser Asn Ser
1               5

<210> SEQ ID NO 21
<211> LENGTH: 12
<212> TYPE: PRT
<213> ORGANISM: Artificial Sequence
<220> FEATURE:
<223> OTHER INFORMATION: Synthetic

<400> SEQUENCE: 21

Lys Lys Gln Arg Phe Arg His Arg Asn Arg Lys Gly
1               5                   10

<210> SEQ ID NO 22
<211> LENGTH: 18
<212> TYPE: PRT
<213> ORGANISM: Artificial Sequence
<220> FEATURE:
<223> OTHER INFORMATION: Synthetic

<400> SEQUENCE: 22

Gly Gly Gly Lys Leu Thr Trp Gln Glu Leu Tyr Gln Leu Lys Tyr Lys
1               5                   10                  15

Gly Ile

<210> SEQ ID NO 23
<211> LENGTH: 15
<212> TYPE: PRT
<213> ORGANISM: Artificial Sequence
<220> FEATURE:
<223> OTHER INFORMATION: Synthetic

<400> SEQUENCE: 23

Lys Leu Thr Trp Gln Glu Leu Tyr Gln Leu Lys Tyr Lys Gly Ile
1               5                   10                  15

<210> SEQ ID NO 24
<211> LENGTH: 12
<212> TYPE: PRT
<213> ORGANISM: Artificial Sequence
<220> FEATURE:
<223> OTHER INFORMATION: Synthetic

<400> SEQUENCE: 24

Lys Ile Pro Lys Ala Ser Ser Val Pro Thr Glu Leu
1               5                   10

<210> SEQ ID NO 25
<211> LENGTH: 20
<212> TYPE: PRT
<213> ORGANISM: Artificial Sequence
<220> FEATURE:
<223> OTHER INFORMATION: Synthetic

<400> SEQUENCE: 25

Lys Ile Pro Lys Ala Ser Ser Val Pro Thr Glu Leu Ser Ala Ile Ser
1               5                   10                  15

Thr Leu Tyr Leu
            20
```

```
<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Lys Arg Thr Gly Gln Tyr Lys Leu
1               5

<210> SEQ ID NO 27
<211> LENGTH: 14
<212> TYPE: PRT
<213> ORGANISM: Artificial Sequence
<220> FEATURE:
<223> OTHER INFORMATION: Synthetic

<400> SEQUENCE: 27

Lys Cys Gly Gly Pro Gln Gly Ile Trp Gly Gln Gly Cys Lys
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetic

<400> SEQUENCE: 28

Lys Cys Gly Gly Pro Gln Gly Ile Ala Gly Gln Gly Cys Lys
1               5                   10

<210> SEQ ID NO 29
<211> LENGTH: 22
<212> TYPE: PRT
<213> ORGANISM: Artificial Sequence
<220> FEATURE:
<223> OTHER INFORMATION: Synthetic

<400> SEQUENCE: 29

Cys Arg Gly Asp Gly Gly Gly Gly Gly Gly Gly Gly Gly Gly
1               5                   10                  15

Gly Pro His Ser Arg Asn
            20

<210> SEQ ID NO 30
<211> LENGTH: 19
<212> TYPE: PRT
<213> ORGANISM: Artificial Sequence
<220> FEATURE:
<223> OTHER INFORMATION: Synthetic

<400> SEQUENCE: 30

Cys Pro His Ser Arg Asn Ser Gly Ser Gly Ser Gly Ser Gly
1               5                   10                  15

Arg Gly Asp

<210> SEQ ID NO 31
<211> LENGTH: 10
<212> TYPE: PRT
<213> ORGANISM: Artificial Sequence
<220> FEATURE:
<223> OTHER INFORMATION: Synthetic
```

```
<400> SEQUENCE: 31

Gly Cys Tyr Gly Arg Gly Asp Ser Pro Gly
1               5                   10

<210> SEQ ID NO 32
<211> LENGTH: 5
<212> TYPE: PRT
<213> ORGANISM: Artificial Sequence
<220> FEATURE:
<223> OTHER INFORMATION: Synthetic

<400> SEQUENCE: 32

Cys Arg Asp Gly Ser
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: D-phenylalanine

<400> SEQUENCE: 33

Arg Gly Asp Phe Cys
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Arg Gly Asp Pro His Ser Arg Asn
1               5

<210> SEQ ID NO 35
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-phenylalanine
<220> FEATURE:
<221> NAME/KEY: MISC_FEATURE
<222> LOCATION: (4)..(4)
<223> OTHER INFORMATION: D-alanine
<220> FEATURE:
<221> NAME/KEY: MISC_FEATURE
<222> LOCATION: (5)..(5)
<223> OTHER INFORMATION: D-tyrosine
<220> FEATURE:
<221> NAME/KEY: MISC_FEATURE
<222> LOCATION: (6)..(6)
<223> OTHER INFORMATION: D-leucine

<400> SEQUENCE: 35

Cys Glu Phe Ala Tyr Leu Ile Asp Phe Asn Trp Glu Tyr Pro Ala Ser
1               5                   10                  15

Lys
```

```
<210> SEQ ID NO 36
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-alanine
<220> FEATURE:
<221> NAME/KEY: MISC_FEATURE
<222> LOCATION: (7)..(7)
<223> OTHER INFORMATION: D-phenylalanine
<220> FEATURE:
<221> NAME/KEY: MISC_FEATURE
<222> LOCATION: (13)..(13)
<223> OTHER INFORMATION: D-tyrosine
<220> FEATURE:
<221> NAME/KEY: MISC_FEATURE
<222> LOCATION: (17)..(17)
<223> OTHER INFORMATION: D-leucine

<400> SEQUENCE: 36

Cys Asp Ala Pro Tyr Asn Phe Glu Phe Ala Trp Glu Tyr Val Ile Ser
1               5                   10                  15

Leu Lys

<210> SEQ ID NO 37
<211> LENGTH: 12
<212> TYPE: PRT
<213> ORGANISM: Artificial Sequence
<220> FEATURE:
<223> OTHER INFORMATION: Synthetic

<400> SEQUENCE: 37

Arg Lys Arg Leu Gln Val Gln Leu Ser Ile Arg Thr
1               5                   10

<210> SEQ ID NO 38
<211> LENGTH: 5
<212> TYPE: PRT
<213> ORGANISM: Artificial Sequence
<220> FEATURE:
<223> OTHER INFORMATION: Synthetic

<400> SEQUENCE: 38

Ile Lys Val Ala Val
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic

<400> SEQUENCE: 39

Tyr Ile Gly Ser Arg
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40
```

```
Lys Arg Thr Gly Gln Tyr Lys Leu
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic

<400> SEQUENCE: 41

Thr Tyr Arg Ser Arg Lys Tyr
1               5

<210> SEQ ID NO 42
<211> LENGTH: 17
<212> TYPE: PRT
<213> ORGANISM: Artificial Sequence
<220> FEATURE:
<223> OTHER INFORMATION: Synthetic

<400> SEQUENCE: 42

Lys Arg Thr Gly Gln Tyr Lys Leu Gly Ser Lys Thr Gly Pro Gly Gln
1               5                   10                  15

Lys

<210> SEQ ID NO 43
<211> LENGTH: 14
<212> TYPE: PRT
<213> ORGANISM: Artificial Sequence
<220> FEATURE:
<223> OTHER INFORMATION: Synthetic

<400> SEQUENCE: 43

Gln Ala Lys His Lys Gln Arg Lys Arg Leu Lys Ser Ser Cys
1               5                   10

<210> SEQ ID NO 44
<211> LENGTH: 17
<212> TYPE: PRT
<213> ORGANISM: Artificial Sequence
<220> FEATURE:
<223> OTHER INFORMATION: Synthetic

<400> SEQUENCE: 44

Ser Pro Lys His His Ser Gln Arg Ala Arg Lys Lys Asn Lys Asn
1               5                   10                  15

Cys

<210> SEQ ID NO 45
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is a hydropathic residue
<220> FEATURE:
<221> NAME/KEY: MISC_FEATURE
<222> LOCATION: (2)..(2)
<223> OTHER INFORMATION: B is a basic residue
<220> FEATURE:
<221> NAME/KEY: MISC_FEATURE
<222> LOCATION: (3)..(3)
<223> OTHER INFORMATION: B is a basic residue
```

```
<220> FEATURE:
<221> NAME/KEY: MISC_FEATURE
<222> LOCATION: (4)..(4)
<223> OTHER INFORMATION: X is a hydropathic residue
<220> FEATURE:
<221> NAME/KEY: MISC_FEATURE
<222> LOCATION: (5)..(5)
<223> OTHER INFORMATION: B is a basic residue
<220> FEATURE:
<221> NAME/KEY: MISC_FEATURE
<222> LOCATION: (6)..(6)
<223> OTHER INFORMATION: X is a hydropathic residue

<400> SEQUENCE: 45

Xaa Asx Asx Xaa Asx Xaa
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is a hydropathic residue
<220> FEATURE:
<221> NAME/KEY: MISC_FEATURE
<222> LOCATION: (2)..(2)
<223> OTHER INFORMATION: B is a basic residue
<220> FEATURE:
<221> NAME/KEY: MISC_FEATURE
<222> LOCATION: (3)..(3)
<223> OTHER INFORMATION: B is a basic residue
<220> FEATURE:
<221> NAME/KEY: MISC_FEATURE
<222> LOCATION: (4)..(4)
<223> OTHER INFORMATION: B is a basic residue
<220> FEATURE:
<221> NAME/KEY: MISC_FEATURE
<222> LOCATION: (5)..(5)
<223> OTHER INFORMATION: X is a hydropathic residue
<220> FEATURE:
<221> NAME/KEY: MISC_FEATURE
<222> LOCATION: (6)..(6)
<223> OTHER INFORMATION: X is a hydropathic residue
<220> FEATURE:
<221> NAME/KEY: MISC_FEATURE
<222> LOCATION: (7)..(7)
<223> OTHER INFORMATION: B is a basic residue
<220> FEATURE:
<221> NAME/KEY: MISC_FEATURE
<222> LOCATION: (8)..(8)
<223> OTHER INFORMATION: X is a hydropathic residue

<400> SEQUENCE: 46

Xaa Asx Asx Asx Xaa Xaa Asx Xaa
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic

<400> SEQUENCE: 47

Arg Gly Asp Ser Pro
1               5
```

HYDROGEL COMPOSITIONS FOR USE IN PROMOTING TUBULOGENESIS

CROSS-REFERENCE TO RELATED APPLICATION

This application claims priority to U.S. Provisional Patent Application No. 61/978,032, filed on Apr. 10, 2014, which is incorporated by reference herein in its entirety.

STATEMENT REGARDING FEDERALLY SPONSORED RESEARCH OR DEVELOPMENT

This invention was made with government support under HL093282 awarded by the National Institutes of Health. The government has certain rights in the invention.

STATEMENT IN SUPPORT FOR FILING A SEQUENCE LISTING

A paper copy of the Sequence Listing and a computer readable form of the Sequence Listing containing the file named "P140314US02_ST25.txt", which is 11,539 bytes in size (as measured in MICROSOFT WINDOWS® EXPLORER), are provided herein and are herein incorporated by reference. This Sequence Listing consists of SEQ ID NOs:1-47.

BACKGROUND OF THE DISCLOSURE

The present disclosure relates generally to methods for preparing biomaterial compositions and methods for using the biomaterial compositions. More particularly, the present disclosure relates to hydrogel compositions, and particularly hydrogel arrays, methods for screening cell substrate interactions using the hydrogel compositions, and methods for promoting tubulogenesis using the hydrogel compositions.

The development of most tissue types involves a complex interplay of multiple signals leading to controlled precursor cell differentiation into mature, tissue-specific cell types. For example, mesenchymal stem cells (MSCs) may be differentiated in vitro into osteoblasts, chondrocytes, myoblasts, adipocytes, neurons, and endothelial cells by exposure to a variety of growth factors. Exposure to growth factors may be controlled by the media and the substrates upon which the cells are cultured. Substantial progress has been made in the development of defined media, but only more recently has the role of substrates and cell-substrate adhesion on cell growth been examined.

Based on studies to determine defined media, it has become apparent that the substrate is important for successful cellular growth and tissue generation. For example, it has been demonstrated that attachment to the substrate by human embryonic stem cells may contribute to the variability in whether the cells remain undifferentiated or undergo differentiation. Therefore, it is important to not only identify cell culture media for successful cell culture conditions, but to also identify defined substrates.

Screening well-defined surfaces in an array format allows rapid identification of specific molecules that promote cellular adhesion, cellular spreading, proliferation, migration and differentiation, as well as molecules that regulate cell behavior. Biomaterial arrays such as self-assembled monolayers ("SAMs") in array formats (i.e., SAM arrays) have been constructed that present ligands to cells plated onto the array. A SAM is an organized layer of amphiphilic molecules in which one end of the molecule exhibits a specific, reversible affinity for a substrate and the other end of the molecule has a functional group. Because the molecule used to form the SAM array is polarized, the hydrophilic "head groups" assemble together on the substrate, while the hydrophobic tail groups assemble far from the substrate. Areas of close-packed molecules nucleate and grow until the surface of the substrate is covered in a single monolayer.

The use of alkanethiols to construct SAM arrays allow for the formation of reproducible SAM arrays and surfaces. SAM arrays may be used to identify specific ligands or epitopes that promote cellular attachment, spreading, proliferation, migration and differentiation. Additionally, SAM arrays may be patterned such that ligands will be presented to the cells in defined areas of the array.

While biomaterial arrays such as SAM arrays provide an excellent model substrate for investigating the effects of an immobilized ligand on cell behavior, preparing SAM array platforms using less labor intensive processes are needed to make SAM array use more widespread. Accordingly, there exists a need for alternative methods for preparing patterned biomaterial arrays to identify surfaces that will support survival and growth of cells in culture, allow rapid identification of specific molecules that promote cellular adhesion, cellular spreading, proliferation, migration, differentiation and regulate cellular behavior.

BRIEF DESCRIPTION OF THE DISCLOSURE

The present disclosure relates generally to biomaterial compositions and methods for using the biomaterial compositions. More particularly, the present disclosure relates to hydrogel compositions, methods for screening cell substrate interactions using the hydrogel compositions, and methods for promoting tubulogenesis using the hydrogel compositions.

In accordance with the present disclosure, methods for preparing hydrogel compositions support survival and growth of cells in culture, allow rapid identification of specific molecules that promote cellular adhesion, cellular spreading, proliferation, migration, differentiation and regulate cellular behavior have been discovered. The hydrogel compositions of the present disclosure can also be used for two-dimensional (2D) and three-dimensional (3D) cell culture. The hydrogel compositions of the present disclosure can further be used for two-dimensional and three-dimensional enrichment of biomolecules such as, for example, biomolecules to cell surfaces using soluble factor binders. The hydrogel compositions of the present disclosure can also be used as sources for soluble factors by encapsulating cells and soluble-factor releasing microparticles, which can be used to promote angiogenesis, promote tubulogenesis, promote morphogenic processes and screening for drug toxicity, for example. Additionally, the hydrogel compositions of the present disclosure can be used to analyze molecule-molecule interactions such as, for example, ligand-target interactions, antibody-antigen interactions, protein-protein interactions, growth factor-binding ligand interactions, receptor-ligand interactions and the like. Use of the hydrogel compositions of the present disclosure to analyze molecule-molecule interactions can allow for determining specificity of binding, affinity of binding and the like.

In one aspect, the present disclosure is directed to a method of screening for pro-tubulogenic agents and anti-tubulogenic agents. The method includes preparing a hydrogel composition, wherein the hydrogel composition includes a polyethylene glycol functionalized with norbornene, a crosslinking peptide, a cell adhesion peptide, and a soluble factor binder; providing an agent suspected of promoting or reducing tubulogenesis; contacting a cell with the hydrogel composition and agent; and analyzing the cell.

In another aspect, the present disclosure is directed to a method of promoting tubulogenesis. The method includes preparing a hydrogel composition, wherein the hydrogel composition includes a polyethylene glycol functionalized with norbornene, a crosslinking peptide, a cell adhesion peptide, and a soluble factor binder; providing a culture media in contact with the hydrogel composition; contacting a cell in the culture media in contact with the hydrogel composition; and analyzing the cell.

In yet another aspect, the present disclosure is directed to a hydrogel composition including a polyethylene glycol functionalized with norbornene, a crosslinking peptide, a cell adhesion peptide, and a soluble factor binder.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein:

FIG. 13A depicts hydrogels composed of (i) 8-arm PEG molecules, with each arm functionalized with a norbornene molecule; (ii) di-thiolated PEG crosslinking molecules bridge multiple 8-arm PEG molecules together into an ordered polymer network. A di-thiolated PEG molecule acts as an inert crosslinking molecule that is not cell-degradable; (iii) in bioactive hydrogels, PEG molecules are decorated with CRGDS (SEQ ID NO:2) adhesion peptide or CRDGS (SEQ ID NO:32) scrambled peptide to modulate cell adhesion to the hydrogel; (iv) di-thiolated MMP labile crosslinking peptides enable cell-driven hydrogel degradation. FIG. 13B depicts "background" hydrogels are void of cell adhesion molecules and are not subject to cell-driven degradation. FIG. 13C depicts "hydrogel spots" that modulate cell behavior through covalently attached adhesion molecules and are biodegradable via MMP activity.

FIG. 15A depicts equilibrium swelling ratios of degradable (left) and background (right) and hydrogels used in low, medium and high hydrogel modulus conditions. FIG. 15B depicts complex shear modulus of degradable (left) and background (right) hydrogels used in low, medium and high hydrogel modulus conditions. Error bars indicate standard deviation. FIG. 15C depicts reduction in norbornene alkene protons due to covalent coupling of CRGDS (SEQ ID NO:2) adhesion peptide and CRDGS (SEQ ID NO:32) scrambled peptide as measured using NMR. FIG. 15D depicts N-terminal amines of CRGDS (SEQ ID NO:2) adhesion peptide labeled with Alexa Fluor® 488 (Green). Green fluorescence intensity was quantified from the left to right columns (black lines: PEG polymer and crosslinker; red circles: CRGDS).

FIG. 16A depicts cell viability as determined by counting live cell and dead cell nuclei 48 hours after encapsulation. FIG. 16B depicts cell viability measured when VEGFR2 was inhibited by 10 µM SU5416 supplementation, *, p<0.05, &, p<0.05 compared to all equivalent CRGDS (SEQ ID NO:2) adhesion peptide concentrations in other modulus conditions. FIG. 16C depicts viability of SU5416-treated HUVECs normalized to HUVEC viability in growth medium, *, p<0.05; , p<0.01; *, p<0.001 compared to growth medium control.

FIG. 17A depicts cell proliferation as determined by Click-it EdU staining 24 hours after encapsulation. FIG. 17B depicts cell proliferation measured when VEGFR2 was inhibited by 10 µM SU5416 supplementation, *, p<0.05, &, p<0.05 compared to all equivalent CRGDS (SEQ ID NO:2) adhesion peptide concentrations in other modulus conditions. FIG. 17C depicts cell proliferation during SU5416 treatment normalized to proliferation in growth medium, *, p<0.05; , p<0.01; *, p<0.001 compared to growth medium control. FIG. 17D depicts proliferating cells (arrowheads) that were localized to multicellular structures (green: cell tracker green; blue: Hoechst nuclear stain; red: Alexa Fluor® 594 labeling nuclei of cells in S-phase).

FIG. 18A depicts total tubule length as determined by manually measuring tubule lengths throughout the spots from epifluorescence Z-stack images. The cells were stained using Cell Tracker Green and Hoechst nuclear stain 24 hours after encapsulation. FIG. 18B depicts tubulogenesis when VEGFR2 was inhibited by 10 µM SU5416 supplementation, *, p<0.05, &, p<0.05 compared to all equivalent CRGDS (SEQ ID NO:2) adhesion peptide concentrations in other modulus conditions. FIG. 18C depicts tubulogenesis during SU5416 treatment normalized to tubulogenesis in growth medium, *, p<0.05; , p<0.01; *, p<0.001 compared to growth medium control. FIG. 18D depicts confocal microscopy images of low tubulogenesis in low moduli, 2 µM RGDS adhesion peptide spots and increased tubulogenesis levels with SU5416 treatment. Bottom: enlarged examples of capillary-like structures seen in the VEGFR2-inhibited condition. Scale bars: 100 µm. Green: Cell Tracker Green; Blue: Hoechst nuclear stain.

FIG. 19A depicts HUVEC proliferation with and without SU5416 supplementation on tissue culture-treated polystyrene (TCPS), *, p<0.05. FIG. 19B depicts HUVEC tubulogenesis with and without SU5416 supplementation in growth factor-reduced MATRIGEL®. FIGS. 19C & 19D depict HUVEC CLS formation in 0.4 µL MATRIGEL® spots. In each pair of pictures, the tubules in the right hand copy were highlighted. Green: Cell Tracker Green, *, p<0.05 between EGM2 and SU5416-treated conditions.

FIG. 20A depicts HUVEC tubulogenesis in a hydrogel that is secured to the bottom of a 48-well plate using a second stabilizing hydrogel that does not contain RGD and was non-degradable. FIG. 20B depicts HUVEC tubulogenesis in a similar hydrogel that was freely floating in growth media containing 10 µM SU5416 inside a 24-well plate.

FIGS. 23A-E depict the resulting extent of network formation, adhesion, crosslinking density, and stability of the vascular structures when matrix properties, crosslinking density, culture media, and presence of support cells were varied as analyzed in Example 5.

FIGS. 27A & 27B depict photographs of HUVECs forming tubule networks on hydrogel surfaces presenting cyclic RGD adhesion peptide as well as functional and scrambled VEGF-binding peptides. FIG. 27C depicts photographs of a HUVEC tubule network on a hydrogel surface presenting cyclic RGD adhesion peptide only at 24 and 48 hours post-seeding.

FIGS. 31A & 31B depict a series of photographs of iPS-ECs maintaining 3D tubule networks in PEG hydrogels 8 and 9 days post-encapsulation after treatment with various concentrations of VEGF as well as an example of failed network maintenance as analyzed in Example 11.

FIGS. 32A & 32B depict a series of photographs of iPS-ECs forming 3D tubule networks in PEG hydrogels 1, 2, 3 and 5 days post-encapsulation as analyzed in Example 12.

Figure 1A:
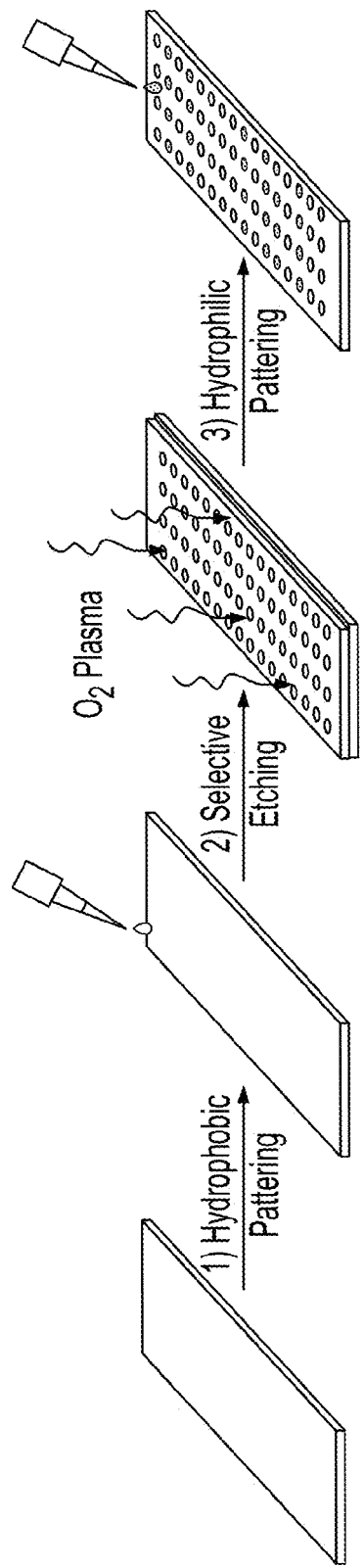
FIGS. 1A-1B are schematic illustrations of the steps for preparing a hydrogel array of the present disclosure.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure, methods for preparing biomaterial compositions for screening molecule-molecule interactions and promoting tubulogenesis have been discovered. More particularly, the present disclosure relates to hydrogel compositions. In one aspect, hydrogel compositions can be prepared as a hydrogel array with individually controlled hydrogel spot modulus, hydrogel spot polymer density, hydrogel spot ligand identity and hydrogel spot ligand density and to methods for preparing the hydrogel arrays. In another aspect, the hydrogel compositions can be prepared as coatings such as for use on the surfaces of cell culture plates. In yet another aspect, the hydrogel compositions can be prepared as microcarriers in suspension culture. The hydrogel compositions of the present disclosure can be functionalized with biomolecules, are compatible with cell culture and are biocompatible. The hydrogel compositions, of the present disclosure, can also be used to alter (e.g., enhance, inhibit and change) cell function. Hydrogel compositions can also be prepared to include regions that are surrounded by hydrogel to form regions that are absent (or devoid) of hydrogel.

As known by those skilled in the art, a hydrogel composition is a network of polymer chains that are hydrophilic in which a polymeric material and water are in an equilibrated form. The hydrogel composition is formed using unpolymerized starting components. The polymeric material can be, for example, a natural polymer material, a synthetic polymer material and combinations thereof.

The methods for preparing hydrogel compositions of the present disclosure advantageously allows for the direct incorporation of peptides into the hydrogel network during polymerization by including a cysteine in the amino acid sequence during synthesis, which allows for eliminating the need for post-synthetic modifications. In this way, peptides can be utilized as crosslinkers by including cysteine on each end or they can be incorporated as pendant groups, which can be precoupled to the polymer backbone and mixed in varying combinations or incorporated during polymerization for simplicity.

Hydrogel Compositions and Methods for Preparing Hydrogel Compositions

The present disclosure is generally directed to methods for preparing a hydrogel composition and use of the resulting compositions. When used to prepare a hydrogel array, the preparation methods generally include contacting a hydrogel precursor solution with a substrate, wherein the substrate includes a hydrophobic region and a hydrophilic region; placing a surface-modified substrate onto the hydrogel precursor solution such that the hydrogel precursor solution is located between the substrate and the surface-modified substrate; polymerizing the hydrogel precursor solution; and separating the surface-modified substrate from the substrate, to result in the hydrogel array. (See, FIGS. 1A-1B). Thus, the polymer hydrogel precursor solution polymerizes between the substrate and the surface-modified substrate and the resultant hydrogel transfers with the surface-modified substrate such that the surface-modified substrate includes the hydrogel array. In one embodiment, the hydrogel array can be patterned to include an array of hydrogel spots surrounded by a hydrogel-free background as described in more detail below. In another embodiment, the hydrogel array can be patterned such that an array of hydrogel-free spots (or pools) is formed within a hydrogel background as described in more detail below.

Figure 5:
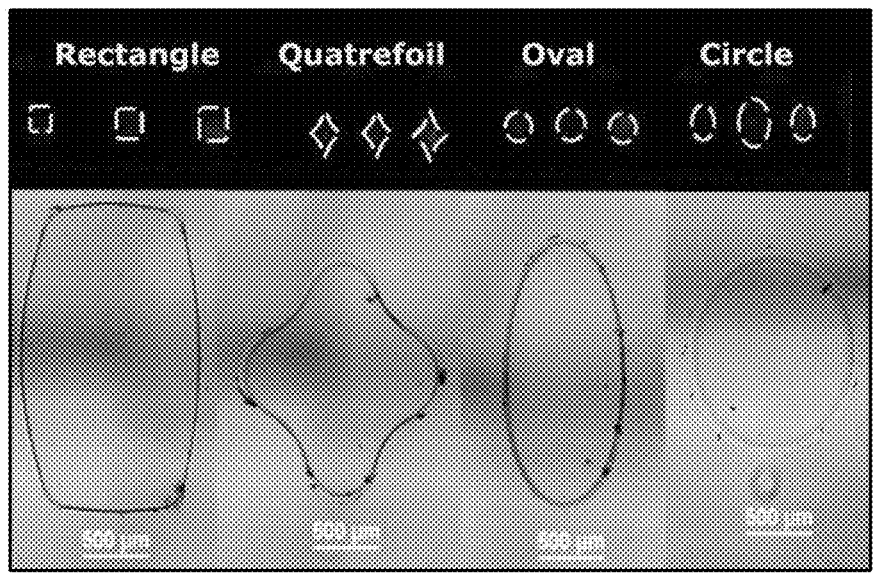
FIG. 5 illustrates high magnification top-view images showing different shapes of individual hydrogel spots.

In hydrogel arrays having hydrogel spots, the resultant hydrogel array can be patterned to result in differential wettability to define the geometry of each hydrogel spot and confine the contents of each hydrogel spot of the array, as well as define the spatial pattern of each hydrogel spot in the array in relation to neighboring spots. This is particularly useful for preparing hydrogel arrays for use with common microarray add-ons of different sizes and dimensions consistent with those of common multi-well plates (e.g., 96 well plates, 384 well plates, etc.) This is also useful for use with multichannel pipettes for enhanced-throughput cell culture, media exchange, and the like. The individual hydrogel spots of the array can have any desired shape (see e.g., FIG. 5). For example, the shape can be circular, round, oval, quatrefoil, rectangular, triangular, star-shaped, diamond-shaped, combinations thereof, and the like. Patterns of hydrogel spots may also be created in rows, spirals, circles, squares, rectangles, combinations thereof, and the like. The shape of the individual hydrogel spot can be varied by changing the pattern of the stencil used for etching during patterning of the patterned substrate.

In hydrogel arrays having hydrogel-free spots, the individual hydrogel-free spots can have any desired shape. For example, the shape can be circular, round, oval, quatrefoil, rectangular, triangular, star-shaped, diamond-shaped, combinations thereof, and the like. Patterns of hydrogel-free spots may also be created in rows, spirals, circles, squares, rectangles, combinations thereof, and the like. The shape of the individual hydrogel-free spot can be varied by changing the pattern of the stencil used for etching during patterning of the patterned substrate.

The upper size limit of the hydrogel array depends on the dimensions of the patterned substrate and/or the dimensions of the surface-modified substrate. The resultant hydrogel array can also be patterned to result in individual hydrogel spots and hydrogel-free spots having any desired sizes. The size and shape of the individual hydrogel spot and hydrogel-free spot can be varied by changing the pattern of the stencil used for etching during patterning of the patterned substrate. Suitable individual hydrogel spot size of the hydrogel array can be small enough to accommodate a single cell, but also large enough to accommodate many cells, for example. Thus, the individual hydrogel spot size of the hydrogel array can have any desired diameter. Particularly suitable individual hydrogel spot sizes of the hydrogel array can be about 10 μm and larger.

A patterned substrate can be prepared by creating hydrophobic regions and hydrophilic regions formed by self-assembled monolayers (SAMs), such as described in U.S. patent application Ser. No. 14/339,938, filed on Jul. 24, 2014, herein incorporated by reference to the extent it is consistent herewith. Suitable substrates for forming self-assembled monolayers are known to those skilled in the art and can be, for example, metal-coated substrates, silicon substrates, diamond substrates, polydimethylsiloxane (PDMS) substrates, and the like (as described in Love et al., Chem. Rev. 2005, 105:1103-1169, for example, which is hereby incorporated by reference to the extent its disclosure is consistent with the present disclosure). The patterned substrate can be prepared, for example, by forming regions with differential wettability on a substrate by immersing the substrate in a perfluorinated alkanethiol solution to allow perfluorinated alkanethiolate self-assembled monolayers (fluoraSAMs) to form. To form hydrophilic regions, a stencil can be placed on the fluoraSAMs metal-coated substrate to selectively protect regions of the fluoraSAMs metal-coated substrate from plasma etching. Exposed regions of the fluoraSAMs substrate can then be etched by oxygen plasma treatment to form etched fluoraSAMs in the substrate. The substrate is then immersed in a hydroxyl-terminated alkanethiol solution to form a hydrophilic alkanethiolate SAM (EG3SAM) in the etched regions of the substrate. The resulting patterned substrate possesses differential wettability based on the hydrophobic SAMs and hydrophilic SAMs.

Figure 4:
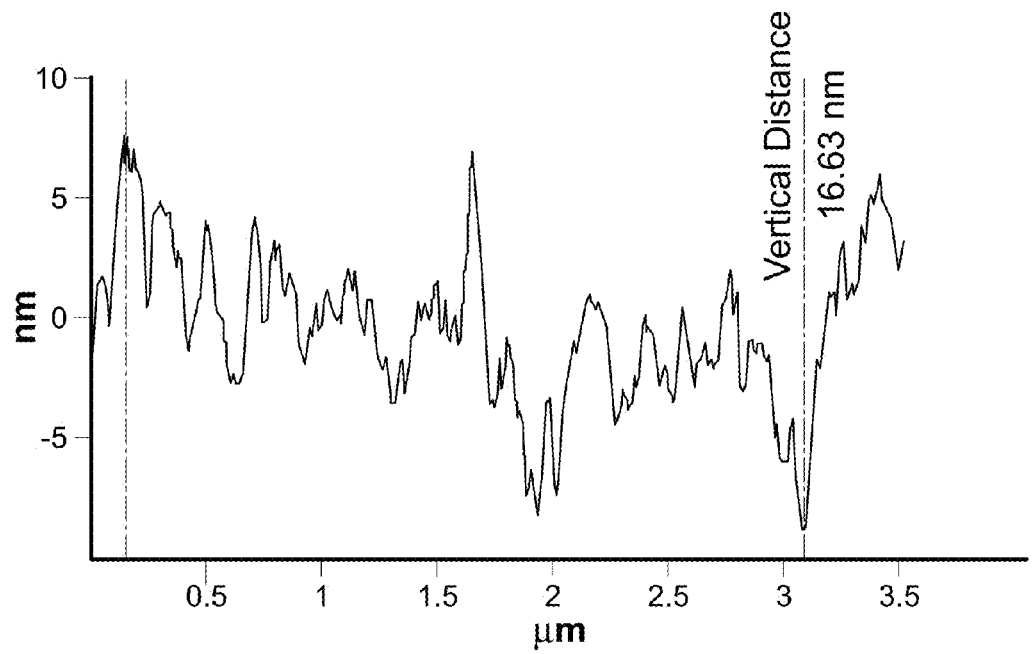
FIG. 4 is a graph illustrating the surface roughness of a hydrogel array as determined by atomic force microscopy.
Figure 6:
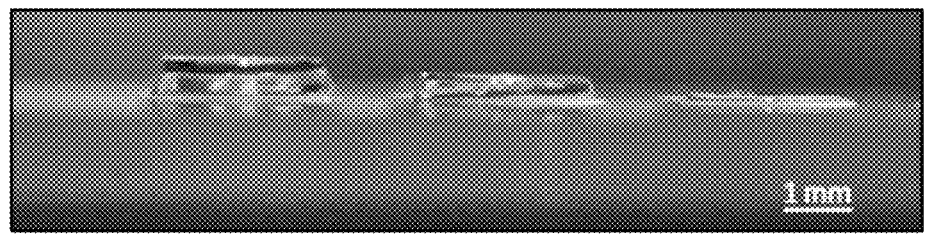
FIG. 6 is a side-on image showing individual hydrogel spots having different heights.

The method can further include placing a spacer between the patterned substrate and the surface-modified substrate. The spacer placed onto the patterned substrate while performing the method functions to define the height (or thickness) of the hydrogel forming the hydrogel array. A spacer may be particularly desirable when preparing higher (i.e., thicker) hydrogel arrays. Thus, the hydrogel array can have any desirable height (see e.g., FIG. 6). Suitable heights of the hydrogel array can be from about 20 micrometers (μm) to about 1 millimeter, however, hydrogel arrays can be made much higher than 1 millimeter if desired. The spacer also functions to prevent direct contact between the surface of the patterned substrate and the surface-modified substrate during formation of the hydrogel. The spacer used in the method can be any suitable material known to those skilled in the art. A particularly suitable spacer can be, for example, polydimethylsiloxane (PDMS). The height the hydrogel array can be determined, for example, using a microscope to focus from the top of the hydrogel down to the substrate, using a microscope to focus from the substrate up to the top of the hydrogel, and by measuring the surface roughness of a hydrogel array as determined by atomic force microscopy (see e.g., FIG. 4).

The preparation method further includes contacting a hydrogel precursor solution with the patterned substrate. In particular, the hydrogel precursor solution is contacted with the hydrophilic regions of the patterned substrate. The hydrophobic regions of the patterned substrate serve as a barrier between neighboring hydrophilic regions and also allow for the isolation of each hydrophilic region. The hydrogel precursor solution can be, for example, a combination of a polymer and a multifunctional polymer crosslinker.

When used as a hydrogel coating composition, preparation methods generally include contacting a hydrogel precursor solution with a substrate to be coated (e.g., surface of a cell culture plate).

Suitable polymers for the hydrogel precursor solution are known by those skilled in the art and can include, for example, poly(ethylene glycol), hyaluronic acid, gelatin, collagen, MATRIGEL®, dithiol polymers (e.g., acrylamide), click-based composite hydrogels (as discussed in Polizzotti et al. Biomacromolecules 2008, 9:1084-1087, which is hereby incorporated by reference to the extent its disclosure is consistent with the present disclosure), poly(ethylene glycol)-diacrylate, poly(ethylene glycol)-vinyl sulfone, and the like. Particularly suitable polymers can be, for example, poly(ethylene glycol). Particularly suitable polymers can be, for example, functionalized polymers. Functionalization of the polymer can be confirmed with $^1$H nuclear magnetic resonance spectroscopy, mass spectroscopy, Elman's reagent, UV-Vis spectroscopy, infrared spectroscopy, and other methods known to those skilled in the art, for example.

A particularly suitable functionalized polymer can be, for example, eight-arm poly(ethylene glycol) with terminal hydroxyl (—OH) groups (commercially available from JenKem Technology USA, Allen, Tex.) that is functionalized with norbornene. Eight-arm poly(ethylene glycol) can be functionalized with norbornene as described in Fairbanks et al. (Adv. Mater. 2009, 21:5005-5010).

Other particularly suitable polymers are poly(ethylene glycols) that may be functionalized using click chemistry. "Click" chemistry is an extremely versatile method for chemically attaching biomolecules, which is used to describe the [3+2] cycloaddition between alkyne and azide functional groups. Azides and alkynes are largely inert towards biological molecules and aqueous environments, which allows the use of the Huisgen 1,3-dipolar cycloaddition to yield stable triazoles that are very difficult to oxidize or reduce. Both the copper(I)-catalyzed and copper-free strained-alkyne variant reactions are mild and very efficient. These reactions can also be performed in small volumes of aqueous solutions, are insensitive to oxygen and water, and robust to functional groups on peptides. Click chemistry allows for selectivity in conjugation reactions in biological samples such as, for example, oligonucleotides and proteins. Particularly suitable reagents for click chemistry are commercially available from Laysan Bio Inc. (Arab, Ala.).

Generally, the hydrogel precursor solutions include concentrations of polymer of from about 36 mg/mL to about 70 mg/mL.

Suitable multifunctional polymer crosslinkers for use in the hydrogel precursor solution are known by those skilled in the art. In particular, the multifunctional crosslinker can be, for example, a bifunctional polymer crosslinker and a multifunctional polymer crosslinker (n>=2) and terminated with a functional group that can form a covalent bond with the polymer of the hydrogel precursor solution. Particularly suitable bi-functional polymer crosslinkers and multifunctional polymer crosslinkers can be, for example, polyethylene glycol dithiol (PEG-DT), protease-degradable crosslinkers and multi-arm poly(ethylene glycol) terminated with thiol (e.g., 4-arm PEG terminated with thiol). Suitable protease-degradable crosslinkers can be, for example, matrix metalloproteinase (MMP)-degradable crosslinkers as described in Nagase and Fields (Biopolymers 1996, 40:399-416, which is hereby incorporated by reference to the extent it is consistent with the present disclosure). More particularly, suitable MMP-degradable crosslinking peptides for use in the hydrogel precursor solution include KCGGPQGIWGQGCK (SEQ ID NO:27) and KCGGPQGIAGQGCK (SEQ ID NO:28).

The hydrogel precursor solution can further include an initiator. As known by those skilled in the art hydrogel polymerization can occur in the absence of an initiator. An initiator can, however, induce polymerization and/or decrease the polymerization rate. Suitable initiators are known to those skilled in the art and can be, for example, chemical initiators and photoinitiators. Particularly suitable photoinitiators can be, for example, IRGACURE 2959 photoinitiator (commercially available from Ciba/BASF, Ludwigshafen, Germany) and Eosin Y. Polymerization to form the hydrogel can also be performed by temperature change.

In another aspect, the hydrogel precursor solution can include a cell adhesion peptide. As used herein, a "cell adhesion peptide" refers to an amino acid sequence obtained from an adhesion protein to which cells bind via a receptor-ligand interaction. Varying the cell adhesion peptide and concentrations thereof in the solution allow for the ability to control the stability of the cellular attachment to the resulting hydrogel composition. Suitable cell adhesion peptides include, for example, RGD, RGDS (SEQ ID NO:1), CRGDS (SEQ ID NO:2), CRGDSP (SEQ ID NO:3), PHSRN (SEQ ID NO:4), GWGGRGDSP (SEQ ID NO:5), SIDQVEPYSSTAQ (SEQ ID NO:6), GRNIAEIIKDI (SEQ ID NO:7), DITYVRLKF (SEQ ID NO:8), DITVTLNRL (SEQ ID NO:9), GRYVVLPR (SEQ ID NO:10), GNRWHSIYITRFG (SEQ ID NO:11), GASIKVAVSADR (SEQ ID NO:12), GTTVKYIFR (SEQ ID NO:13), GSIKIRGTYS (SEQ ID NO:14), GSINNNR (SEQ ID NO:15), SDPGYIGSR (SEQ ID NO:16), YIGSR (SEQ ID NO:17), GTPGPQGIAGQGVV (SEQ ID NO:18), GTPGPQGIAGQRVV (SEQ ID NO:19), MNYYSNS (SEQ ID NO:20), KKQRFRHRNRKG (SEQ ID NO:21), CRGDGGGGGGGGGGGGGPHSRN (SEQ ID NO:29), CPHSRNSGSGSGSGSGRGD (SEQ ID NO:30), Acetylated-GCYGRGDSPG (SEQ ID NO:31), CRDGS (SEQ ID NO:32), cyclic RGD{Fd}C (SEQ ID NO:33), RKRLQVQLSIRT (SEQ ID NO:37), IKVAV (SEQ ID NO:38), YIGSR (SEQ ID NO:39), KRTGQYKL (SEQ ID NO:40), TYRSRKY (SEQ ID NO:41), KRTGQYKLGSKTGPGQK (SEQ ID NO:42), QAKHKQRKRLKSSC (SEQ ID NO:43), SPKHHSQRARKKKNKNC (SEQ ID NO:44), XBBXBX, wherein B=basic residue and X=hydropathic residue (SEQ ID NO:45), XBBBXXBX, wherein B=basic residue and X=hydropathic residue (SEQ ID NO:46), and RGDSP (SEQ ID NO:47).

The concentration of cell adhesion peptide in the hydrogel precursor solution will depend on the specific cell adhesion peptide being used as well as the other components in the hydrogel precursor solution. Typically, however, the hydrogel precursor solution includes from about 0.125 mM to about 4 mM cell adhesion peptide, including from about 0.25 mM to about 2 mM cell adhesion peptide. In one suitable embodiment, the cell adhesion peptide is CRGDS (SEQ ID NO:2), and the hydrogel precursor solution includes from about 0.25 mM to about 4 mM CRGDS (SEQ ID NO:2). In another suitable embodiment, the cell adhesion peptide is a cyclic RGD, and the hydrogel precursor solution includes from about 0.125 mM to about 2 mM cyclic RGD, particularly cyclic RGD{Fd}C (SEQ ID NO:33).

I In another aspect, the hydrogel precursor solution can include a soluble factor binder. In one aspect, a peptide for binding a soluble factor contained in a cell culture medium is included in the hydrogel precursor solution. The density (concentration) of the soluble factor binder in a hydrogel composition can be controlled by altering the concentration of the soluble factor binder in the hydrogel precursor solution. Examples of particularly suitable soluble factor binders are provided in Table 1, below.

TABLE 1

Soluble factor binder peptide sequences for hydrogel compositions.

| Name/Source | Sequence | SEQ ID NO: |
|---|---|---|
| Vascular Endothelial Growth Factor-Receptor Binding Peptide | GGGKLTWQELYQLKYKGI | 22 |
| Vascular endothelial growth factor receptor binding peptide (VR-BP) | KLTWQELYQLKYKGI | 23 |
| Bone morphogenetic protein-2 (BMP-2) receptor binding peptide | KIPKASSVPTEL | 24 |
| Bone morphogenic protein receptor-binding peptide | KIPKASSVPTELSAISTLYL | 25 |
| Heparin proteoglycan-binding peptide (HPG-BP) | KRTGQYKL | 26 |

TABLE 1-continued

Soluble factor binder peptide sequences for hydrogel compositions.

| Name/Source | Sequence | SEQ ID NO: |
|---|---|---|
| MMP-degradable peptide crosslinker | KCGGPQGIWGQGCK | 27 |
| MMP-degradable peptide crosslinker 2 | KCGGPQGIAGQGCK | 28 |
| VEGF binding peptide | CE{Fd}{Ad}{Yd}{Ld}IDFNWEYPASK | 35 |
| Scrambled VEGF binding peptide | CD{Ad}PYN{Fd}EFAWE{Yd}VIS{Ld}K | 36 |

The concentration of soluble factor binder in the hydrogel precursor solution will depend on the specific soluble factor binder being used as well as the other components in the hydrogel precursor solution. Typically, however, the hydrogel precursor solution includes from about 0 mM to about 0.3 mM soluble factor binder, including from about 0.03 mM to about 0.3 mM soluble factor binder.

In another aspect, hydrogel array can be prepared to include hydrogel spots having a variable modulus. Hydrogel arrays can have a range of moduli (expressed herein as substrate elastic moduli). Hydrogel arrays having hydrogel spots with different moduli can be prepared by changing the concentration of the polymer and/or changing the stoichiometric ratio of the multifunctional polymer (e.g., thiol-polyethylene glycol-thiol (SH-PEG-SH)) to polymer ratio in the hydrogel precursor solution (see e.g., FIG. 8). Suitable ratios can be from about 1:1 to about 4:1 (molar ratio). For example, the hydrogel modulus of a hydrogel using PEG-NB polymer and a dithiol crosslinker can be controlled, for example, by altering the ratio of PEG-NB to dithiol crosslinker by, for example, holding the PEG-NB wt % constant, then adding the crosslinker in a ratio that only crosslinks a portion of the PEG-NB arms such as, for example, from about 25% to 100% crosslinking.

In another aspect, the hydrogel precursor solution can further include a cell. Suitable cells are known to those skilled in the art and can include, for example, an embryonic stem cell, an embryonic stem cell-derived neuron, an embryonic stem cell-derived neural progenitor cell, an embryonic stem cell-derived astrocyte, an embryonic stem cell-derived microglial cell, an embryonic stem cell-derived endothelial cell, an embryonic stem cell-derived retinal pigment epithelial cell, an induced pluripotent stem cell, an induced pluripotent stem cell-derived neural progenitor cell, an induced pluripotent stem cell-derived astrocyte, an induced pluripotent stem cell-derived microglial cell, an induced pluripotent stem cell-derived endothelial cell, an induced pluripotent stem cell-derived retinal pigment epithelial cell, a mesenchymal stem cell, an umbilical vein endothelial cell, an NIH 3T3 fibroblast, a dermal fibroblast, a fibrosarcoma cell, a valvular interstitial cell, a cardiomyocyte, an induced pluripotent stem cell-derived cardiomyocyte, an endothelial progenitor cell, a circulating angiogenic cell, a neuron, a pericyte, a cancer cell, a hepatocyte, a pancreatic beta cell, a pancreatic islet cell and combinations thereof.

In another aspect, the hydrogel precursor solution can further include a microsphere carrier (i.e., microcarrier). Microsphere carriers can contain molecules such as, for example, cells, biomolecules, dyes and other molecules known to those skilled in the art. Microspheres can be degradable microspheres that dissolve or degrade to release the contents of the microsphere.

Once prepared, the hydrogel precursor solution is contacted with a substrate (e.g., a patterned surface-modified substrate, surface of a cell culture plate, etc.).

When used on a patterned surface-modified substrate, the surface-modified substrate can be, for example, mica, glass, silicon, diamond and metal oxide surfaces. The surface-modified substrate can be prepared, for example, by functionalizing a surface such as a glass coverslip having a silane monolayer. A particularly suitable surface-modified substrate can be, for example, a glass slide. A particularly suitable method for functionalizing the substrate can be, for example, silanization. The substrate can be surface-modified by activating both sides of the surface in oxygen plasma treatment. Oxygen plasma treatment can increase the number of activated hydroxyl groups on the surface of the substrate. As known by those skilled in the art, a silane monolayer can be prepared with an alkoxysilane that is dissolved in an anhydrous organic solvent such as, for example, toluene. Other suitable alkoxysilanes can be for example, aminosilanes, glycidoxysilanes and mercaptosilanes. Particularly suitable aminosilanes can be, for example, (3-aminopropyl)-triethoxysilane, (3-aminopropyl)-diethoxy-methylsilane, (3-aminopropyl)-dimethyl-ethoxysilane and (3-aminopropyl)-trimethoxysilane. Particularly suitable glycidoxysilanes can be, for example, (3-glycidoxypropyl)-dimethyl-ethoxysilane. Particularly suitable mercaptosilanes can be, for example, (3-mercaptopropyl)-trimethoxysilane and (3-mercaptopropyl)-methyl-dimethoxysilane. Other suitable silanes are commercially available (Sigma Aldrich, St. Louis, Mo.). Preparation of a surface-modified silane substrate can be performed using any silane having a terminal functional group that can participate in click chemistry as described herein. For example, mercaptosilane contains a terminal thiol that can react with the norbornene of the PEG-norbornene. Other suitable functional surface-modified silane substrates can be, for example, acrylates and methacrylates. Following surface-modification of the substrate, non-adhesive self-assembled monolayers are formed on the surface-modified substrate.

After contacting the substrate with the hydrogel precursor solution, the method includes polymerizing the hydrogel precursor solution such that polymerized hydrogel attaches (i.e., is coupled) to the substrate.

After contacting the substrate with the hydrogel precursor solution, the method includes polymerizing the hydrogel precursor solution such that polymerized hydrogel attaches (i.e., is coupled) to the substrate.

In one embodiment, the method can be used to form an array having "spots" or "islands" of hydrogel (referred to herein as "hydrogel spots") that are surrounded by a background that is substantially free, and even completely free, of hydrogel ("hydrogel-free"). In this embodiment, the hydrogel-free background corresponds to the hydrophobic regions of the patterned substrate and the hydrogel spots correspond to the hydrophilic regions of the patterned substrate. Referring to FIG. 1, the circles would represent the hydrogel spots that would be surrounded by a hydrogel-free region in this embodiment.

In another embodiment, the method can be used to form an array having hydrogel-free pools surrounded by a background of hydrogel (referred to herein as "a hydrogel background"). Referring to FIG. 1, the circles would represent the hydrogel-free pools that would be surrounded by the hydrogel-free background in this embodiment.

In another aspect, the present disclosure is directed to a patterned hydrogel array including hydrogel spots having variable modulus, variable shear modulus, variable ligand identity, variable ligand density and combinations thereof. Patterned hydrogel arrays including hydrogel spots having variable modulus, variable shear modulus, variable ligand identity, variable ligand density and combinations thereof can be prepared according to the methods described herein above.

Suitable ligands are known to those skilled in the art and can be, for example, any biomolecule containing a cysteine and/or functionalized with a thiol. Thiol-functionalizing of ligands can be performed using commercially available kits (e.g., Traut's Reagent (2-iminothiolane.HCl), Thermo Fischer Scientific, Rockford, Ill.). Suitable ligands can be, for example, proteins, peptides, nucleic acids, polysaccharides, lipids, biomimetic materials and other molecules, and combinations thereof. Particularly suitable proteins can be, for example, adhesion proteins. Particularly suitable adhesion proteins can be, for example, fibronectin, cadherin and combinations thereof. Particularly suitable peptides can be, for example, cell adhesion peptides and/or soluble factor binders, as described herein above.

Suitably, the hydrogel compositions of the present disclosure include combinations of cell adhesion peptides and soluble factor binders that are suspected of binding or interacting with a cell to affect cell attachment, spreading, migration, proliferation, differentiation, and formation of cellular structures (e.g., tubules). This aspect allows for using the hydrogel compositions to specifically screen soluble factor binders for effects on the cells such as, for example, cell attachment, spreading, migration, proliferation, differentiation, and formation of cellular structures. Additionally, soluble factor binders of unknown function can be immobilized in combination with a cell adhesion peptide to screen for changes in cell attachment, spreading, migration, proliferation, differentiation and formation of cellular structures.

Hydrogel compositions may further include variable moduli. Hydrogel compositions can have a range of stiffness (expressed herein as substrate elastic moduli). For example, hydrogels with different moduli can be prepared by changing the concentration of the polymer and/or changing the stoichiometric ratio of the multifunctional polymer (e.g., the bifunctional polymer thiol-polyethylene glycol-thiol (SH-PEG-SH)) to polymer ratio in the hydrogel precursor solution (see e.g., FIG. 8). Suitable ratios can be from about 1:1 to about 4:1 (molar ratio).

In another aspect, the patterned hydrogel array can be further assembled with a microarray add-on whereby the patterned hydrogel array is prepared with dimensions to accommodate add-ons of any size. Suitable microarray add-ons are commercially available (Grace Bio Labs, Bend, Oreg.). A microarray add-on can allow for the isolation of each individual hydrogel spot and hydrogel-free pool of the hydrogel array such that soluble factor presentation can be controlled. The microarray add-on can include the same number of openings as the number of individual hydrogel spots and hydrogel-free pools of the hydrogel array such that each hydrogel spot and hydrogel-free pool can be independently interrogated with soluble factor presentation. Alternatively, the microarray add-on can have larger openings that can accommodate more than one individual hydrogel spot and more than one individual hydrogel-free pool. For example, a microarray add-on can have openings large enough to accommodate a single hydrogel spot or a single hydrogel-free pool.

Methods of Using the Hydrogel Compositions

In yet another aspect, the present disclosure is directed to a method for screening for molecule-molecule interactions. The method includes preparing a hydrogel composition, wherein the hydrogel composition includes at least one soluble factor binder; contacting the hydrogel composition with a molecule known to or suspected of interacting with the at least one soluble factor binder; and analyzing the hydrogel composition.

The hydrogel composition can be prepared as described herein.

The hydrogel compositions can be analyzed using methods known to those skilled in the art. For example, hydrogel compositions can be analyzed using fluorescence, microscopy, and the like.

In one aspect, the present disclosure is directed to a method of screening a cell-surface interaction using hydrogel arrays as prepared herein to include hydrogel spots having variable densities (moduli), variable ligand identities, variable ligand densities, and combinations thereof. The ligand to be screened using the hydrogel array of the present disclosure can be a ligand that is known or suspected of binding or interacting with a cell. The method can further include assembling the patterned hydrogel array with a microarray add-on as described herein to separate one or more individual hydrogel spots of the hydrogel array such that individual hydrogel spots can be interrogated with soluble factors.

The method further includes contacting a cell with a patterned hydrogel array. As used herein, "contacting a cell" refers to seeding cells onto a patterned hydrogel array for the purpose of analyzing the cells and the hydrogel array. As known by those skilled in the art a cell suspension is typically transferred to a substrate and cells are given sufficient time to adhere to the substrate.

In another embodiment, cells can be incorporated into the hydrogel of the patterned hydrogel array using a hydrogel precursor solution that includes a polymer, a crosslinker, a cell adhesion peptide, and a cell.

The cells are then cultured for a desired time such as, for example, about one hour to about 30 days. After the desired time, cells can be analyzed by microscopy such as, for example, immunofluorescence microscopy, phase contrast microscopy, light microscopy, electron microscopy and combinations thereof. Cells can be analyzed for cell attachment, cell spreading, cell morphology, cell proliferation, cell migration, cell differentiation, protein expression, and combinations thereof.

Suitable cells can be any cell known by those skilled in the art. Particularly suitable cells can be, for example, an embryonic stem cell, an embryonic stem cell-derived neuron, an embryonic stem cell-derived neural progenitor cell, an embryonic stem cell-derived astrocyte, an embryonic stem cell-derived microglial cell, an embryonic stem cell-derived endothelial cell, an embryonic stem cell-derived retinal pigment epithelial cell, an induced pluripotent stem cell, an induced pluripotent stem cell-derived neural progenitor cell, an induced pluripotent stem cell-derived astrocyte, an induced pluripotent stem cell-derived microglial cell, an induced pluripotent stem cell-derived endothelial cell, an induced pluripotent stem cell-derived retinal pigment epithelial cell, a mesenchymal stem cell, an umbilical vein endothelial cell, an NIH 3T3 fibroblast, a dermal fibroblast, a fibrosarcoma cell, a valvular interstitial cell, a cardiomyocyte, an induced pluripotent stem cell-derived cardiomyocyte, an endothelial progenitor cell, a circulating angiogenic cell, a neuron, a pericyte, a cancer cell, a hepatocyte, a pancreatic beta cell, a pancreatic islet cell and combinations thereof.

The method may further include contacting the cell with a soluble molecule by including the soluble molecule in the culture medium in which the cells on the hydrogel spot of the patterned hydrogel array are cultured. Particularly suitable soluble molecules can be growth factors and proteoglycans. Suitable growth factors can be, for example, proteins from the transforming growth factor beta superfamily, fibroblast growth factor family of growth factors, platelet derived growth factor family of growth factors and combinations thereof. Particularly suitable growth factors can be, for example, vascular endothelial growth factor, bone morphogenetic proteins, fibroblast growth factor, insulin-like growth factor and combinations thereof. Suitable proteoglycans can be, for example, proteoglycans with heparin, heparin sulfate, and/or chondroitin glycosaminoglycan side chains.

In one particularly suitable embodiment, the present disclosure is directed to methods of screening for pro- and/or anti-tubulogenesis agents using the hydrogel compositions. As used herein, "tubulogenesis" refers to the ability of cells to adhere, spread, sprout, migrate, form cellular connections, form and maintain tubular networks (e.g., endothelial cell tubule network formation), vasculogenesis, and/or angiogenesis, and combinations thereof. Generally, the method includes: preparing the hydrogel composition of the present disclosure; providing an agent suspected of promoting or reducing tubulogenesis; contacting a cell with the hydrogel composition and agent; and analyzing the cell. The hydrogel composition generally includes the polyethylene glycol functionalized with norbornene, a crosslinking peptide, a cell adhesion peptide, and a soluble factor binder as described herein. As used herein, "reducing tubulogenesis" refers to minimizing, decreasing, or even eliminating tubulogenesis.

In another suitable embodiment, the present disclosure is directed to methods of promoting tubulogenesis. Generally, the methods include: preparing a hydrogel composition, wherein the hydrogel composition of the present disclosure, and a soluble factor binder; providing a culture media in contact with the hydrogel composition; contacting a cell in the culture media in contact with the hydrogel composition; and analyzing the cell. The culture media for use in culturing cells includes any suitable culture media known to one of skill in the applicable art. For example, culture media may include standard growth medium for the specific cell type (e.g., Medium 199 and EGM-2 BULLETKIT™ (Lonza, Basel, Switzerland) for HUVECs, VASCULIFE® and VEGF LifeFactors for iPSC-ECs and hESC-ECs (Lifeline Cell Technology, Frederick, Md.)). In one particular embodiment, the method includes promoting endothelial cell tubule network formation.

The methods and hydrogel compositions of the present disclosure allow for exceptional control over the density of the ligand on the hydrogel spot as well as exceptional control over the identity of the ligand on the hydrogel spot. The stiffness of the hydrogel can also be controlled. This control allows for screening for specific parameters of substrates for the culture of cells, which may alter and influence the outcome of the cellular response to the substrate and culture environment. The patterned hydrogel arrays of the present disclosure further allow for screening combinations of ligands. Thus, the patterned hydrogel arrays of the present disclosure present a tool to perform high-throughput multi-variable biological screens on a single surface for identifying specific parameters of substrates that may alter and influence the outcome of the cellular response to the substrate and culture environment.

The disclosure will be more fully understood upon consideration of the following non-limiting Examples.

EXAMPLES

Materials and Methods
PEG-Norbornene Synthesis

Eight-arm poly(ethylene glycol) (PEG) with terminal hydroxyl groups (—OH) and a molecular weight of 20 kDa was purchased from JenKem Technology USA (Allen, Tex.). Anhydrous pyridine, 4-dimethylamino)pyridine (DMAP), 5-norbornene-2-carboxylic acid, diethyl ether, and deuterated chloroform ($CDCl_3$, 99.8%) with 0.03% v/v tetramethylsilane (TMS) were purchased from Sigma Aldrich (St. Louis, Mo.). N,N'-Dicyclohexylcarbodiimide (DCC) and anhydrous dichloromethane (DCM) were purchased from ACROS Organics (Geel, Belgium). SNAKESKIN dialysis tubing having a 3.5K molecular weight cut-off was purchased from Thermo Fisher Scientific (Waltham, Mass.).

Eight-arm PEG-OH was functionalized with norbornene to utilize the thiol-ene chemistry for photopolymerization and immobilization of bioactive ligands (as described in Fairbanks et al. Adv. Mater. 2009, 21:5005-5010; Impellitteri et al. Biomaterials 2012, 33:3475-84; Belair and Murphy Acta Biomater. 2013; and Gould et al. Acta Biomater 2012, 8:3201-3209). The PEG-norbornene (PEG-NB) product of the functionalization reaction was filtered through a medium fritted Buchner funnel to remove salts formed during the reaction. The filtrate was then precipitated in 900 mL cold diethyl ether and 100 mL hexane. The solids were collected on qualitative grade filter paper and air dried overnight. The PEG-NB product was purified by dialysis against 4 L of $dH_2O$ at 4° C. for 72 hours (with water change every 8 hours) using rehydrated SNAKESKIN dialysis tubing to remove residual norbornene acid and subsequently freeze dried.

Norbornene functionalization of >90% was confirmed with 1H nuclear magnetic resonance spectroscopy. Samples were prepared at 6 mg/mL in $CDCl_3$ with TMS internal standard. Free induction decay (FID) spectra were obtained using spectroscopy services provided by the National Magnetic Resonance Facility at Madison on a Bruker Instruments Avance III 500i spectrometer at 400 MHz and 27° C.

Hydrogel Array Formation

Hydrogel arrays used for these experiments were composed of hydrogel spots immobilized on silanized glass substrates. Hydrogel spots were formed using gold surfaces patterned to possess regions with differential wettability, whereby the pattern was defined by an elastomeric stencil. The method of preparing the hydrogel arrays is further described below.

Glass Silanization

Glass coverslips and hydrochloric acid (HCl) solution were purchased from Thermo Fisher Scientific (Waltham, Mass.). Toluene, methanol, ethanol, 3-mercaptopropyl trimethoxysilane (3-MPTS), and dithiothreitol (DTT) were purchased from Sigma Aldrich (St. Louis, Mo.). A low pressure plasma system was purchased from Diener Electronic (Ebhausen, Germany).

Glass coverslips were silanized with 3-MPTS to create substrates presenting thiol groups capable of participating in thiol-ene reaction with PEG-NB and subsequently enable covalent immobilization of PEG-NB hydrogels (Seo et al. Colloids Surf B Biointerfaces 2012, 98:1-6). Liquid-phase silanization was performed as previously described (Seo et al. Colloids Surf B Biointerfaces 2012, 98:1-6; Halliwell et al. Anal Chem 2001, 73:2476-2483; and Cras et al. Biosens Bioelectron 1999, 14:683-688). Coverslips were sonicated for 45 minutes in 1:1 methanol to HCl to remove bulk contaminants Immediately prior to silanization, coverslips were activated by oxygen plasma treatment at 40 sccm and 50 W for 5 minutes on each side to increase the number of activated hydroxyl groups on the surface. Activated coverslips were placed in a coplin jar containing 2.5% v/v 3-MPTS in toluene for 4 hours. Excess silanes were removed from the surface of the coverslips by rinsing with toluene, 1:1 ethanol/toluene, and ethanol and dried with $N_2$ gas. Silanized coverslips were placed in an airtight chamber, purged with $N_2$ gas, and cured at 100° C. for 1 hour to crosslink the silanes coupled to the surface and reduce their susceptibility to hydrolysis. Silanized coverslips were stored in the $N_2$ gas purged chamber and protected from light until use. Prior to use, silanized glass coverslips were treated with 10 mM DTT in PBS for 30 minutes at 37° C. to reduce disulfides formed on the surface and to increase free thiols available at the surface (Vistas et al. Appl Surf Sci 2013, 286:314-318).

Fabrication of Elastomeric Stencils

Silicon wafers were purchased from WRS Materials (San Jose, Calif.). SU-8 100 photoresist was purchased from MicroChem (Newton, Mass.). Sylgard 184 silicone elastomer kit was purchased from Dow Corning Corporation (Midland, Mich.).

Polydimethylsiloxane (PDMS) elastomeric stencils were created using soft lithography as previously described (Jo et al. J Microelectromechanical Syst 2000, 9:76-81). The layout and geometries for the stencil were drawn using Adobe Illustrated, printed onto transparency films using a high resolution commercial laser printing service provided by ImageSetter (Madison, Wis.). The transparency film was used as a photo mask in combination with conventional photolithography techniques to create master molds with SU-8 negative-tone UV photoresist spin-coated on silicon wafers. To create the PDMS stencil, the curing agent and PDMS pre-polymer solution from the Sylgard elastomer kit were thoroughly mixed in a 1:10 weight ratio, spread onto the master mold, and cured at 80° C. for 6 hours. After curing, the PDMS stencils were peeled off from the master mold, briefly cleaned with ethanol, and dried with $N_2$ gas.

Hydrophobic/Hydrophilic Patterning

Gold-coated test slides (1,000 Å gold on 50 Å titanium metal thin films on 25 mm×75 mm×1 mm glass) were purchased from Evaporated Metal Films (Ithica, N.Y.). Perfluorinated alkanethiol ($HS-(CH_2)_{11}-O-(CH_2)_2-(CF_2)_5-CF_3$) was purchased from ProChimia Surfaces (Sopot, Poland). Hydroxyl-terminated alkanethiol ($HS-C_{11}-(O-CH_2-CH_2)_3-OH$) was synthesized as previously described (Prime and Whitesides J. Am. Chem. Soc. 1993, 115:10714-10721).

Gold-coated slides were patterned with hydrophobic and hydrophilic self-assembled monolayers (SAMs) of alkanethiolates to form regions with differential wettability. Differential wettability patterning served two purposes simultaneously: 1) defined the geometries of the hydrogel spots and 2) confined the contents of each hydrogel spot in the array. Gold-coated slides were immersed in ethanol and sonicated for ~2 minutes, rinsed with ethanol, and dried with $N_2$ gas to remove contaminants and gold oxide layers. Gold-coated slides were immersed in a 1 mM perfluorinated alkanethiol in ethanol solution for ≥2 hours to allow for perfluorinated alkanethiolate SAMs (fluoraSAMs) formation. After fluoraSAMs formation, fluoraSAMs gold-coated slides were cleaned with ethanol and dried with $N_2$ gas. To define hydrophilic regions on the substrate, PDMS stencils were placed on the fluoraSAMs gold-coated slides to selectively protect areas of the slides from plasma etching. The spatial and geometric patterning of the exposed regions on the fluoraSAMs gold-coated slides were defined by the pattern of the PDMS stencil, which, in turn, defined the geometry and spatial patterning of the hydrogel spots that the arrays could comprise. Exposed regions of the fluoraSAMs gold-coated slides were etched by oxygen plasma treatment at 40 sccm and 50 W for 1 minute. The etched gold-coated slides were cleaned with ethanol and dried with $N_2$ gas and immersed in a 0.1 mM hydroxyl-terminated alkanethiol in ethanol solution for ≥2 hours so that hydrophilic alkanethiolate SAMs ($EG_3$SAMs) were formed in the selectively-etched regions of the gold-coated slides. The resulting gold-coated slides with differential wettability were cleaned with ethanol and dried with $N_2$ gas before hydrogel formation.

Figure 2A:
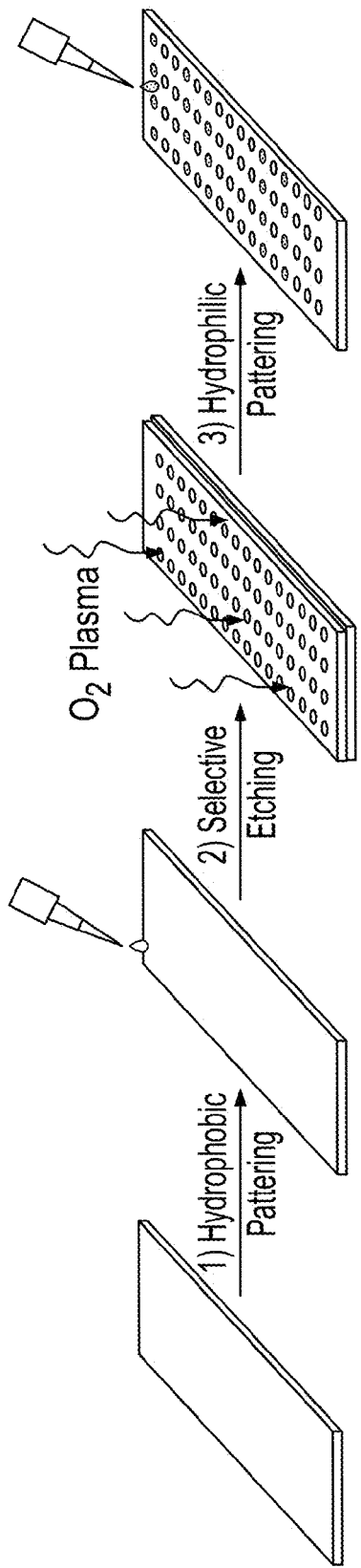
FIG. 2A is a schematic illustration of the steps for patterning a metal-coated substrate used in the method for preparing a hydrogel array of the present disclosure.
Figure 2B:
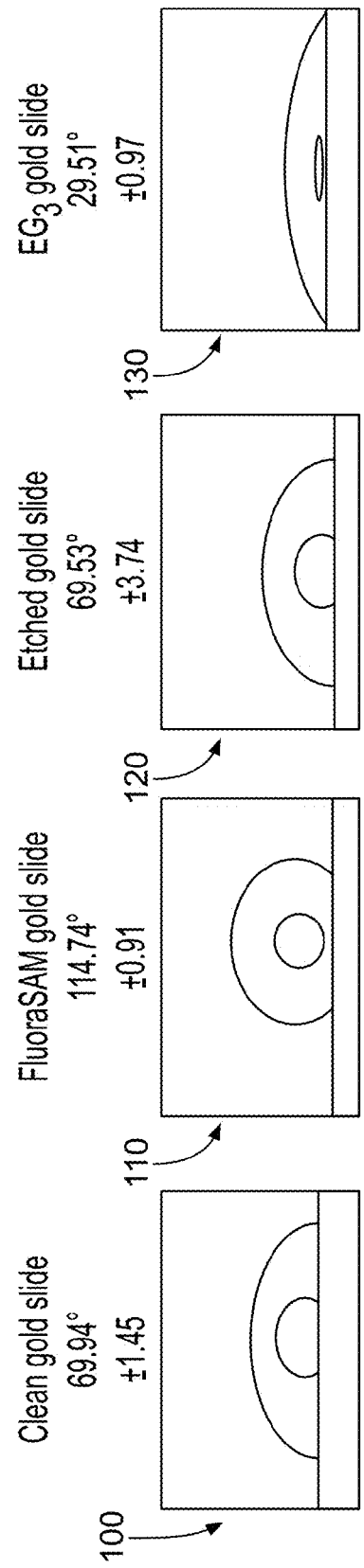
FIG. 2B are end view drawings of the metal-coated substrate during the steps for patterning a metal-coated substrate shown in FIG. 2A.

Hydrophobic and hydrophilic SAMs formation on the gold-coated slides were confirmed with contact angle measurements (see, FIG. 2B). Static contact angles were measured at room temperature using a contact angle goniometer (DataPhysics Contact Angle System OCA, San Jose, Calif.). A drop of distilled water (3 μL) was placed on the surface and the static contact angle was measured for 3 different samples at five different sites on each sample and averaged.

Hydrogel Spot Polymerization and Immobilization

PEG-NB was functionalized as described above. Bifunctional PEG dithiol (PEG-DT) crosslinker (3.4 kDa) was purchased from Laysan Bio (Arab, Ala.). IRGACURE 2959 photoinitiator was purchased from Ciba/BASF (Ludwigshafen, Germany). Cysteine-terminated peptides were purchased from GenScript USA (Piscataway, N.J.). Omnicure Series 1000 UV spot cure lamp (365 nm wavelength), light guide, and collimating adapter were purchased from Lumen Dynamics Group (Ontario, Canada). PDMS spacers with thickness dimensions corresponding to the desired hydrogel spot heights were fabricated using the same procedure as stated above.

Hydrogel precursor solutions were prepared by combining PEG-NB, PEG-DT, peptides, and photoinitiator and diluted to desired concentrations with phosphate buffered saline (PBS) immediately prior to hydrogel spots formation. To form each hydrogel array, a patterned gold-coated slide was rinsed with ethanol and dried with $N_2$ gas, PDMS spacers were placed onto hydrophobic regions of the slide, and hydrogel precursor solutions were spotted onto the hydrophilic regions. A DTT-treated silanized glass coverslip was used to sandwich the hydrogel precursor solutions between the coverslip and the slide. Hydrogel precursor solutions were polymerized by UV-initiated photo-crosslinking for 2 seconds at 90 mW/cm², with the light penetrating through the glass coverslip. The resulting polymerized hydrogel spots were covalently attached and immobilized onto the coverslip. Recall that the silanization procedure produced glass coverslips that were functionalized with thiol-terminated silanes that were capable of participating in the thiol-ene reaction used for hydrogel precursor solution polymerization, which effectively cross-linked the hydrogel network to the surface-bound silanes. The gold-coated slide was separated from the coverslip, which enabled the glass-immobilized hydrogel spots to cleanly detach from the gold-coated slide. The resulting glass-immobilized hydrogel spots, collectively referred to as the "hydrogel array", was sterilized for 1 hour in 70% ethanol and washed with PBS to remove any remaining unreacted components.

The bioactivity of each hydrogel spot in the array was defined by both the identity and concentration of the peptides incorporated therein. Peptides used in this study were CRGDS (SEQ ID NO:2), CRGD-(G)$_{13}$-PHSRN (SEQ ID NO:29), CRGD-(SG)$_5$-PHSRN (SEQ ID NO:30), acetylated-CRGDSP (SEQ ID NO:31), cyclic (RGD{Fd}C) (SEQ ID NO:33), and a non-bioactive scrambled peptide CRDGS (SEQ ID NO:32). To modulate the bioactivity of each hydrogel spot, different peptides were added to the hydrogel precursor solutions and, following UV-initiated crosslinking, the resulting polymerized hydrogel networks each presented different immobilized peptides. For all arrays, a total of 4 mM of peptides were incorporated into the hydrogel network. To concurrently change the bioactivity of the hydrogel spots via control of peptide identity and concentration, the desired concentration of the chosen bioactive peptide (containing the "RGD" sequence) was determined and the CRDGS (SEQ ID NO:32) peptide was supplemented to maintain a total peptide concentration of 4 mM in the hydrogel precursor solution.

The modulus of each hydrogel spot in the hydrogel array was defined by the total concentration of PEG in the crosslinked hydrogel network. Increasingly, the concentration of PEG-NB in the hydrogel precursor solution resulted in a larger amount of PEG crosslinked into the polymerized network, which resulted in an increase in the compressive modulus (see, FIG. 8).

Example 1

In this Example, a hydrogel array immobilized on a glass substrate was prepared.

Figure 1B:
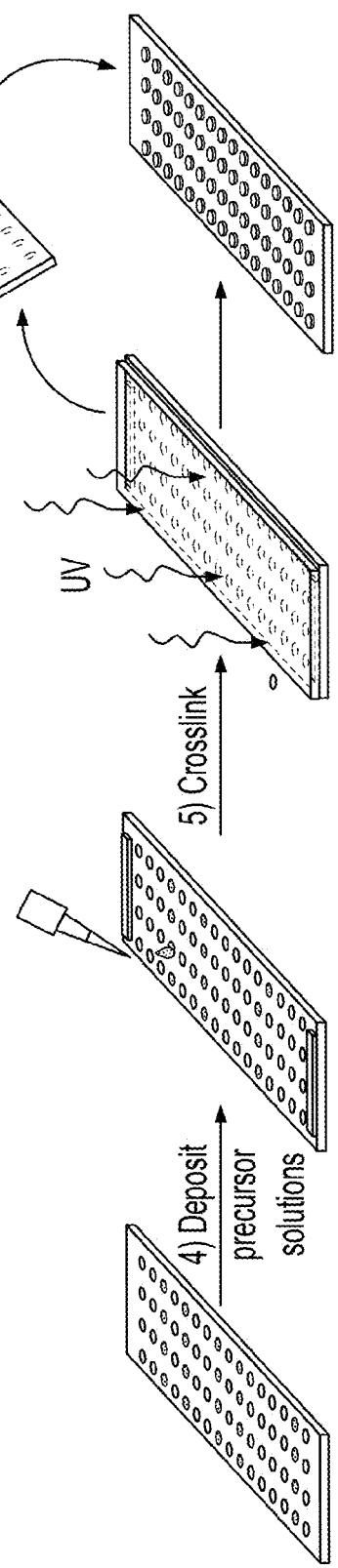

A gold substrate was modified with a patterned alkanethiolate self-assembled monolayer (SAMs) to provide isolated hydrophilic regions separated by a surrounding hydrophobic region (as illustrated in FIGS. 1A-1B). As illustrated in FIG. 2A (also shown in FIG. 1A), hydrophobic and hydrophilic SAMs formation on the gold-coated slides were confirmed with contact angle measurements. FIG. 2B provides end views during patterning of a gold substrate at the step before hydrophobic patterning 100; of the substrate having fluoraSAMs 110; of the substrate after etching 120; and of the substrate after hydrophilic patterning 130.

Figure 3:
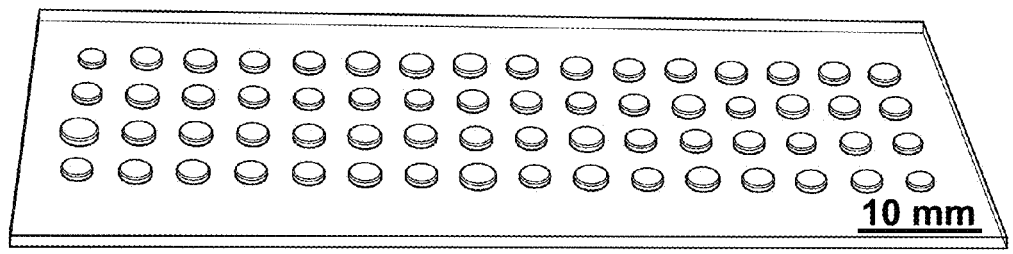
FIG. 3 is a photograph of a hydrogel array with 64 individual hydrogel spots prepared using the methods of the present disclosure.

Hydrogel precursor solutions containing all components required for polymerization reactions were deposited onto the hydrophilic SAMs regions of the patterned substrate (see, FIG. 1B). The hydrophilic regions served to both confine the contents of the solutions deposited onto each region and to define the geometries of the resulting polymerized hydrogel. Elastomeric spacers (with thickness dimensions equivalent to the desired hydrogel array height) were placed onto the hydrophobic areas of the patterned slide to define the height of the hydrogel array. A glass substrate, modified by silanization to possess SAMs with end-functional groups capable of participating in the polymerization reaction, was used to sandwich the hydrogel precursor solution. During the UV polymerization, the components of the hydrogel precursor solution formed a crosslinked network as well as formed covalent bonds with the end-function groups on the glass substrate. The polymerized hydrogels removed cleanly from the patterned gold substrate to produce a hydrogel array immobilized on the glass substrate (see, FIG. 3).

Example 2

In this Example, a hydrogel array was used to determine the effects of substrate properties on initial stem cell adhesion.

Figure 9:
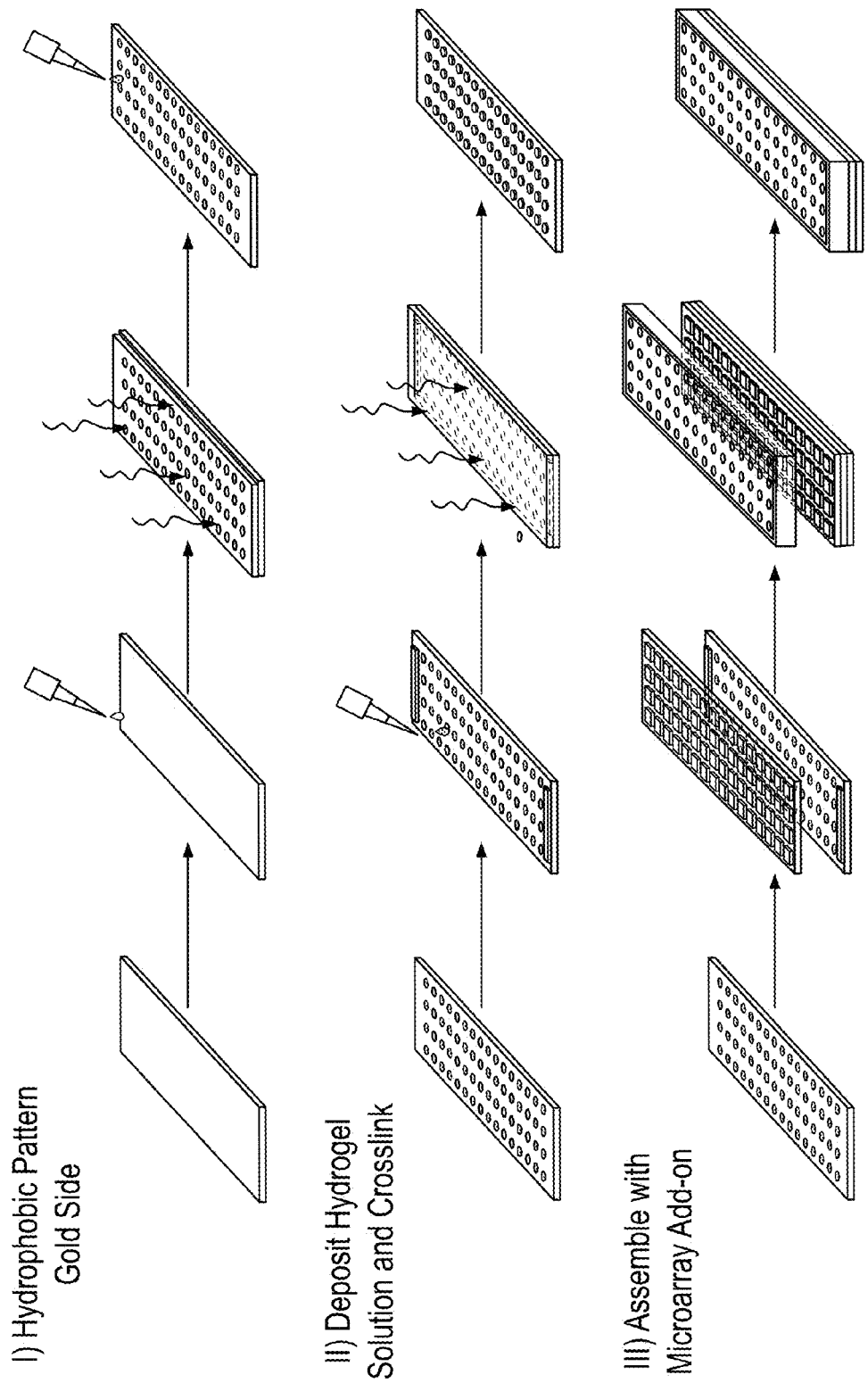
FIG. 9 is a schematic illustrating the steps for preparing a hydrogel array and further assembling the hydrogel array with a microwell add-on using the methods of the present disclosure.
Figure 10A:
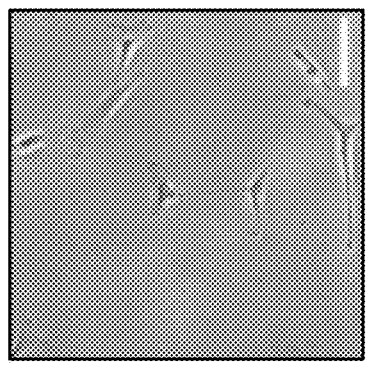
FIG. 10A-10C are photographs of hMSCs cultured on hydrogel arrays prepared using 4 wt. % (FIG. 10A), 6 wt. % (FIG. 10B) and 8 wt. % (FIG. 10C) polyethylene glycol and presenting linear RGD peptide, as discussed in Example 2. Scale bar=100 µm.
Figure 10B:
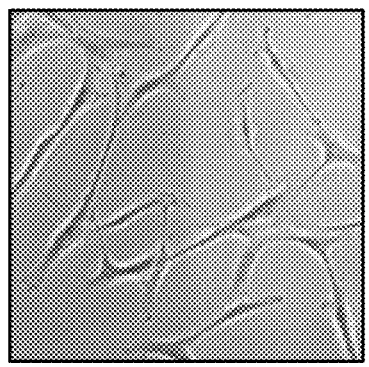
Figure 10C:
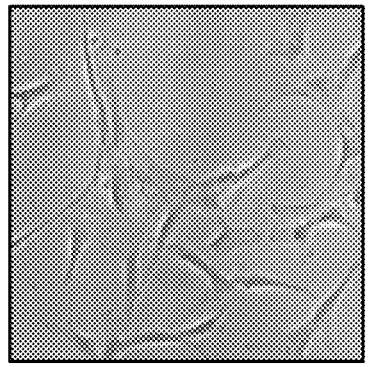

Poly (ethylene glycol) (PEG) hydrogel arrays were formed using patterned hydrophobic/hydrophilic self-assembled monolayers on gold substrates to both define the geometry and confine the contents of each hydrogel spot in the array as described above (see, FIGS. 1A-1B). UV-initiated thiol-ene crosslinking simultaneously polymerized the hydrogel and immobilized the hydrogel spots on the glass to result in the hydrogel array. As illustrated in FIG. 9, hydrogel arrays could be prepared with dimensions compatible with a 64-well microarray add-on (commercially available from Grace Bio-Labs, Bend, Oreg.).

Figure 7:
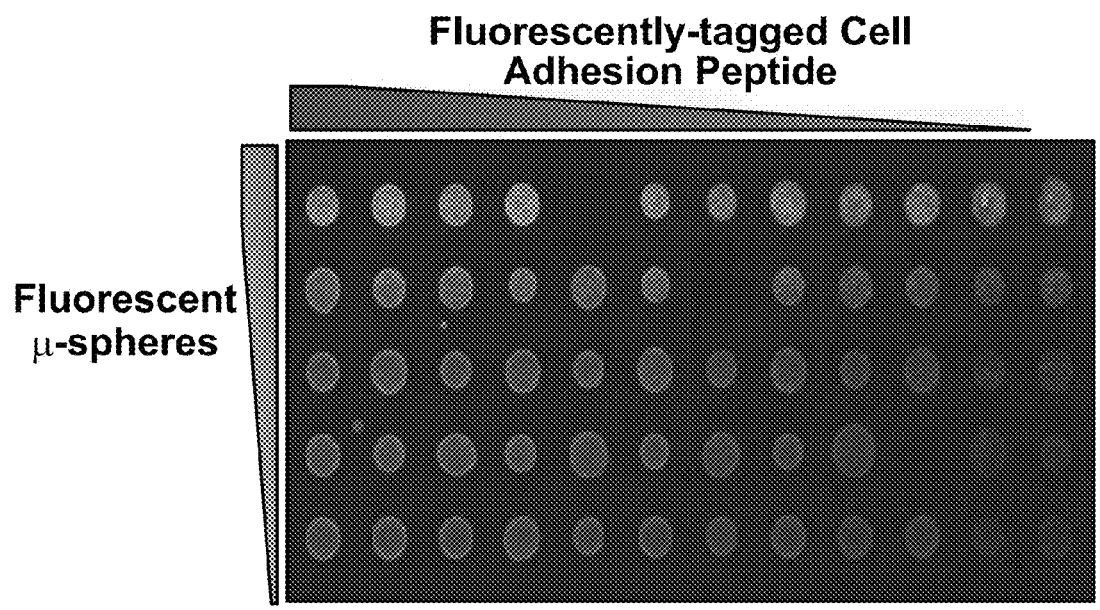
FIG. 7 is a hydrogel array showing differential patterning of individual hydrogel spots by increasing the density of a fluorescently-tagged peptide and increasing the density of encapsulated fluorescent microspheres, as discussed in Example 2.
Figure 8:
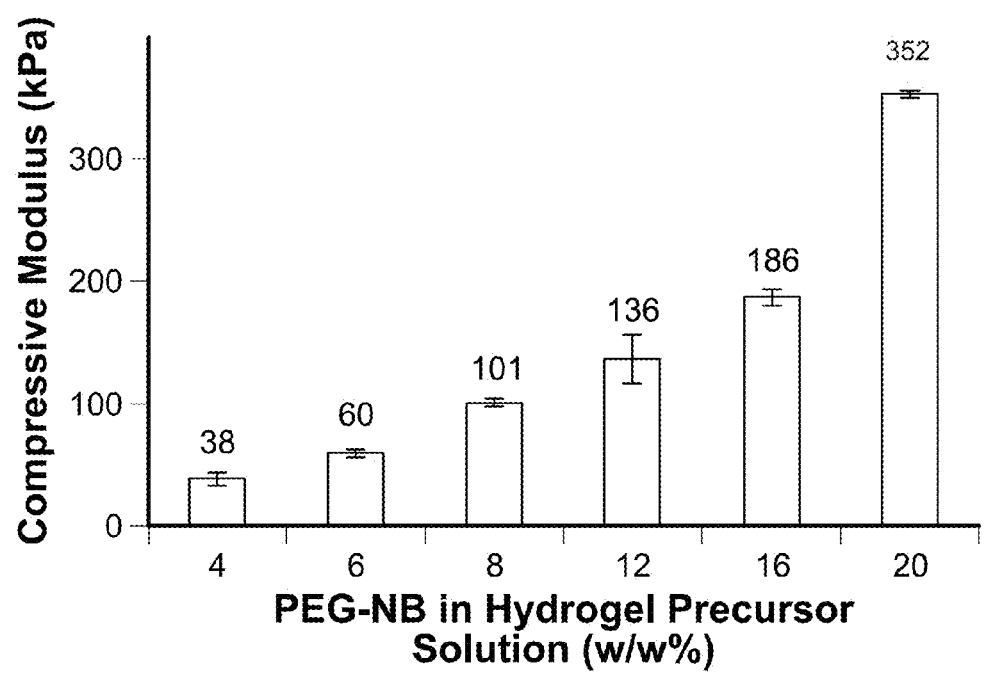
FIG. 8 is a graph illustrating control of the modulus of individual hydrogel spots of a hydrogel array by changing the total concentration of PEG-NB (w/w %) in the hydrogel precursor solution using the methods of the present disclosure.

Hydrogel solutions with fibronectin-derived peptides, fluorescent microspheres and a dithiol crosslinker were deposited onto the SAMs and sandwiched with a silanized glass slide. As shown in FIG. 7, individual hydrogel spots of the hydrogel array could be prepared to include varying amounts of fluorescently-tagged peptides as well as varying amounts of fluorescent microspheres. Hydrogel solutions with varying PEG or crosslinker concentration were also prepared prior to crosslinking to change the stiffness, peptide identity or peptide concentration (FIG. 8). The resultant arrays (see, FIG. 3) included 2.4 mm diameter, 150 um height posts. Human mesenchymal stem cells (hMSCs) were cultured on posts with varying PEG concentrations (4 wt %, 6 wt % and 8 wt %) to change stiffness and monitored for changes in initial cell adhesion and spreading. Human embryonic stem cells (hESCs) were cultured on posts with varying peptide identity (blank, RDGS, RGDS (SEQ ID NO:1), RGD-PHSRN (SEQ ID NO:34), RGDSP (SEQ ID NO:47), and cyclic RGD) and monitored for changes in initial cell adhesion and spreading.

Figure 11A:
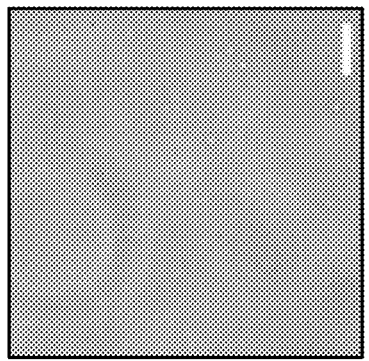
FIG. 11A-11C are photographs of hESCs cultured on hydrogel arrays prepared using 4 wt. % (FIG. 11A), 6 wt. % (FIG. 11B) and 8 wt. % (FIG. 11C) polyethylene glycol and presenting varying peptide identity, as discussed in Example 2. Scale bar=100 µm.
Figure 11B:
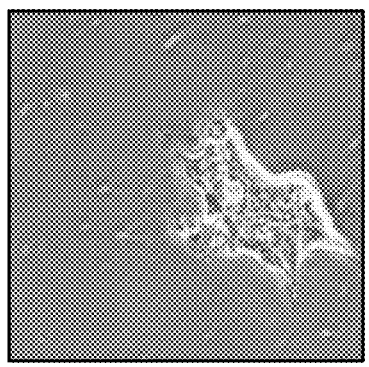
Figure 11C:
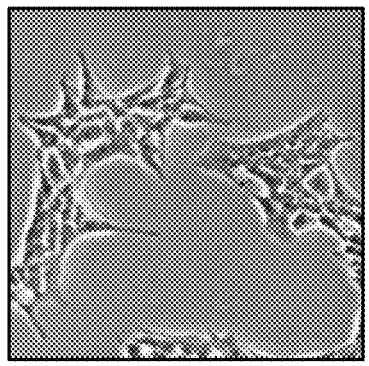

As shown in FIGS. 10A-10C, 2D culture of hMSCs demonstrated cell spreading dependence in response to changes in modulus consistent with published observations (see, Engler et al. Cell 126:677 (2006)). 2D culture of hESCs in chemically-defined, albumin-free media demonstrated that cell adhesion was highly specific to peptide-presenting spots. Both hESC cell adhesion and spreading were dependent on the binding affinity of integrin receptors to immobilized peptides (see, FIG. 11). Arrays allowed for changes in hydrogel spot shape, hydrogel spot height (by changing patterned hydrogel spot shapes or adding spacers), hydrogel spot stiffness and hydrogel spot peptide concentrations, and was adaptable for both 2D and 3D cell culture.

These results demonstrate that the method for preparing hydrogel arrays as described herein provides the capability to control stiffness, immobilized ligand identity and ligand concentration (density), and soluble growth factor presentation. The hydrogel arrays of the present disclosure can support cell adhesion and survival and allow for screening complex cell-environment interactions.

Example 3

In this Example, a patterned hydrogel array was used to investigate endothelial cell tubule network formation (i.e., "tubulogenesis") in vitro.

Specifically, patterned hydrogel arrays were composed of 8-arm, 20 kDa poly(ethylene glycol) functionalized with norbornene. The patterned hydrogel arrays included hydrogel spots containing from 30-60 mg/mL PEG, 30-70% crosslinking with an MMP-degradable crosslinking peptide (KCGGPQGIWGQGCK (SEQ ID NO:27) or KCGGPQGIAGQGCK (SEQ ID NO:28)) and 0.25-2 mM of a cell adhesive peptide (CRGDS (SEQ ID NO:2)). Patterned hydrogel array spots were seeded with human umbilical vein endothelial cells (HUVECs), human induced pluripotent stem cell-derived endothelial cells (iPSC-ECs), and human embryonic stem cell-derived endothelial cells (hESC-ECs) in culture media containing standard growth medium for each cell type (Medium 199 and EGM-2 BULLETKIT™ (Lonza, Basel, Switzerland) for HUVECs, VASCULIFE® and VEGF LifeFactors for iPSC-ECs and hESC-ECs (Lifeline Cell Technology, Frederick, Md.)).

Figure 12A:
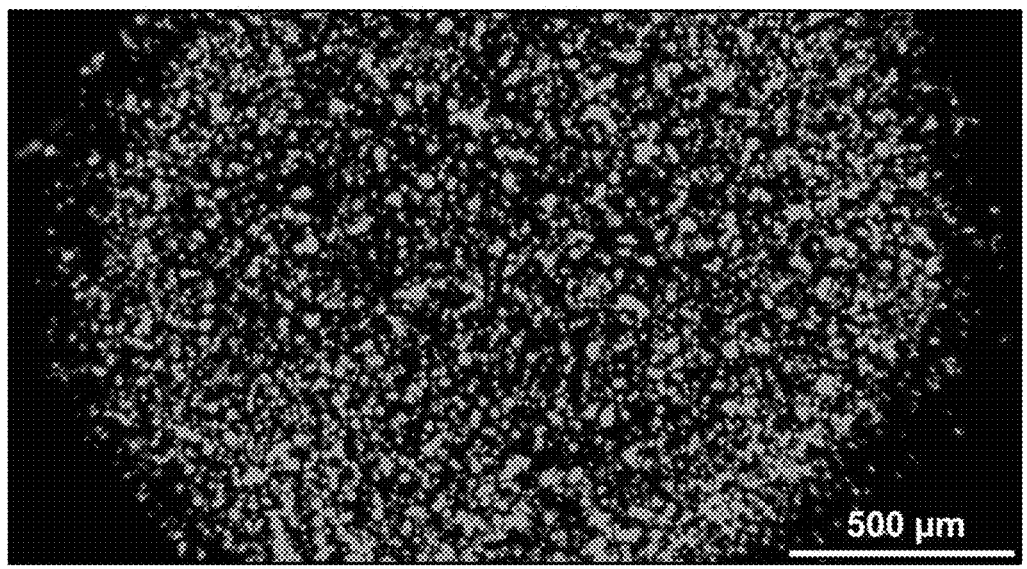
FIG. 12A shows endothelial cells encapsulated in a hydrogel spot that did not support tubulogenesis as discussed in Example 3.
Figure 12B:
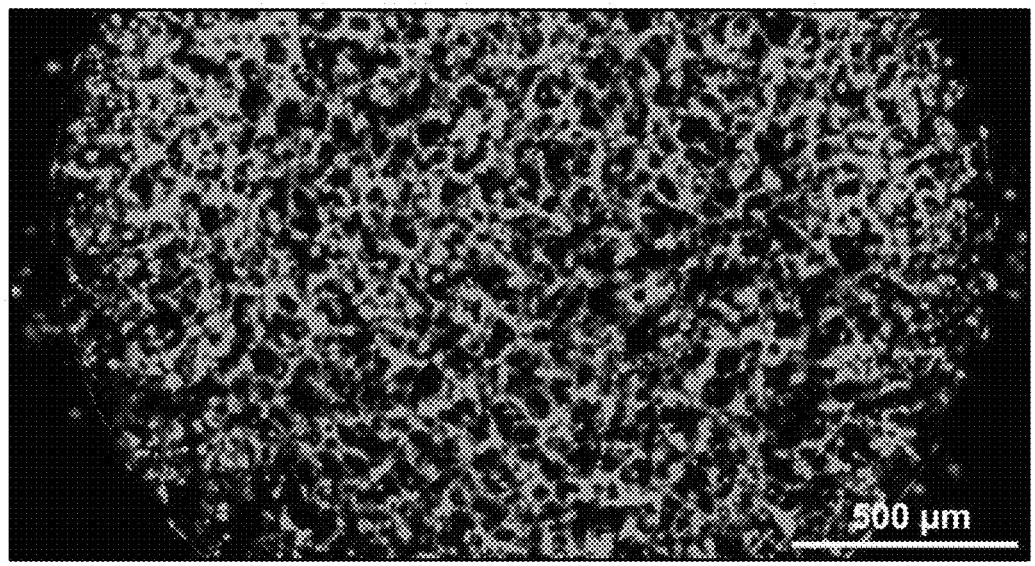
FIG. 12B shows endothelial cells encapsulated in a hydrogel spot that underwent tubulogenesis as discussed in Example 3.

Hydrogel spots having less than 36 mg/mL PEG, less than 30% MMP-degradable crosslinking peptide and less than 0.25 mM of the cell adhesive peptide did not form tubules (FIG. 12A). The hydrogel spots that contained between 36-60 mg/mL PEG, 30-70% crosslinking with an MMP-degradable crosslinking peptide and 0.25 mM-2 mM of the cell adhesive peptide supported EC tubule formation (FIG. 12B). Networks were first observed at 4 hours for HUVECs and 24 hours for iPSC-ECs, and networks were stable up to 48 hours for HUVECs, up to 21 days for iPSC-ECs, and up to 16 days for hESC-ECs. Furthermore, the persistence of tubule networks was enhanced by incorporating biochemical sequestering peptides for vascular endothelial growth factor (VEGF) into hydrogel arrays or by 3D co-culture with support cells (e.g. iPS-derived Fib-2 mesenchymal stromal cells, human brain-derived pericytes, human mesenchymal stem cells).

Figure 12C:
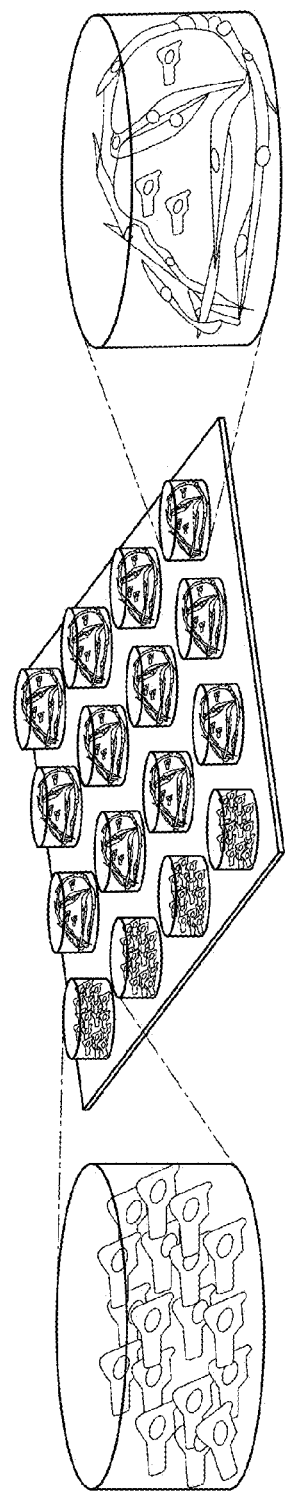
FIG. 12C is a schematic illustration showing a hydrogel array seeded with cells and an enlargement of a hydrogel spot that did not support tubulogenesis and an enlargement of a hydrogel spot that did support tubulogenesis as discussed in Example 3.

Hydrogel arrays that promoted network formation of HUVECs (on 2D hydrogels and in 3D hydrogels) and iPSC-ECs (in 3D) contained 50% crosslinking with the MMP-degradable peptides and 2 mM of the cell adhesive peptide (CRGDS (SEQ ID NO:2)), and network formation of hESC-ECs (in 3D) was promoted in conditions that contained 45-50% crosslinking with 2 mM of the cell adhesive peptide (CRGDS (SEQ ID NO:2)). FIG. 12C shows a schematic illustration of a hydrogel array for investigating tubulogenesis as described in this Example.

Example 4

In this Example, an array of PEG hydrogels was used to screen the combined effects of adhesion ligand density, modulus and VEGFR2 signaling on pro-angiogenic cell behaviors using encapsulated human umbilical vein endothelial cells (HUVECs) as a model cell type.

It was hypothesized that cell adhesion, hydrogel modulus and VEGFR2-mediated signaling would modulate viability, proliferation and tubulogenesis of HUVECs. Further, it was believed that a VEGFR2 inhibitor modulates viability, proliferation and tubulogenesis differently depending on surrounding ECM contexts. Accordingly, the effects of the inhibitor in the PEG hydrogels were compared to effects in MATRIGEL®, a standard platform for screening angiogenesis drugs in vitro.

Materials and Methods

Cell Culture

Human umbilical vein endothelial cells (HUVECs) were purchased From Lonza (Walkersville, Md.) and cultured in medium 199 (M199) (Mediatech Inc. Manassas, Va.) supplemented with EGM-2 Bulletkit (Lonza). The medium supplement contained 2% bovine serum albumin as well as hydrocortisone. hFGF-B. VEGF. R3-IGF-1, ascorbic acid, heparin, FBS, hEGF, and GA-1000. For simplicity M199 supplemented with EGM-2 will be referred to as "growth medium." Growth medium was changed every other day and cells were passaged every 4-5 days. Cell passages were performed using 0.05% trypsin solution (HyClone, Lagan, HT) and detached cells were recovered in M199 supplemented with 10% cosmic calf serum (HyClone). All media was supplemented with 100 U/mL Penicillin/100 µg/mL Streptomycin (HyClone). The cells were maintained in a humidified 37° C. incubator with 5% $CO_2$ and used between 7 and 16 population doublings in all experiments.

Poly(Ethylene Glycol) (PEG) Functionalization with Norbornene

PEG-norbornene (PEGNB) was synthesized as follows. Solid 8-arm PEG-OH (20 kDa molecular weight, tripentaerythritol core, Jenkem USA, Allen Tex.), dimethylaminopyridine and pyridine (Sigma Aldrich. St. Louis, Mo.) were dissolved in anhydrous dichloromethane (Fisher Scientific, Waltham, Mass.). In a separate reaction vessel, N,N'-dicyclohexylcarbodiimide (Thermo Scientific, Waltham, Mass.) and norbornene carboxylic acid (Sigma Aldrich) were dissolved in anhydrous dichloromethane. Norbornene carboxylic acid was covalently coupled to the PEG-OH through the carboxyl group by combining the PEG solution and norbornene solutions and stirring the reaction mixture overnight under anhydrous conditions. Urea was removed from the reaction mixture using a glass fritted funnel and the filtrate was precipitated in cold diethyl ether (Fisher). The precipitated PEGNB was collected and dried overnight in a Buchner funnel. To remove impurities, the PEGNB was dissolved in chloroForm (Sigma Aldrich), precipitated in diethyl ether and dried a second time in a Buchner Funnel. To remove excess norbornene carboxylic acid, PEGNB was dissolved in de-ionized $H_2O$, dialyzed in de-ionized $H_2O$ for 1 week and filtered through a 0.4 µm pore-size syringe filter. The aqueous PEGNB solution was frozen using liquid nitrogen and lyophilized Functionalization of PEG with norbornene groups (FIG. 13A) was quantified using proton nuclear magnetic resonance spectroscopy (NMR) to detect protons of the norbornene-associated alkene groups located at 6.8-7.2 PPM. Functionalization efficiency for norbornene coupling to PEG-OH arms was above 88% for all PEGNB used in these experiments.

Pre-Coupling Adhesion Peptides to PEGNB

Lyophilized PEGNB was dissolved in 10 mM phosphate buffered saline (1×PBS) at 10 mM concentration (80 mM norbornene groups) and combined with 0.05% w/v IRGACURE 2959 photoinitiator (12959) (Ciba Specialty Chemicals. Tarrytown, N.Y.) as well as 2× molar excess of either amidated Cys-Arg-Gly-Asp-Ser (CRGDS) adhesion peptide (SEQ ID NO:2) or amidated Cys-Arg-Asp-Gly-Ser (CRDGS) (SEQ ID NO:32), a scrambled nonfunctional peptide (Genscript, Piscataway, N.J.). The mixture was reacted under 365 nm UV light for 3 minutes at a dose rate of 4.5 mW/$cm^2$ to covalently attach the peptides to norbornene groups (FIG. 13A) via a thiolene reaction. To remove buffer salts and unreacted peptide from the decorated PEGNB, the reaction mixture was dialyzed in de-ionized $H_2O$ for 2 days. The dialyzed solution was frozen in liquid nitrogen and lyophilized. The coupling efficiency of PEGNB to the peptides was quantified using proton NMR to detect disappearances of alkene protons at 6.8-7.2 PPM caused by covalent bonding of the peptides to the norbornene group. For simplicity, precoupled PEGNB molecules will be referenced as PEGNB-CRGDS (SEQ ID NO:2) and PEGNB-CRDGS (SEQ ID NO:32).

Forming PEG Hydrogels

Figure 13A:
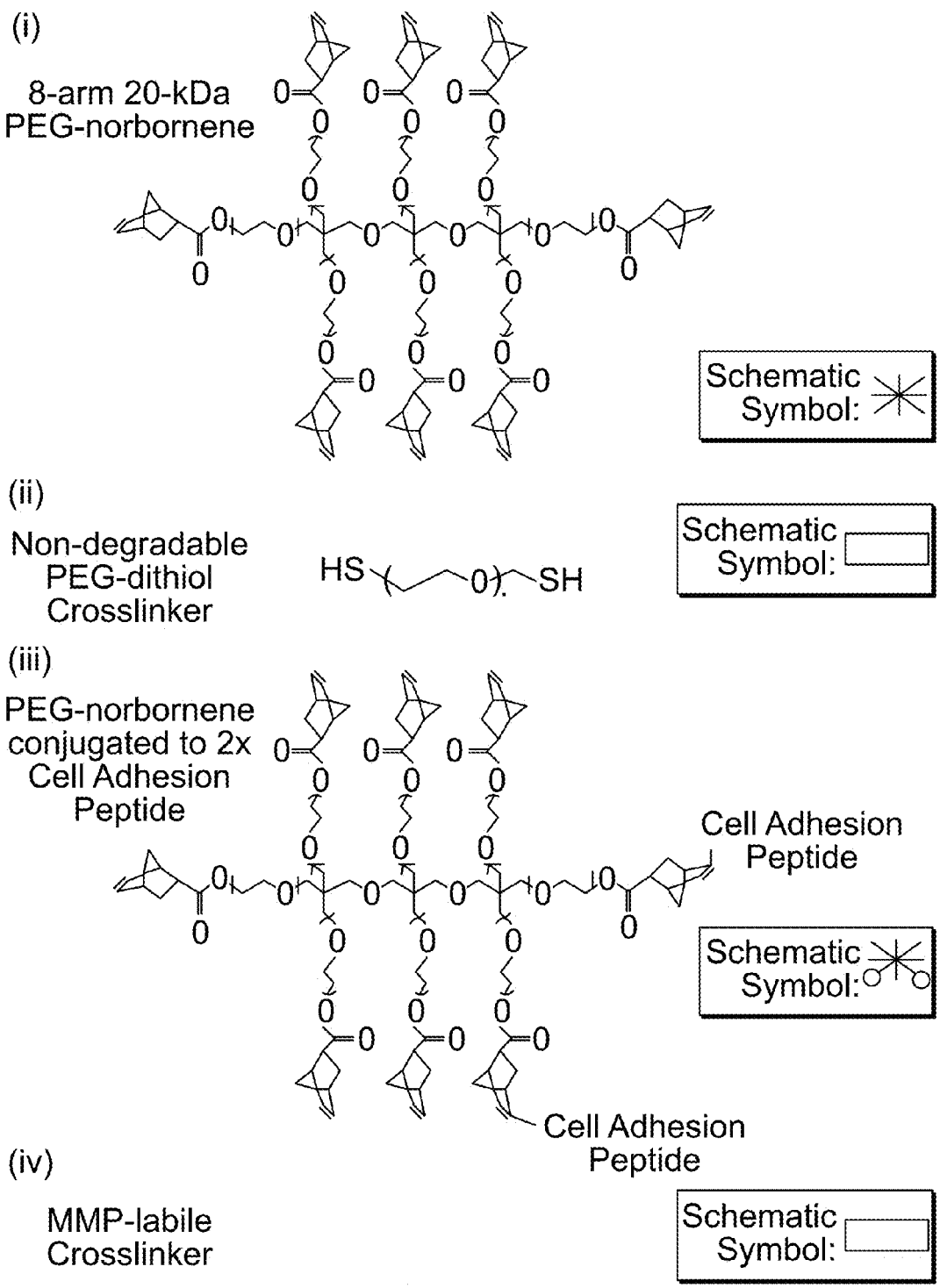
FIGS. 13A-13C depict molecules included in PEG hydrogels of the present disclosure.
Figure 13B:
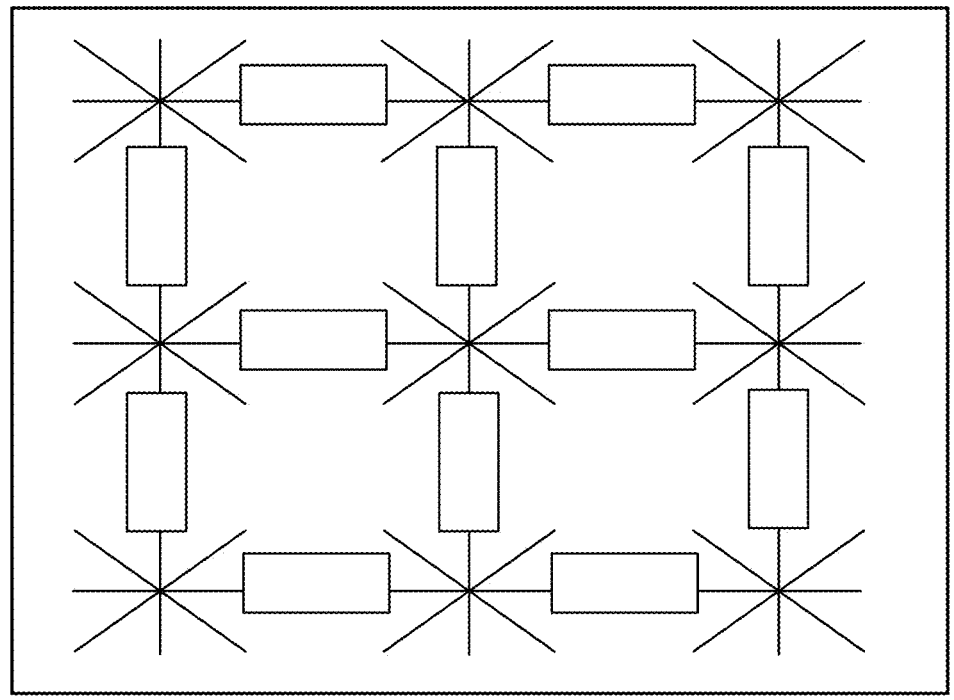
Figure 13C:
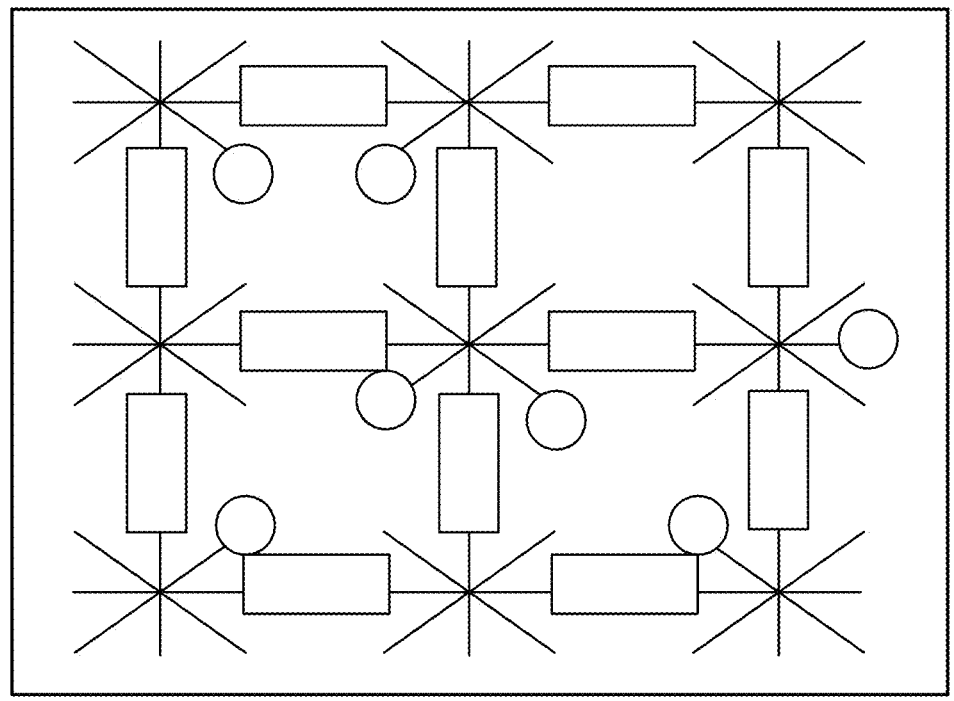
Figure 14B:
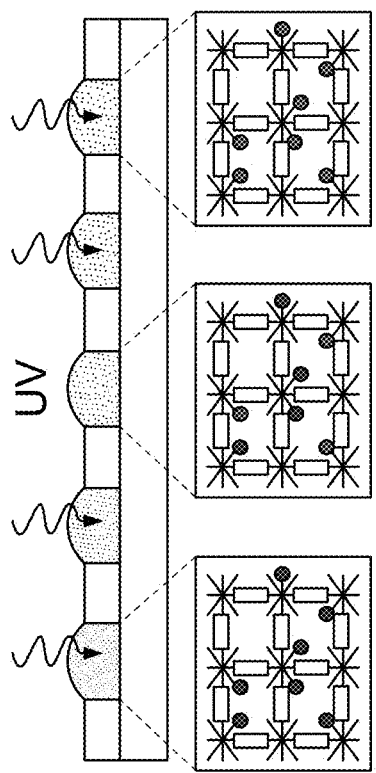
FIGS. 14A-14E depict a schematic representation of hydrogel array fabrication: A) separate hydrogel spot solutions containing various ratios of CRGDS (SEQ ID NO:2) adhesion peptide (red circles) and a scrambled CRDGS (SEQ ID NO:32) non-functional peptide (blue circles) are pipetted into wells of a PDMS stencil. Total pendant peptide concentration is fixed at 2 mM in all solutions; B) hydrogel spots are crosslinked in the stencil using UV light; C) crosslinked 1-mm thick "background" hydrogel slab is laid on top of the crosslinked bioactive hydrogel spots (A thin layer of background hydrogel solution is added to the slab to anchor the cured spots to the background); D) hydrogel spots are anchored to the background after treatment with UV light; and E) completed hydrogel array is removed from the stencil. Red boxes highlight the raised spots in the schematic and side view images of the arrays.
Figure 14D:
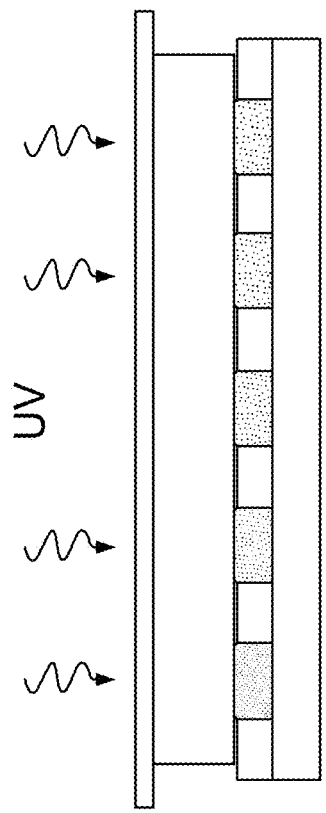
Figure 14A:
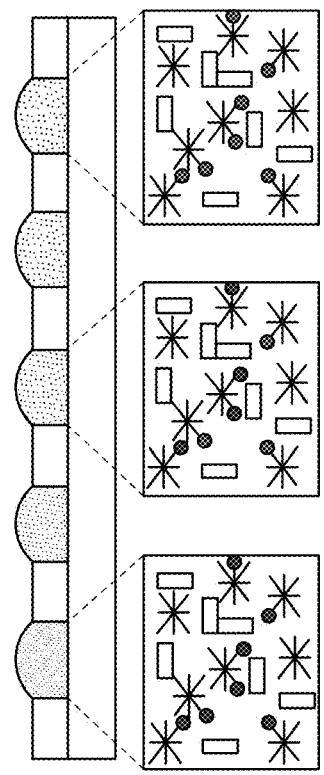
Figure 14C:
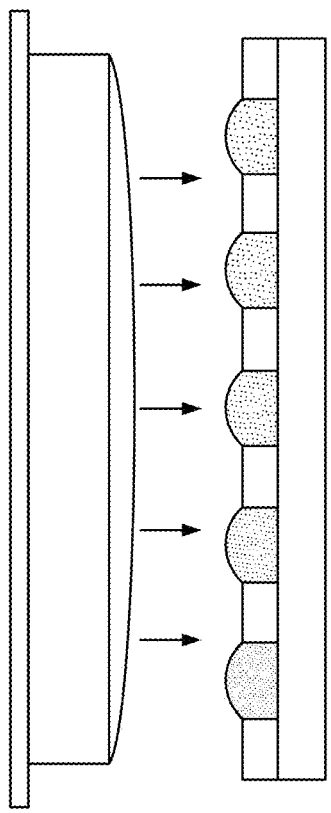
Figure 14E:
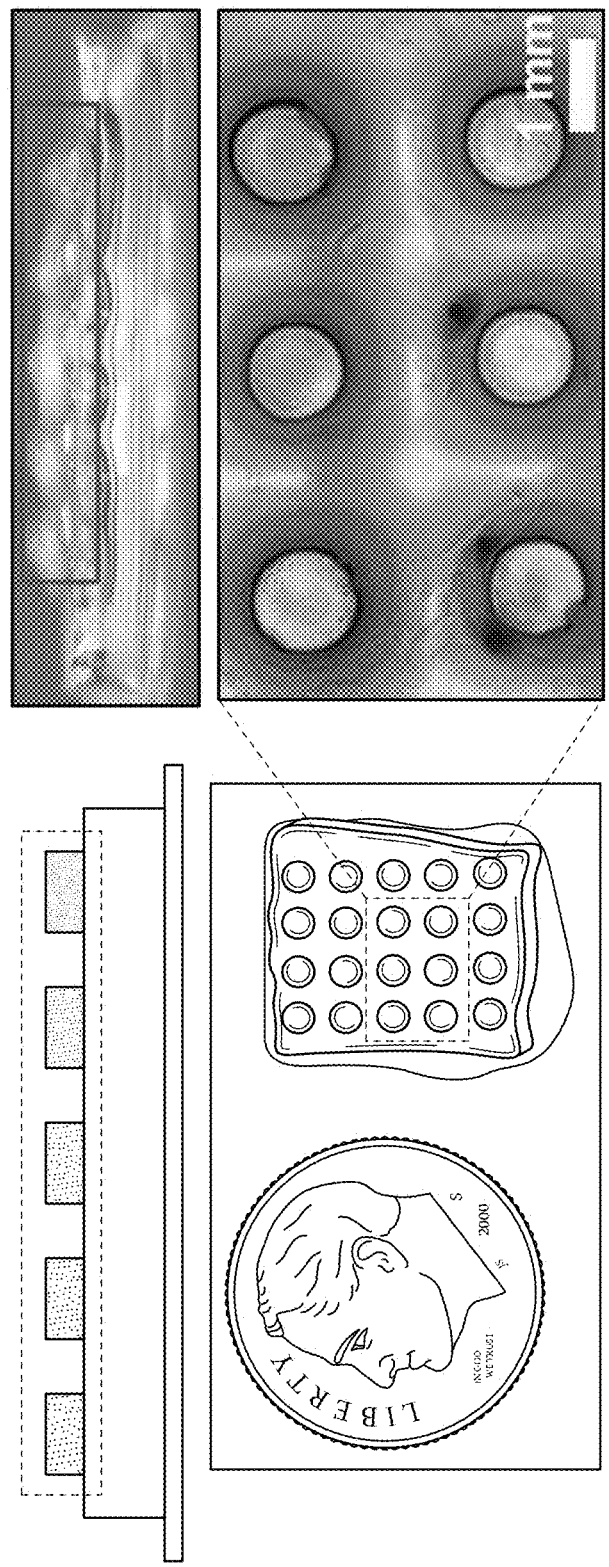

Hydrogel array constructs were formed from 2 separate hydrogels: the inert hydrogel "background" (FIG. 13B) that is crosslinked using 3.4 kDa PEG-dithiol (PEG-DT) (FIG. 13A) crosslinking molecule (Laysan Bio, Arab, Ala.). and "hydrogel spots" (FIG. 13C) that are decorated with adhesion peptides and crosslinked using MMP-degradable KCG-GPQGIWGQGCK peptide (SEQ ID NO:27) (FIG. 13A) (Genscript). All hydrogel solutions were created in serum-free M199 and consisted of PEGNB, 0.05% w/v 12959 and 2× molar excess crosslinking molecule to PEGNB to achieve 50% crosslinking density (FIGS. 13A-13C). To vary cell adhesion to the hydrogels, precoupled PEGNB-CRGDS (SEQ ID NO:2) and PEGNB-CRDGS (SEQ ID NO:32) molecules were added to the solutions to achieve desired adhesion peptide concentration with a total of 2 mM pendant peptide included in every solution. To vary the modulus of the background hydrogels the combined percent weight of PEGNB and PEG-DT was varied between 4, 6 or 8% w/v. To vary the modulus of the hydrogel spots, the combined percent weight of the PEGNB, degradable crosslinking molecule and adhesion peptides was varied between 4.2, 5 and 7% w/v.

Mechanical Properties of PEG Hydrogels

Mass equilibrium swelling ratios and shear modulus were measured in background hydrogel samples and bulk samples of hydrogel spots. To measure mass equilibrium swelling ratios (Q), 20 µL droplets of hydrogel solutions were pipetted onto a flat Teflon surface and crosslinked under 365 nm UV light for 2 seconds at a dose rate of 90 mW/cm². The samples were swelled in serum-free M199 for 24 hours and weighed for swollen weight (Ws). Afterward, the samples were washed in de-ionized $H_2O$ overnight to remove M199 components from the hydrogel, frozen in –80° C. for 2 hours and lyophilized. The dried polymer was weighed for dry weight ($W_D$) and mass equilibrium swelling ratio was calculated as per equation:

$$\text{Mass equilibrium swelling ratio } Q = W_S/W_D$$

To measure the shear modulus of the hydrogels, 660 µL of the above solutions were pipetted into 2.1 cm diameter Teflon wells. The resulting hydrogels were swollen in 1×PBS for 24 hours before test samples of 8 mm diameter were retrieved using a hole punch with 3 replicates per condition. The samples were tested using an Ares-LS2 rheometer (TA Instruments, New Castle, Del.). A 20-gram force was applied to the samples and a strain sweep test at 10 Hz fixed frequency was performed from 0.1 to 20% strain. Complex shear modulus of each sample was the average of measurements taken at 10 Hz, 1-10% strain.

Hydrogel Array Stencils

Hydrogel array stencils were fabricated using conventional photolithography techniques and were formed from two separate elastomer parts: a 200 µm thick sheet of microwells and a 1 mm thick base. Briefly, silicon master molds were fabricated by spin coating a 200 µm layer of SU-8 100 (Microchem, Newton, Mass.) onto a silicon wafer (University Wafer, Boston Mass.). Arrayed 1 mm diameter posts of photoresist were defined using a photomask (Imagesetter, Madison, Wis.). Poly(dimethylsiloxanel (PDMS) was prepared by combining Sylgard PDMS solution with crosslinking solution (Dow Corning, Midland, Mich.) at a 10:1 volume ratio. The solution was degassed under a vacuum for 45 minutes, poured onto the silicon master mold and crosslinked on a hot plate for 4 hours at 85° C., forming the 200 µm thick sheet of microwells that penetrated the entire thickness of the sheet. To form the base of the hydrogel array stencil, the PDMS solution was poured between glass slides to form sheets of 1 mm thickness and cured on a hot plate for 4 hours at 85° C. Both stencil components were cleaned in hexanes (Fisher) by soxhlet extraction and placed in vacuo to remove residual solvent. The completed PDMS stencil was formed by laying the 200 µm thick sheet on top of the 1 mm thick base.

Forming PEG Hydrogel Arrays

Hydrogel spot solutions were added to the PDMS stencil wells as 0.4 µl droplets (FIG. 14). To solidify the hydrogel spots before desiccation, the droplets were crosslinked under 365 nm UV light for 2 seconds at a dose rate of 90 mW/cm² after every 5 droplets were patterned. A photomask was used to prevent multiple UV exposures to previously cured spots.

Once all spots were crosslinked under UV light, a 1 mm-thick background hydrogel slab was formed by curing 230 µl background hydrogel solution under 365 nm UV light for 2 seconds at a dose rate of 9D mW/cm² between a flat 1 mm thick PDMS sheet and a 1"×1" glass slide. After removing the PDMS sheet only, an additional 30 µl background hydrogel solution was pipetted on top of the hydrogel slab to anchor the spots to the background slab upon crosslinking. The background slab, still attached to the glass slide, was placed on top of the cured hydrogel spots and the entire array was cured for an additional 2 seconds under 365 nm UV light at a 90 mW/cm² dose rate. The hydrogel array was removed from the PDMS stencil and submerged in medium in a 6-well cell culture plate. The completed arrays were secured to the bottom of the wells by using magnets to hold the glass slides in place.

Peptide Incorporation into Hydrogel Array Spots

To verify controllable peptide incorporation into the hydrogel array spots, hydrogel solutions of 12% w/v total polymer consisting of PEGNB, a 2× molar excess of 3.4 kDa PEG dithiol to PEGNB, and PEGNB-CRGDS (SEQ ID NO:2) such that 0, 0.01, 0.1, 1, 2 mM concentrations of CRGDS (SEQ ID NO:2) were patterned into the array using the above procedure. The background hydrogels were compositionally identical to the spots but were lacking CRGDS (SEQ ID NO:2). CRGDS (SEQ ID NO:2) concentration was verified by labeling the N-terminus of the peptide with fluorescein. Briefly, the arrays were treated with 3 µM solution of fluorescein-conjugated sulfodichlorophenol ester (Invitrogen, Grand Island, N.Y.) in PBS, incubated for overnight, then rinsed for 24 hours in new PBS. The fluorescently labeled spots were photographed using a Nikon TI Eclipse microscope, and fluorescence intensity was quantified using ImageJ software.

HUVEC Viability, Tubulogenesis and Proliferation in 3D Hydrogel Arrays

During hydrogel array fabrication, hydrogel spots contained HUVECs at a density of 2×10⁷ cells/mL. The concentration of CRGDS adhesion peptide (SEQ ID NO:2) was adjusted to 0, 0.25, 0.5, 1.0 and 2.0 mM through the addition of PEGNB-CRGDS (SEQ ID NO:2), with the total pendant peptide concentration in all hydrogel spots maintained at 2 mM by adding PEGNB-CRDGS (SEQ ID NO:2). Total polymer percent weight was varied between 4.2, 5 and 7% w/v in the hydrogel spots and 4, 6 and 8% w/v in the backgrounds, with low percent weight hydrogel spots corresponding to low weight percent backgrounds and high percent weight hydrogel spots corresponding to high percent weight backgrounds. During viability experiments, arrays of encapsulated cells were cultured for 48 hours in growth medium alone or with 10 μM SU5416 (Sigma Aldrich), a known inhibitor of VEGFR2 signaling. Medium was replaced 24 hours after encapsulation. After 48 hours of culture, the arrays were washed with serum-free M199 and stained with 5 μM Cell Tracker Green (Invitrogen) for 45 minutes in M199. After 15 minutes of staining, the staining solution was supplemented with Hoechst nuclear stain (Invitrogen) to achieve a final concentration of 10 μg/mL. After staining, the arrays were washed with serum free M199 and incubated for 30 minutes in growth medium containing 2 μM ethidium homodimer (Invitrogen). The arrays were then washed with 1×PBS and fixed for 30 minutes in 10% buffered formalin (Fisher). The arrays were soaked in 1×PBS overnight and photographed using a Nikon TE300 fluorescence microscope within 48 hours of fixation. Viability was quantified by dividing the number of live cell nuclei by total nuclei in the post.

During proliferation and tubulogenesis experiments, the arrays of encapsulated cells were cultured in growth medium alone or with 10 μM SU5416 for 24 hours only. Afterward, the cells were incubated for 5 hours in growth medium with 20 μM 5-ethynyl-2'-deoxyuridine (EdU) (Invitrogen) as a proliferation marker and, if appropriate, 10 μM SU5416. Afterward, the arrays were stained with Cell Tracker Green in the same manner as the viability assay, but without Hoechst nuclear stain or ethidium homodimer. The arrays were washed with 1×PBS, fixed for 30 minutes in 10% buffered formalin and stained using the Click-iT EdU 594 proliferation kit (Invitrogen). The staining procedure was slightly modified from the manufacturer's instructions, as Alexa Fluor® 594 was diluted to half the recommended concentration. The arrays were soaked in 1×PBS overnight and photographed using a Nikon TE300 fluorescence microscope. Proliferation was quantified by counting the number of EdU-positive cells and dividing by the total number of nuclei in the post. Tubulogenesis was quantified by manually measuring total capillary-like structure (CLS) length in each post as labeled by Cell Tracker Green. To obtain confocal microscopy images, the hydrogel arrays were mounted in Prolong Gold antifade solution (Invitrogen) and photographed on a Nikon A1R-Si confocal microscope.

HUVEC Proliferation with VEGFR2 Inhibition

HUVECs were plated in tissue culture polystyrene (TCPS) 24-well plates at a density of $5.0 \times 10^4$ cells/cm$^2$. The cells were grown in growth medium alone or with 10 μM SU5416 for 24 hours. Afterward, the medium was changed to fresh growth medium with or without 10 μM SU5416 and 20 μM EdU. After 5 hours of incubation, the cells were fixed in 10% buffered formalin for 30 minutes and stained using the Click-iT EdU 488 proliferation kit (Invitrogen). The staining procedure was slightly modified from the manufacturer's instructions, as Alexa Fluor® 488 was diluted to half the recommended concentration. The cells were photographed using a Nikon TE300 fluorescence microscope and proliferation was quantified via by counting nuclei staining positive for EdU and normalizing the number to total nuclei.

HUVEC Tubulogenesis in MATRIGEL®

HUVECs were suspended in growth factor-reduced MATRIGEL® (BD Biosciences, San Jose, Calif.) at a density of $2 \times 10^7$ cells/mL. A 200 μm thick PDMS sheet of microwells was placed on top of a glass slide and the MATRIGEL®-cell suspension was pipetted as 0.4 μl droplets into the microwells. These arrays of MATRIGEL® "spots" were incubated at 37° C. for 30 minutes and covered in growth medium alone or with 10 μM SU5416. After 48 hours of culture, the arrays were stained with Cell Tracker Green in the same manner as in the PEG hydrogel viability assay, but without Hoechst nuclear stain or ethidium homodimer. The arrays were washed with 1×PBS and fixed for 30 minutes in 10% buffered formalin. A green fluorescence and phase contrast z-stack image of each spot was taken at 48 hours after encapsulation using a Nikon TI Eclipse microscope. Total CLS length in each individual spot was quantified manually.

HUVEC Tubulogenesis in Confined Hydrogels

HUVEC tubulogenesis in 10 μl volume hydrogels was qualitatively assessed to determine the effects of hydrogel confinement on CLS formation. Here, the hydrogels contained 4.2% w/v total polymer, a 2× molar excess of cell-degradable crosslinking peptide to PEGNB, and PEGNB-CRGDS (SEQ ID NO:2) to establish a CRGDS (SEQ ID NO:2) concentration of 2 mM. The HUVECs used in these hydrogels were treated with 1 μM Cell Tracker Green prior to trypsinization. Briefly, the cells were washed with serum-free M199 and stained with Cell Tracker Green for 45 minutes in M199. After staining, the cells were washed with serum-free M199 and incubated for 30 minutes in growth medium. After trypsinization, the cells were resuspended in the PEG hydrogel solution at a density of at $2 \times 10^7$ cells/mL.

To observe tubulogenesis in confined hydrogels, the cell-containing hydrogel solutions were pipetted as 10 μl droplets on the bottoms of 48-well TCPS plates. The droplets were crosslinked under 365 nm UV light for 2 seconds at a dose rate of 90 mW/cm$^2$. To ensure that the droplets remained stationary throughout the duration of the experiment, 90 μl of 8% w/v background hydrogel solution was added around the solidified hydrogels and crosslinked under 365 nm UV light for 2 seconds at a dose rate of 90 mW/cm$^2$. The encapsulated cells were incubated in growth medium with 10 μM SU5416 for 24 hours. A green fluorescence and phase contrast z-stack image of each sample was taken using a Nikon TI Eclipse microscope 24 hours after encapsulation.

To observe tubulogenesis in unconfined hydrogels, the cell-containing hydrogel solutions were pipetted as 10 μl droplets on a flat PDMS sheet and crosslinked under 365 nm UV light for 2 seconds at a dose rate of 90 mW/cm$^2$. The resulting hydrogels were transferred to a 24-well TCPS plate containing growth medium with 10 μM SU5416. After 24 hours of incubation, the gels were pinned using a 24-well culture inserts (Becton Dickinson, Franklin Lakes, N.J.) to keep them stationary during photography. A green fluorescence and phase contrast z-stack image of each sample was taken using a Nikon T1 Eclipse microscope 24 hours after encapsulation.

Statistical Analysis

Statistical differences were calculated using the two-sided Student's T-test assuming equal variances. Statistical significance was denoted as $p<0.05$.

Results

Hydrogel Equilibrium Swelling Ratio and Complex Shear Modulus.

Figure 15A:
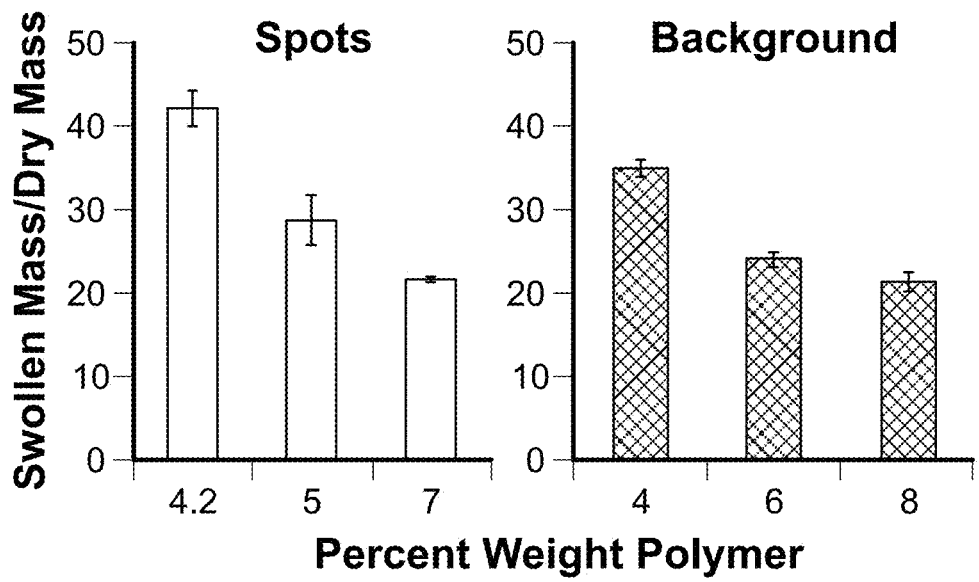
FIGS. 15A-15D depict characterization of mechanical properties and pendant peptide incorporation into the hydrogel arrays of Example 4.
Figure 15B:
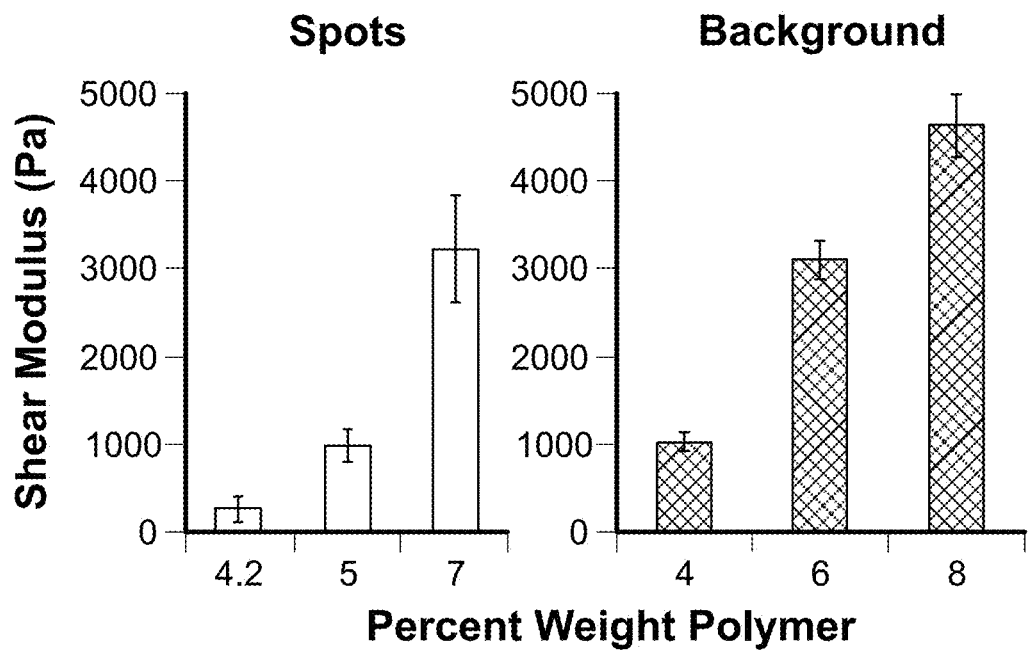

The swelling properties and moduli of degradable hydrogel spots and inert background hydrogels were controlled by adjusting the percent weight of polymer included in the formulations. Hydrogel spot formulations containing 4.2, 5 and 7% w/v polymer had mass equilibrium swelling ratios of 42.1±2.1, 28.7±2.9, and 21.6±0.4, respectively. Background hydrogels containing 4, 6, and 8% w/v polymer had equilibrium swelling ratios of 34.9±0.9, 23.9±0.9 and 21.3±1.1, respectively (FIG. 15A). The background hydrogels were designed to have similar but slightly lower swelling ratios than the hydrogel spots in order to provide a more stable substrate for anchoring the spots during culture. Hydrogel spot formulations containing 4.2, 5 and 7% w/v polymer had moduli of 260±140 Pa, 980±210 Pa and 3220±610 Pa, respectively. Therefore, the 4.2, 5 and 7% w/v hydrogels were designated as "low", "medium" and "high" modulus hydrogels for the duration of the study to clarify the presentation of the data. The moduli of the 4, 6 and 8% w/v background hydrogels were 1040±100 Pa, 3100±220 Pa and 4160±350 Pa, respectively (FIG. 15B). The range of moduli chosen for this Example (~260-3220 Pa) spans a wide range of tissues, including soft tissues such as the vocal fold lamina, as well as normal breast tissue and cancerous breast tissue, two examples of tissues that differ in mechanical properties as well as extent of vascularization.

Hydrogel Array Fabrication and Peptide Incorporation

Figure 15C:
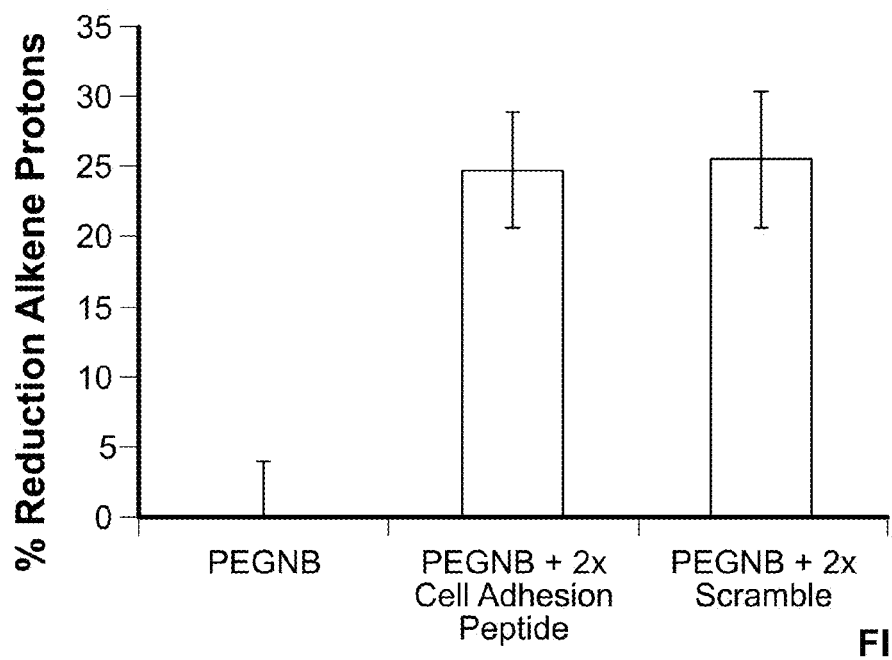

The hydrogel constructs in this Example consisted of arrayed PEG hydrogel spots that contained controlled concentrations of CRGDS (SEQ ID NO:2). Functionalization efficiency of PEGNB with CRGDS (SEQ ID NO:2) or CRDGS (SEQ ID NO:32) was confirmed using NMR. The adhesion peptides CRGDS (SEQ ID NO:2) and CRDGS (SEQ ID NO:32) were reacted to PEGNB at 2× molar excess to decorate, on average, two of the eight arms of the PEGNB molecule with the cell adhesion peptides. The presence of CRGDS (SEQ ID NO:2) at 2× molar excess to PEGNB resulted in a 24.8±4.1% reduction of alkene protons present on the PEG molecule, and the presence of CRDGS (SEQ ID NO:32) at 2× molar excess to PEGNB resulted in a 25.7±4.9% reduction of alkene protons (FIG. 15C). This indicates that approximately two of the eight available norbornene groups on a given PEGNB molecule were coupled to the adhesion peptide, as expected.

Figure 15D:
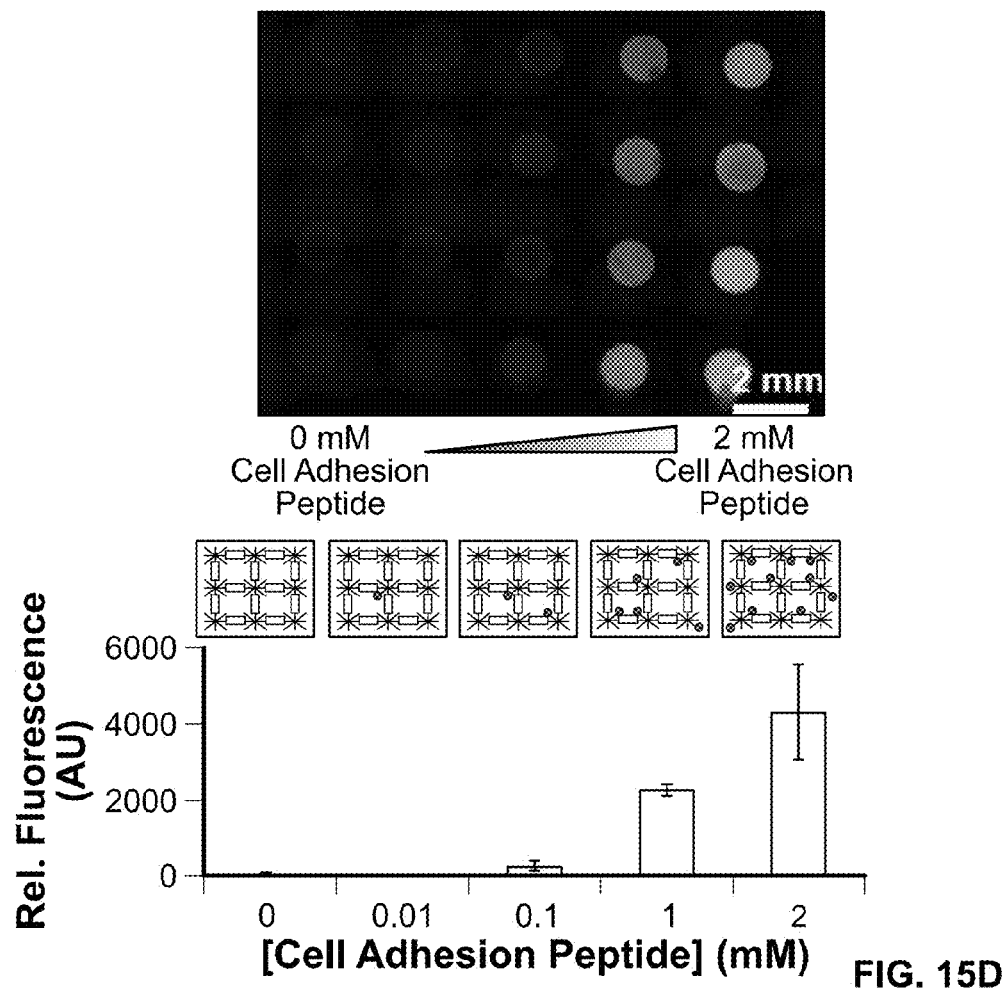

Incorporation of peptide-decorated PEG macromers into the hydrogel arrays was also visualized using fluorescein staining via a sulfodichlorophenol-ester linkage. Fluorescent signals from the array were directly proportional to the amount of peptide added to the arrayed hydrogel spots. Additionally, only background fluorescence was detected between the spots, indicating that the peptides were present in the spots only (FIG. 15D). These results demonstrate that PEG hydrogels can be used to provide synthetic control over incorporation of thiol-containing ligands, in this case, the cell adhesion peptide CRGDS (SEQ ID NO:2).

Three-Dimensional Cell Viability in PEG Hydrogel Arrays

Figure 16A:
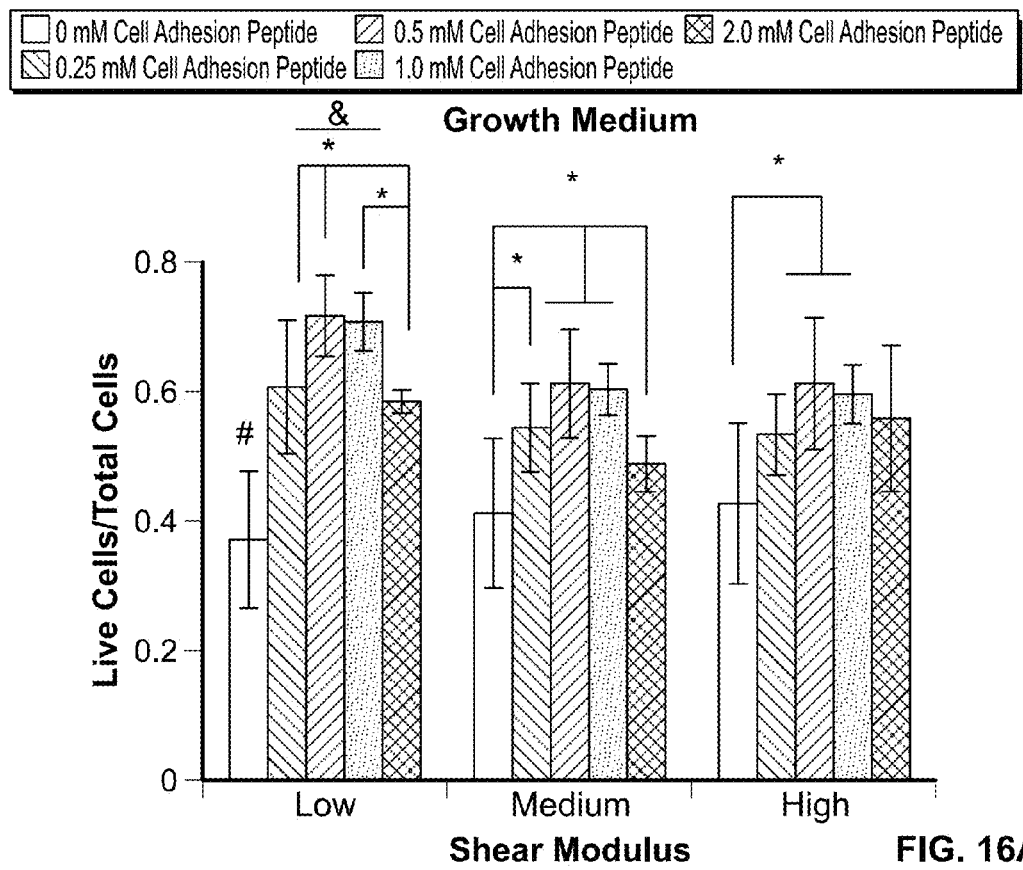
FIGS. 16A-16C depict the viability of HUVECs encapsulated inside the hydrogel array spots.

The viability of encapsulated HUVECs were then quantified to verify that the cells withstood the encapsulation and array patterning processes, and to evaluate the effects of adhesion ligand density and stiffness on maintaining cell survival. Cell viability generally increased with increasing CRGDS (SEQ ID NO:2), and high modulus conditions suppressed viability. In all conditions HUVECs displayed viability levels at or above 40% of total encapsulated cells, with the lowest viability levels observed in spots containing 0 mM CRGDS (SEQ ID NO:2). Increased CRGDS (SEQ ID NO:2) concentration increased viability in all modulus conditions, with maximal viability observed at 0.5 and 1.0 mM CRGDS (SEQ ID NO:2). At these CRGDS (SEQ ID NO:2) concentrations, low modulus hydrogels promoted the highest viability levels compared to equivalent CRGDS (SEQ ID NO:2) concentrations in higher modulus conditions. However, viability in the low and medium modulus hydrogels decreased when CRGDS (SEQ ID NO:2) concentration was increased from 1.0 to 2.0 mM. This decrease did not reduce viability below levels observed at 0 mM CRGDS (SEQ ID NO:2) concentrations, indicating that the 2.0 mM CRGDS (SEQ ID NO:2) concentration was suboptimal, but not detrimental, to HUVEC viability relative to non-adhesive conditions. In the high modulus condition, there was no significant decrease in HUVEC viability at 2.0 mM when compared to 1.0 mM CRGDS (SEQ ID NO:2), suggesting a role of stiffness in maintaining viability in the presence of high CRGDS (SEQ ID NO:2) concentrations (FIG. 16A).

Three-Dimensional Cell Proliferation in PEG Hydrogel Arrays

Figure 17A:
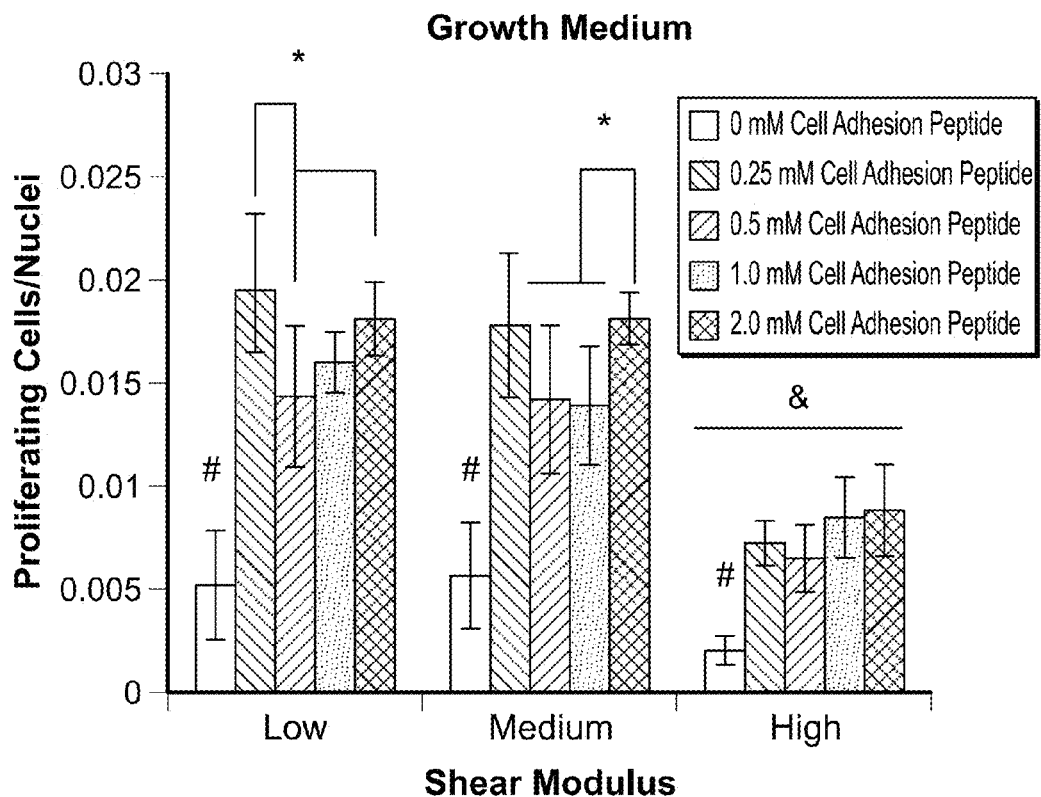
FIGS. 17A-17D depict proliferation of HUVECs encapsulated inside the hydrogel array spots.
Figure 17B:
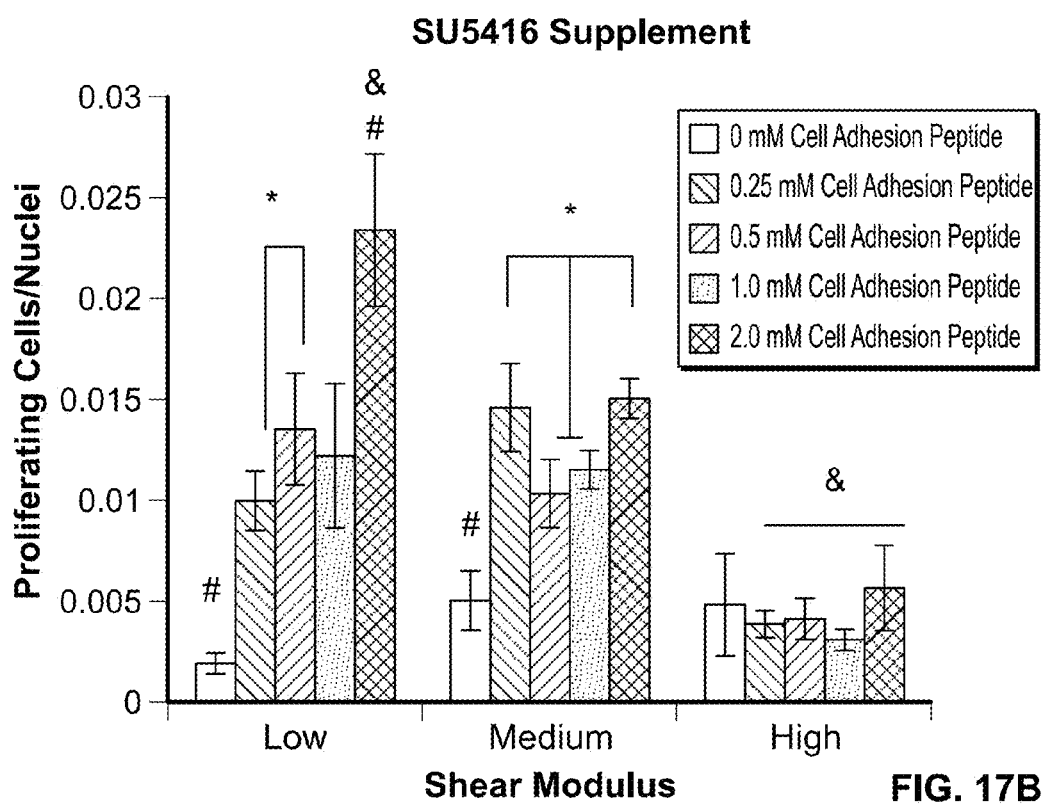
Figure 17C:
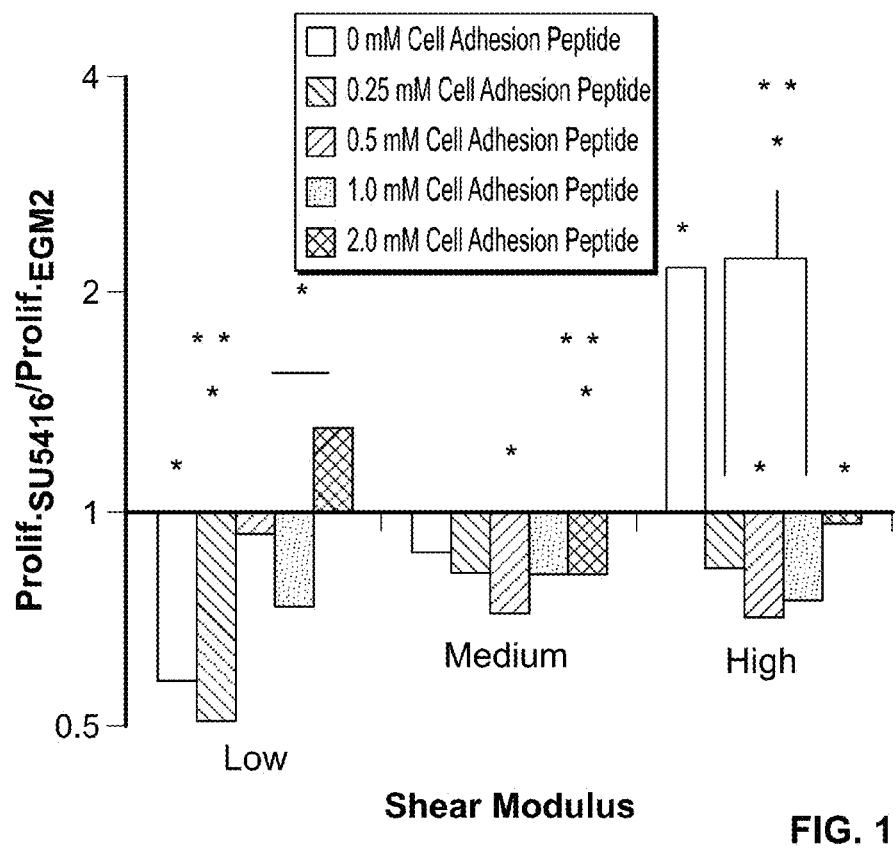
Figure 17D:
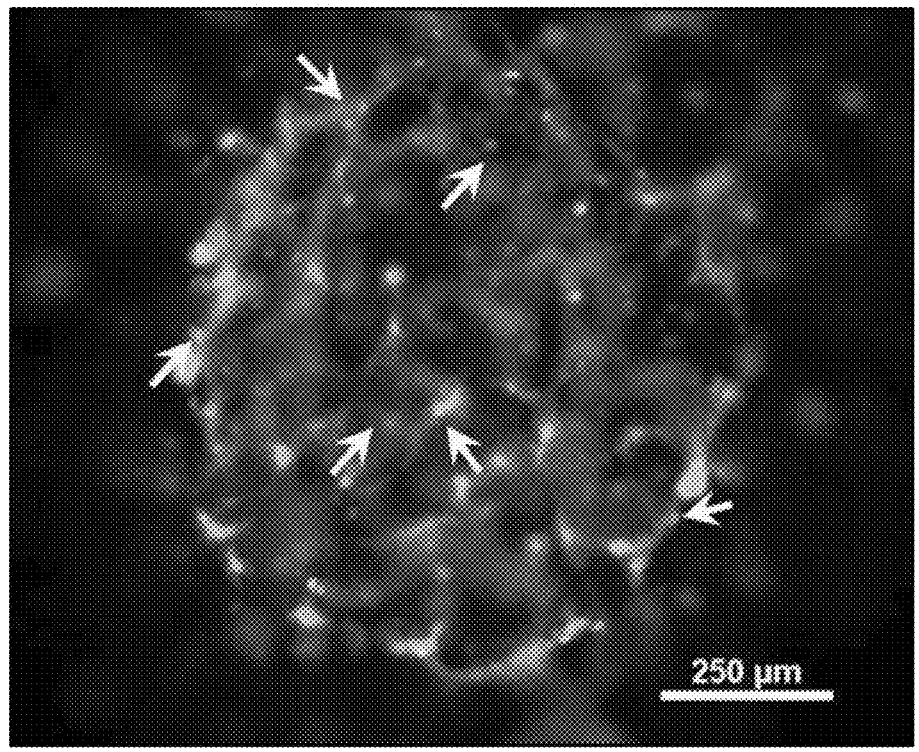

The effects of cell adhesion and stiffness on proliferation were determined by labeling and quantifying the nuclei of encapsulated HUVECs in S-phase. In all modulus conditions, the addition of CRGDS (SEQ ID NO:2) to the hydrogel increased cell proliferation beyond spots lacking CRGDS (SEQ ID NO:2) (FIG. 17A). Proliferation did not follow a monotonic trend with increasing CRGDS (SEQ ID NO:2) and high modulus hydrogels suppressed proliferation relative to low and medium modulus conditions. In particular, proliferation in the low and medium modulus conditions displayed a biphasic response to increasing CRGDS (SEQ ID NO:2). Proliferation was lower at 0.5 mM CRGDS (SEQ ID NO:2) compared to 0.25 and 2.0 mM CRGDS (SEQ ID NO:2) in the low modulus condition and lower at both 0.5 and 1.0 mM CRGDS (SEQ ID NO:2) compared to 2.0 mM CRGDS (SEQ ID NO:2) in the medium modulus condition. In the high modulus condition, the overall proliferation rate was significantly lower than proliferation rates in the low and medium modulus conditions, and no significant differences in proliferation existed between any conditions containing CRGDS (SEQ ID NO:2). In addition to ECM effects on proliferation, it is qualitatively noted that a majority of proliferating cells co-localized with multicellular structures (FIG. 17D).

Three-Dimensional Tubulogenesis in PEG Hydrogel Arrays

Figure 18A:
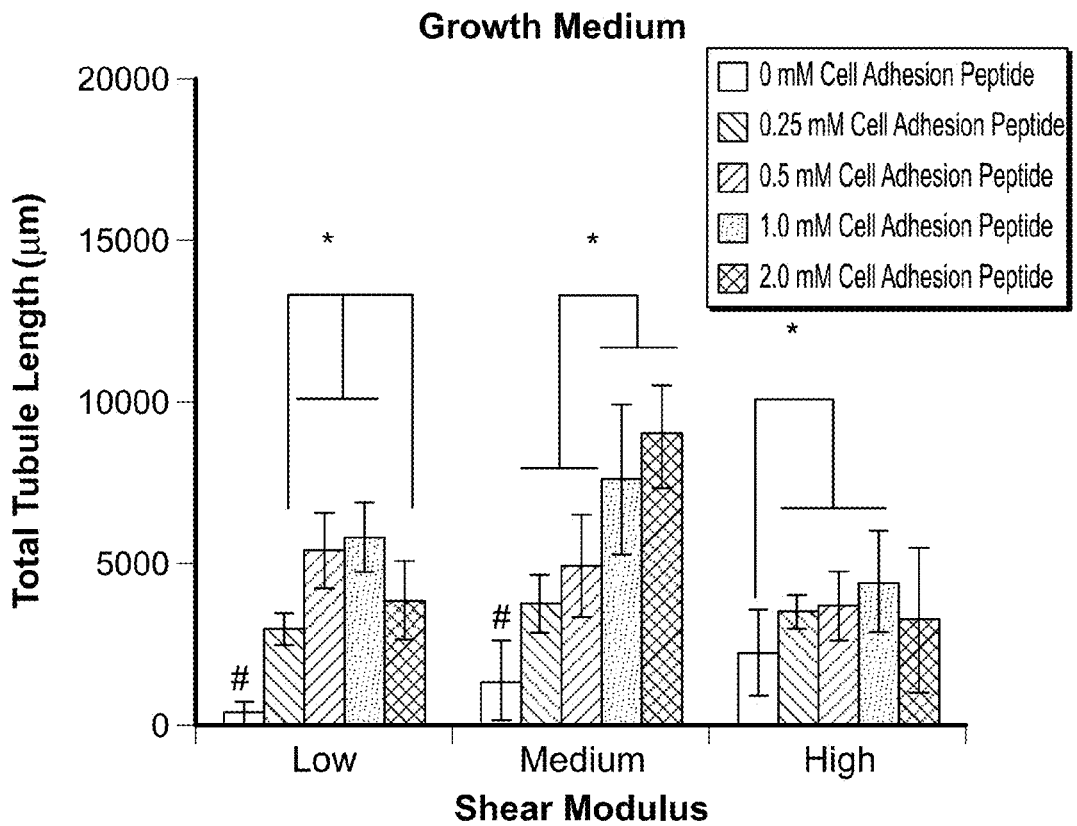
FIGS. 18A-18D depict tubulogenesis of HUVECs encapsulated inside the hydrogel array spots.

Cell adhesion and hydrogel stiffness significantly influenced total capillary-like structure (CLS) length in the hydrogel spots, and optimal levels of CRGDS (SEQ ID NO:2) concentration and modulus maximized CLS formation in the range of conditions tested. In all modulus conditions, CLS formation was rare in the absence of CRGDS (SEQ ID NO:2). In the low modulus condition, CLS formation increased with increasing CRGDS (SEQ ID NO:2) up to 1.0 mM concentration and decreased at 2.0 mM CRGDS (SEQ ID NO:2). This trend was not observed in the medium modulus condition whereas formation remained elevated at 2.0 mM CRGDS (SEQ ID NO:2) (FIG. 18A). In the high modulus condition, CLS formation was significantly increased at 0.25, 0.5 and 1.0 mM CRGDS (SEQ ID NO:2) compared to the condition lacking CRGDS (SEQ ID NO:2), but this increase was no longer significant at 2.0 mM CRGDS (SEQ ID NO:2). CLS formation at 0.5 mM CRGDS (SEQ ID NO:2) was significantly lower in the high modulus condition compared the low modulus condition and CLS formation at 1.0 and 2.0 mM CRGDS (SEQ ID NO:2) was lower in the high modulus condition compared to the medium modulus condition, indicating that high stiffness interfered with CLS formation in these hydrogels. Taken together, these results suggest that tubulogenesis increases with increasing CRGDS (SEQ ID NO:2), but the most significant increases were observed in an optimal, medium modulus condition that was not excessively compliant or stiff.

HUVEC Viability, Proliferation and Tubulogenesis with VEGFR2 Inhibition

Figure 19A:
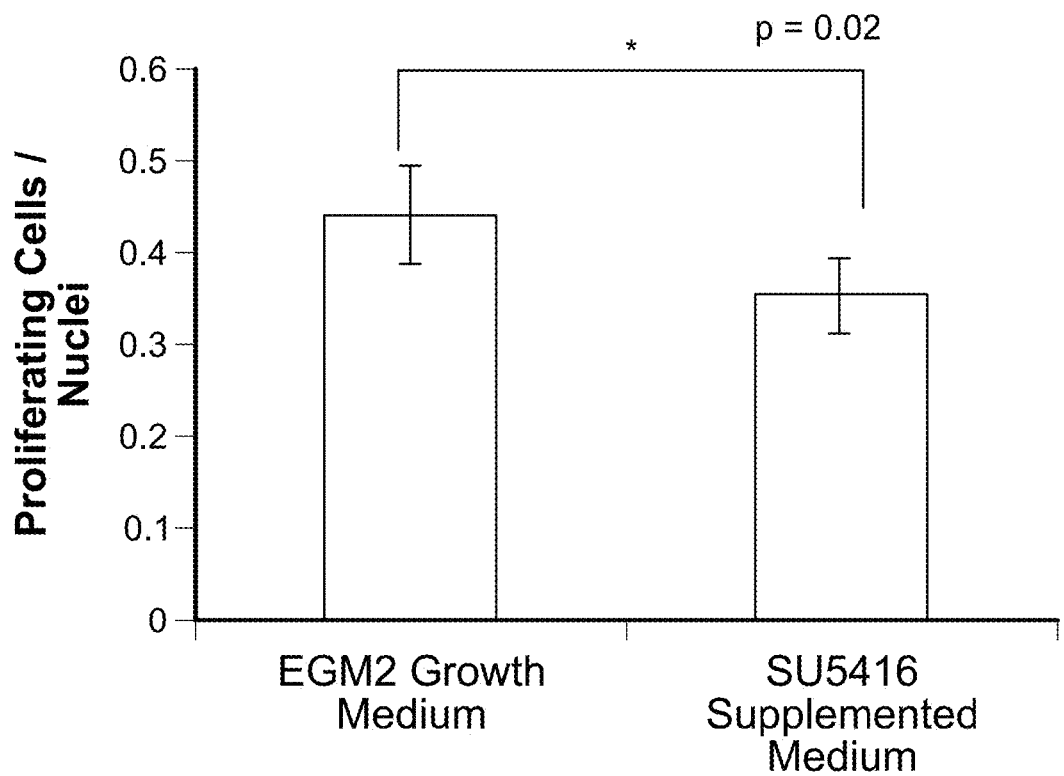
FIGS. 19A-19D depict effects of VEGFR2 inhibition in standard model systems.
Figure 19B:
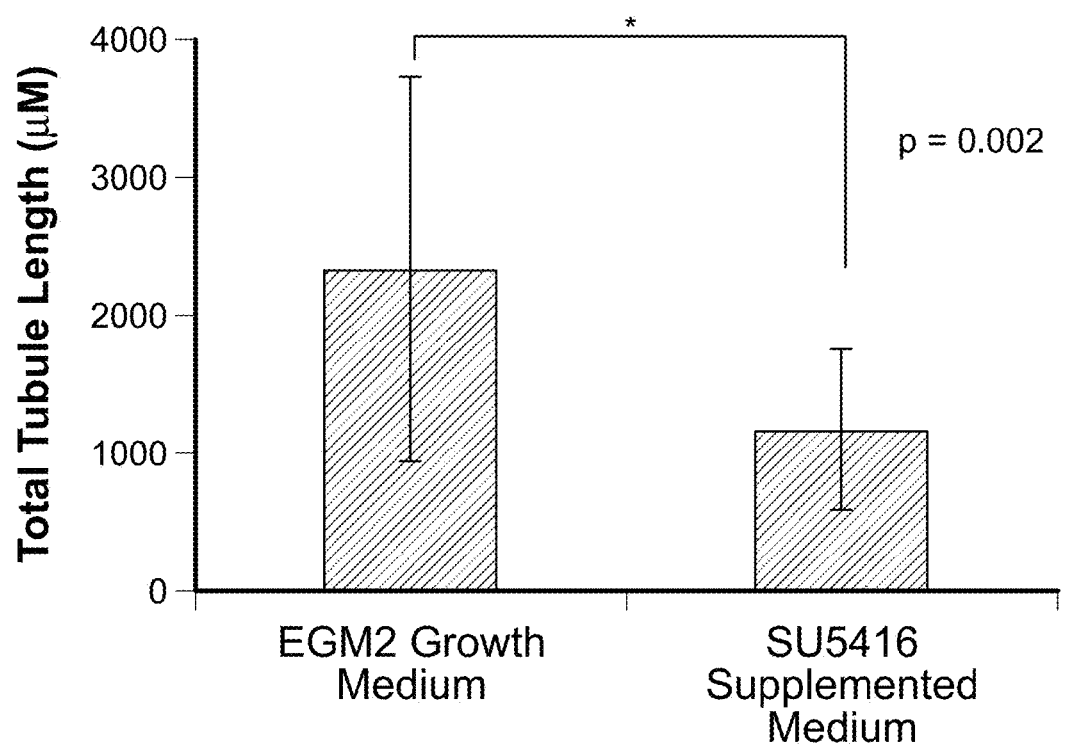
Figure 19C:
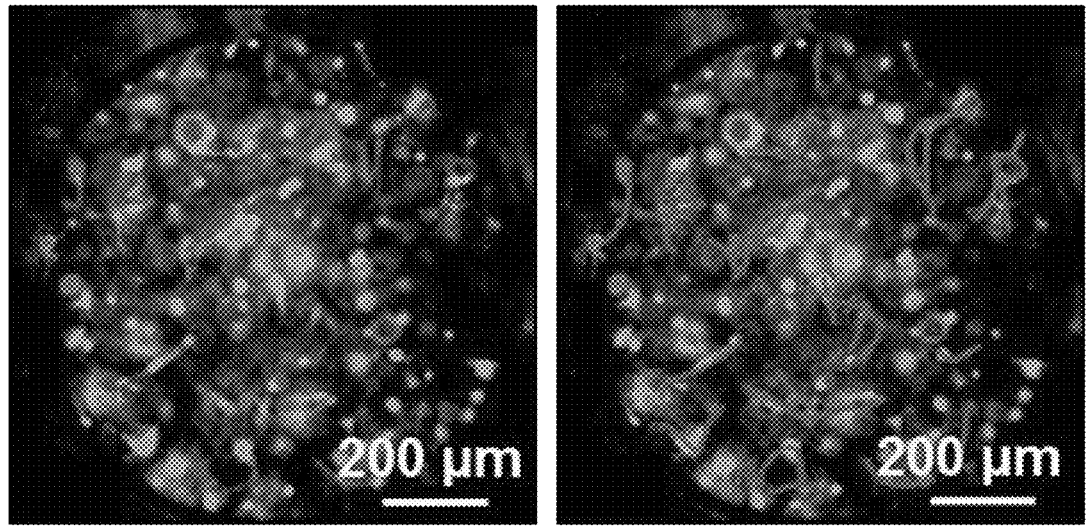
Figure 19D:
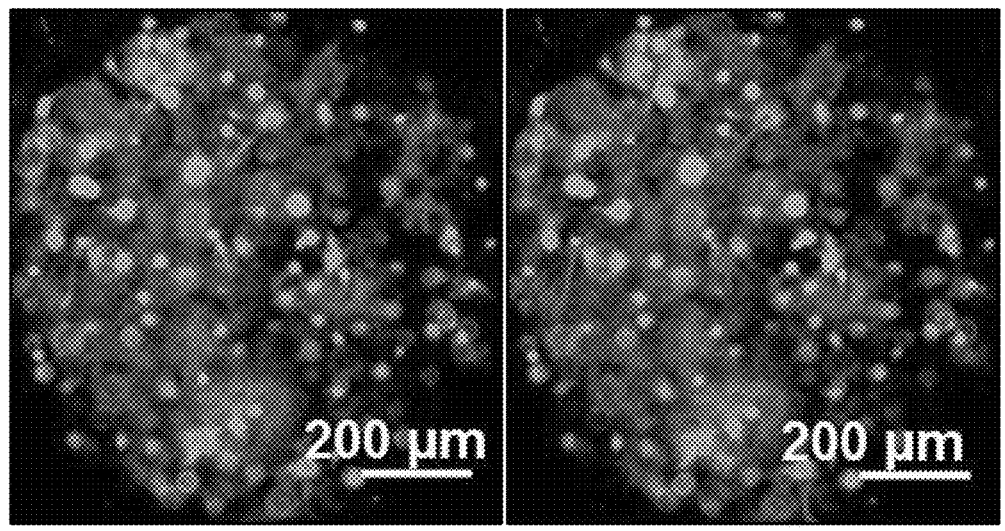

SU5416 is an inhibitor to VEGFR2 phosphorylation, and it was confirmed that inhibiting VEGF signaling by adding SU5416 to growth medium reduced HUVEC proliferation and tubulogenesis in traditional cell culture systems. Specifically, when HUVECs were seeded on tissue culture-treated polystyrene (TCPS) surfaces and assayed for proliferation, VEGFR2 inhibition resulted in a 20% decrease in proliferation compared to the growth medium control (FIG. 19A). When HUVECs were encapsulated in growth factor-reduced MATRIGEL® and assayed for CLS formation, VEGFR2 inhibition resulted in a 50% decrease in total tubule length compared to HUVECs incubated with growth medium only (FIGS. 19B & 19C).

Figure 16B:
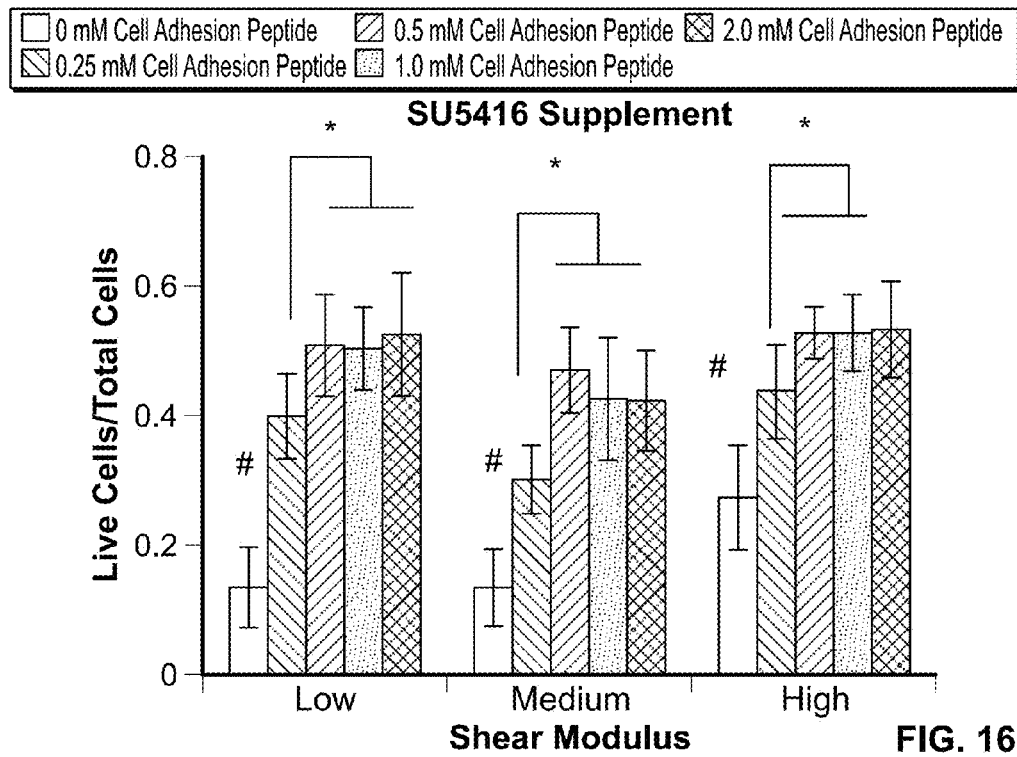
Figure 16C:
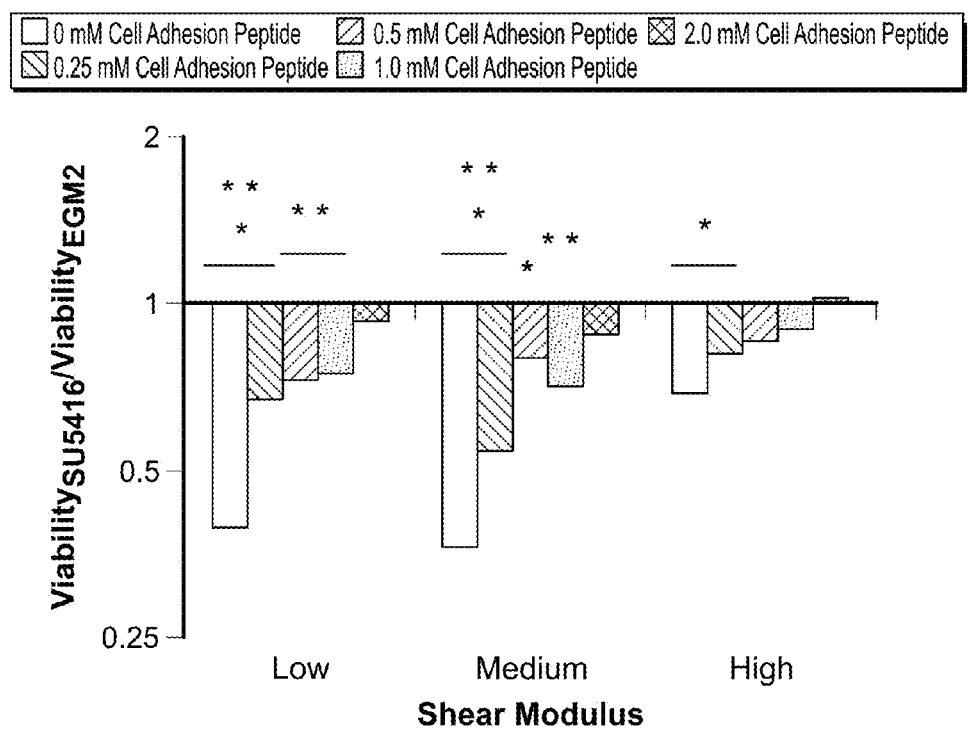

To explore the combinatorial roles of VEGFR2 signaling, controlled adhesion ligand density and stiffness in synthetic environments, HUVECs were encapsulated in hydrogel array spot treated with SU5416 and assayed for viability, proliferation and tubulogenesis. VEGFR2 inhibition significantly reduced cell viability in conditions that did not contain the CRGDS cell adhesion peptide (SEQ ID NO:2) (FIG. 16B). In all modulus conditions viability plateaued at 0.5 mM CRGDS (SEQ ID NO:2), indicating a limited role of CRGDS (SEQ ID NO:2) in maintaining cell viability when VEGFR2 was inhibited. This also suggests a synergistic interaction between VEGFR2 and integrin-mediated cell adhesion in the context of HUVEC viability. However, while normal VEGFR2 generally increased viability levels when compared to inhibited VEGFR2, the difference between normal VEGFR2 conditions and inhibited conditions decreased as the CRGDS (SEQ ID NO:2) concentration increased. In all modulus conditions, the reduction of viability with VEGFR2 inhibition was insignificant in spots containing 2 mM CRGDS (SEQ ID NO:2), indicating a diminishing role of VEGFR2 in modulating viability in the presence of increased CRGDS (SEQ ID NO:2). Additionally, the effect of VEGFR2 inhibition on viability was not significant in the high modulus condition when CRGDS (SEQ ID NO:2) concentration was at or above 0.5 mM CRGDS (SEQ ID NO:2) (FIG. 16C), indicating that the role of VEGFR2 was not as substantial in high modulus compared to lower modulus hydrogels.

HUVEC proliferation was decreased by VEGFR2 inhibition in a majority of hydrogel conditions. In the low and medium modulus conditions, all spots containing CRGDS (SEQ ID NO:2) had cell proliferation levels elevated beyond the 0 mM CRGDS (SEQ ID NO:2) condition, but proliferation levels did not increase with CRGDS (SEQ ID NO:2) in the high modulus condition (FIG. 17B). In the low modulus condition, VEGFR2 inhibition caused a significant decrease in proliferation levels at 0, 0.25 and 1 mM CRGDS (SEQ ID NO:2) conditions. Interestingly, proliferation levels in the 2 mM CRGDS (SEQ ID NO:2) condition increased significantly with VEGFR2 inhibition at low modulus. In the medium modulus condition, VEGFR2 inhibition caused significant proliferation decreases in the 0.5 and 2 mM CRGDS (SEQ ID NO:2) conditions and no increases in proliferation were observed. In the high modulus condition, significant decreases in proliferation with VEGFR2 inhibition were observed in all CRGDS (SEQ ID NO:2) concentrations except the 0 mM CRGDS (SEQ ID NO:2) condition. Though there was a significant increase in proliferation in the absence of CRGDS (SEQ ID NO:2), this proliferation level was less than proliferation levels observed with CRGDS (SEQ ID NO:2) in the other modulus conditions (FIG. 17C). Taken together, the surrounding context of synthetic hydrogel conditions dramatically changes HUVEC responses to VEGFR2 inhibition, as measured by cell proliferation.

Figure 18B:
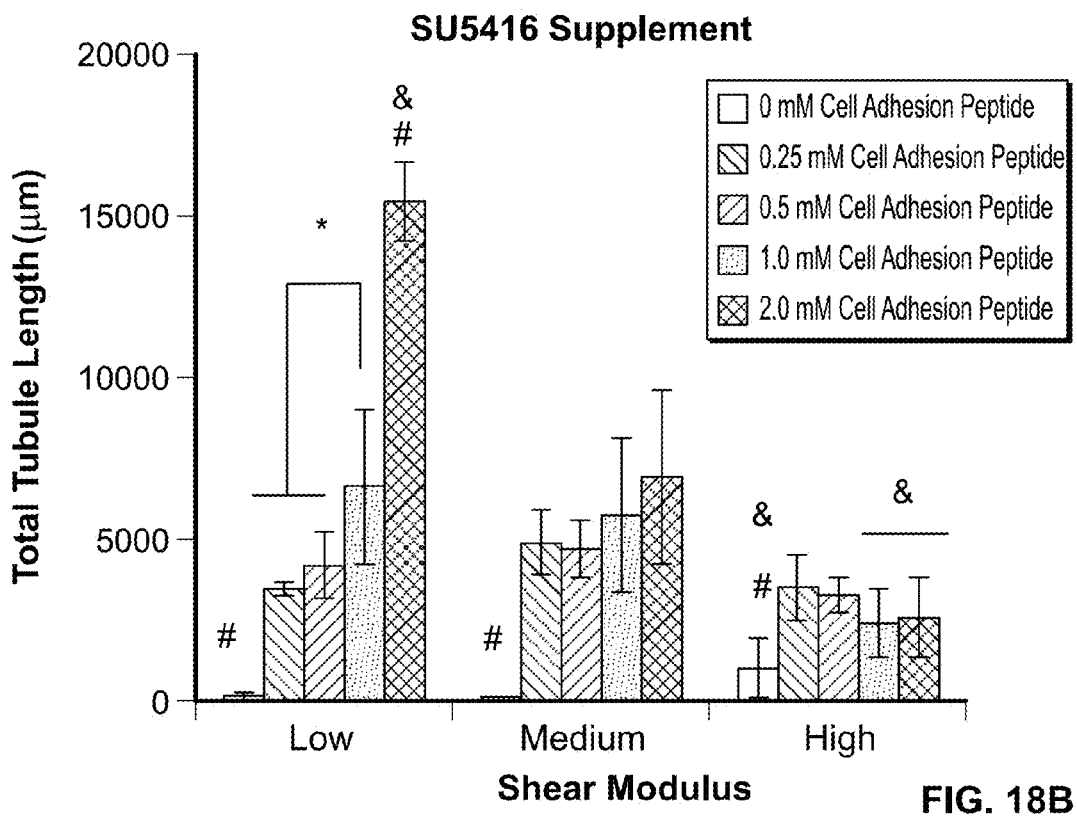
Figure 18C:
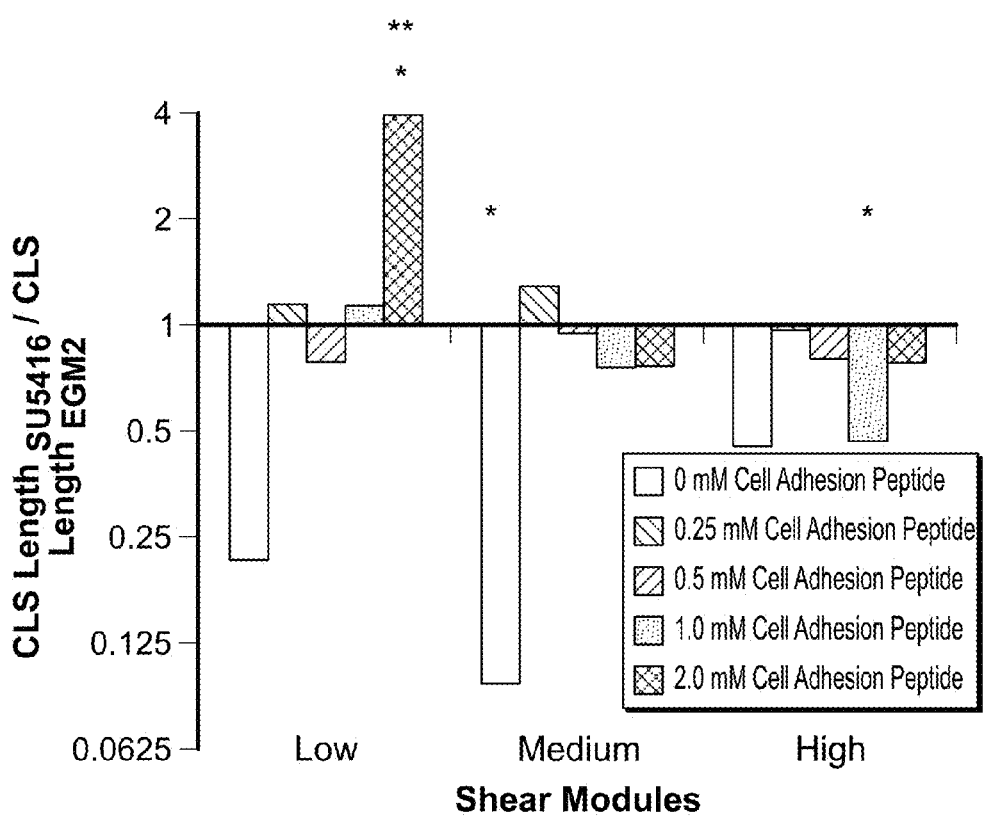
Figure 18D:
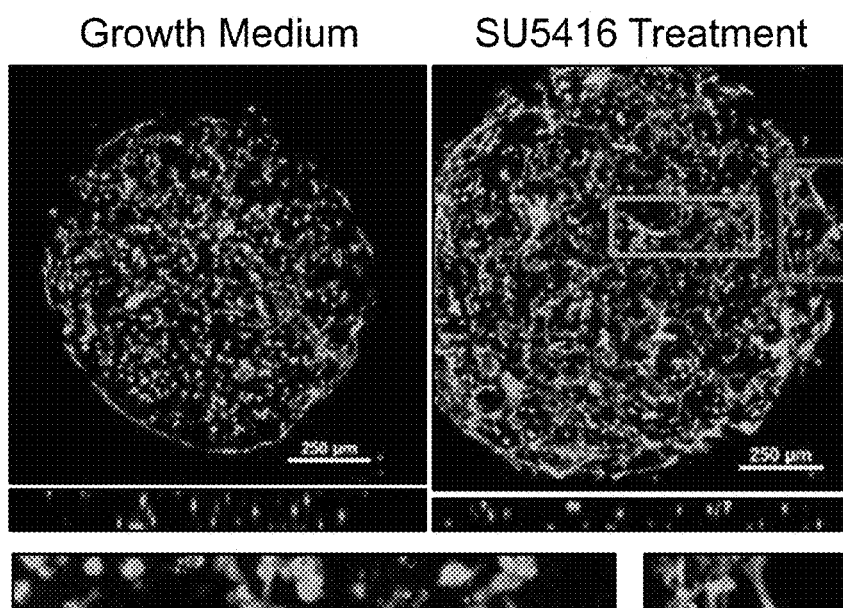
Figure 18D:
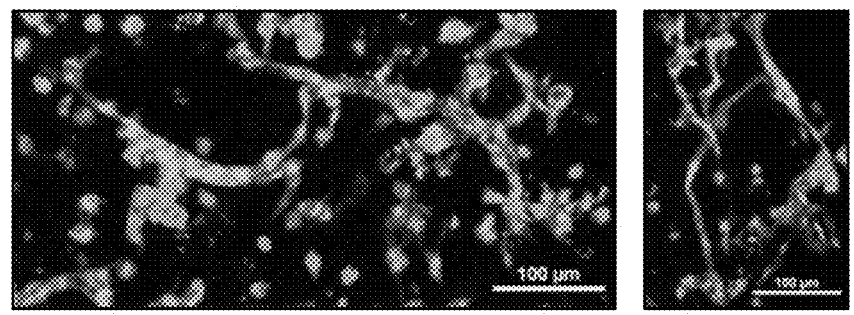

Inhibition of VEGFR2 with SU5416 also significantly changed the CRGDS (SEQ ID NO:2)-dependent trends in tubulogenesis in all the shear modulus conditions tested. In the low shear modulus conditions, CLS length increased monotonically with CRGDS (SEQ ID NO:2) concentration and increased dramatically at 2.0 mM CRGDS (FIGS. 18B-D). In the medium modulus condition, CLS length in spots containing CRGDS (SEQ ID NO:2) was significantly greater than lengths observed in the absence of CRGDS (SEQ ID NO:2). However, with VEGFR2 inhibition CLS length no longer changed with CRGDS (SEQ ID NO:2) concentration at medium modulus (FIG. 18B). In the high modulus condition, CLS length in all spots containing CRGDS (SEQ ID NO:2) was significantly greater than lengths observed in the absence of CRGDS (SEQ ID NO:2). Again, changing CRGDS (SEQ ID NO:2) concentrations did not change CLS length, and CLS lengths at all CRGDS (SEQ ID NO:2) concentrations were lower than CLS lengths in the medium modulus condition. Despite these changes in CLS trends, VEGFR2 inhibition did not cause significant changes to CLS length in most hydrogel conditions when compared to growth medium controls (FIG. 18C). Only 3 hydrogel conditions saw any significant effects with VEGFR2 inhibition: increased CLS length in low modulus, 2 mM CRGDS (SEQ ID NO:2) spots, decreased CLS length in medium modulus, 0 mM CRGDS (SEQ ID NO:2) spots, and decreased CLS length in high modulus, 1 mM CRGDS (SEQ ID NO:2) spots. These data are in stark contrast to VEGFR2 inhibition in MATRIGEL®, which resulted in a clear decrease in CLS length. Taken together, the data demonstrate that the context of surrounding hydrogel conditions dramatically changed HUVEC responses to VEGFR2 inhibition, as measured by HUVEC viability, proliferation, and tubulogenesis.

Tubulogenesis in Confined and Non-Confined Hydrogels

Figure 20B:
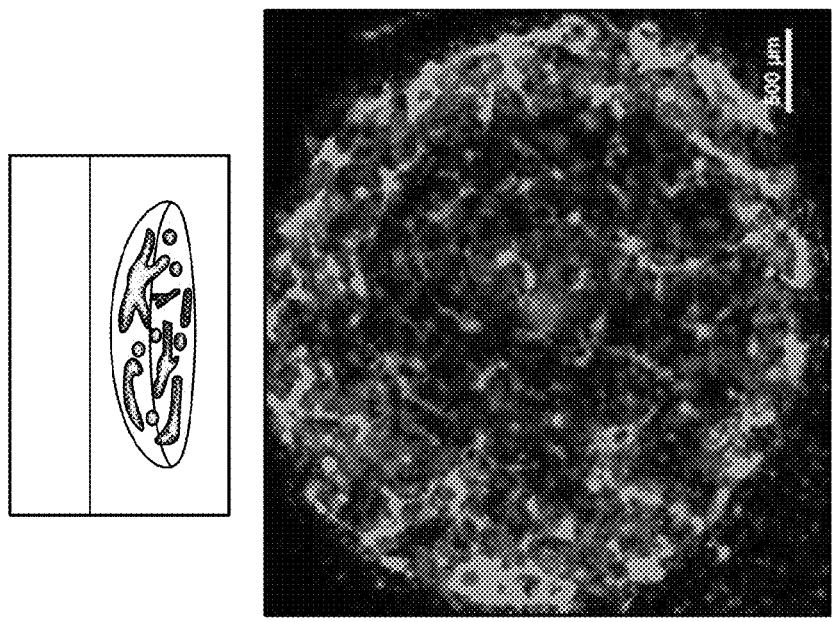
FIGS. 20A & 20B depict effects of cell encapsulation in confined hydrogels as analyzed in Example 4.
Figure 20A:
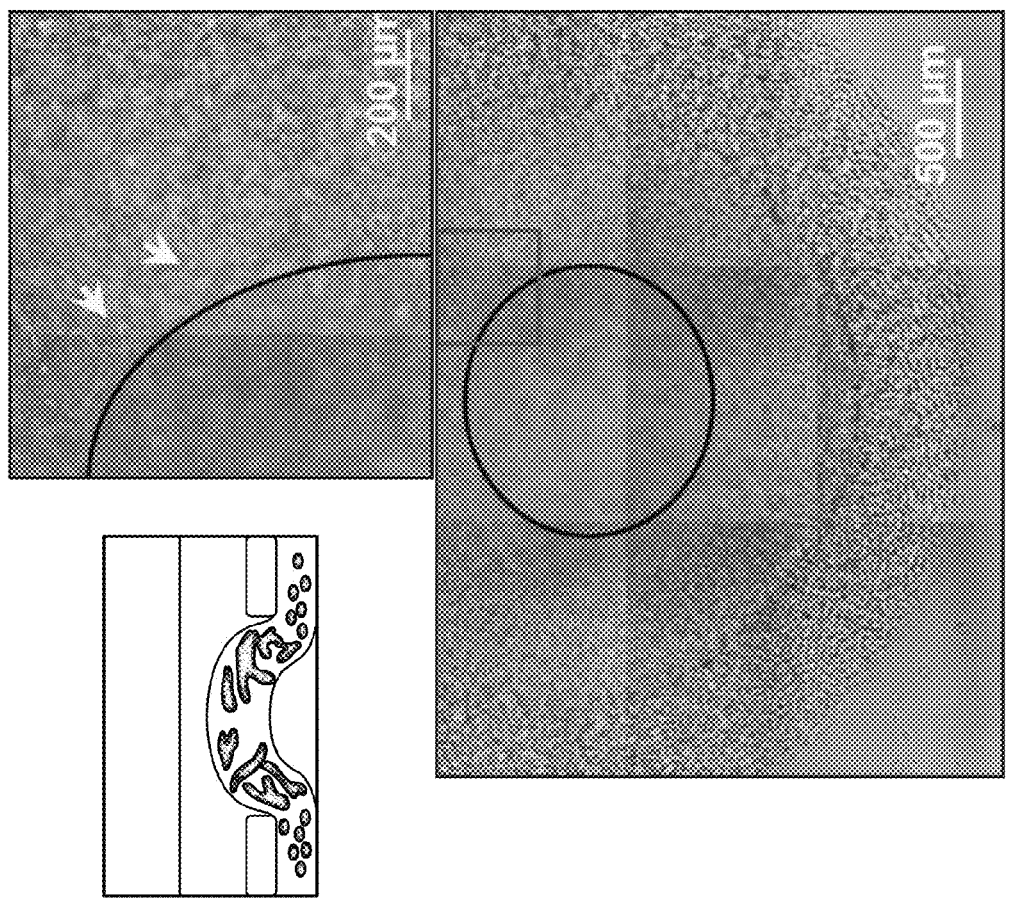

One distinction of the hydrogel array presented in this Example, when compared to many prior studies, is the degree to which the hydrogel is physically confined. For example, hydrogels formed in standard plastic well-plates, or elastomeric devices are typically highly confined, while the hydrogel spots in the array platform of the present disclosure are allowed to swell in concert with the background hydrogel. To further understand the comparison between CLS formation in hydrogels confined to rigid substrates versus unconfined hydrogels, the spatial distribution of CLS formation in hydrogels that were either confined to 48 well plates or detached from substrates was qualitatively observed and allowed to freely swell in medium. The confined hydrogels were susceptible to physical "buckling" during swelling, resulting in an out-of-focus area in the middle of the hydrogels (FIG. 20A). Buckling caused heterogeneity in CLS formation, with most of the structures forming around the edge of the buckled hydrogel area. In contrast, CLS formation in the non-confined hydrogels occurred homogeneously throughout the volume of the hydrogel (FIG. 20B), similar to the observations in hydrogel array spots in this Example. These observations suggest that cell encapsulation in confined hydrogels can introduce lurking variables upon swelling that significantly affect the outcome of a 3D neovascularization experiment.

Example 5

In this Example, PEG-hydrogel arrays were analyzed and varied to promote and optimize vascular network formation using human endothelial cells.

Figure 21:
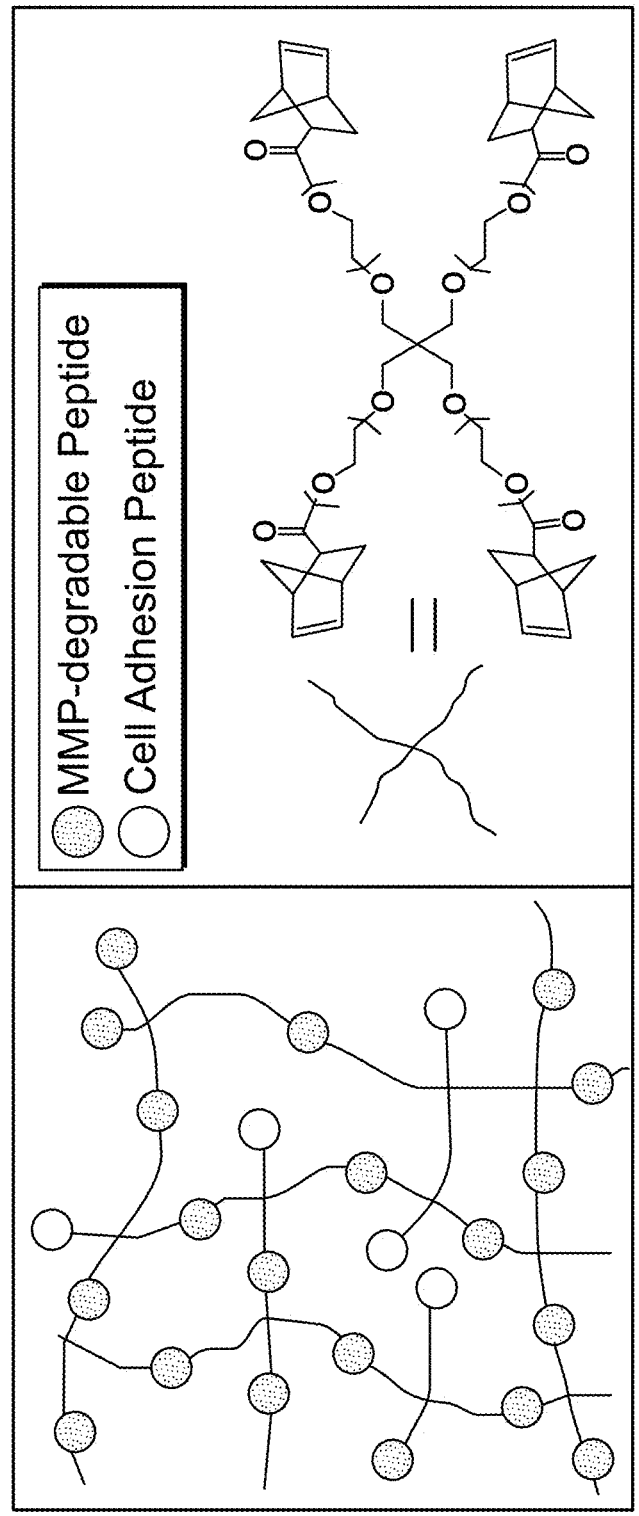
FIG. 21 depicts polyethylene glycol hydrogel arrays formed through thiol-ene photopolymerization as formed in Example 5.
Figure 22A:
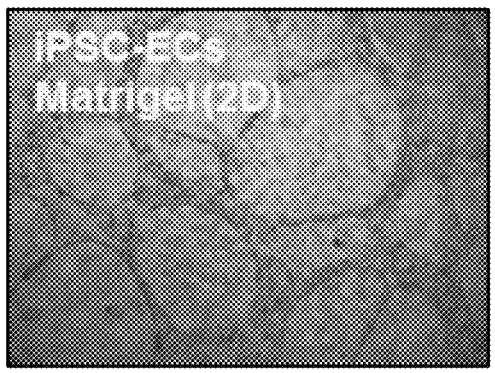
FIGS. 22A-22E depict endothelial cells in 2D and 3D hydrogel array cultures as analyzed in Example 5.
Figure 22B:
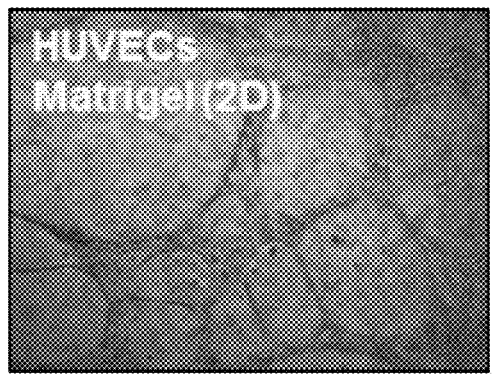
Figure 22C:
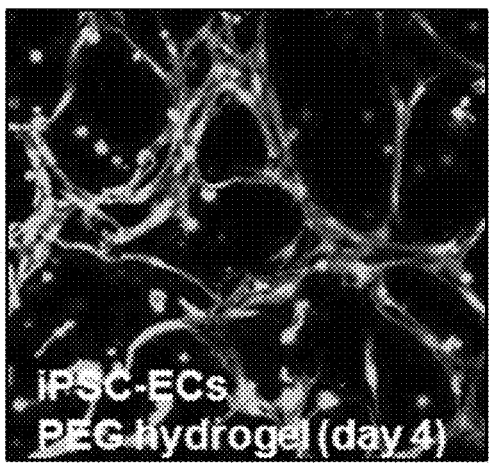
Figure 22D:
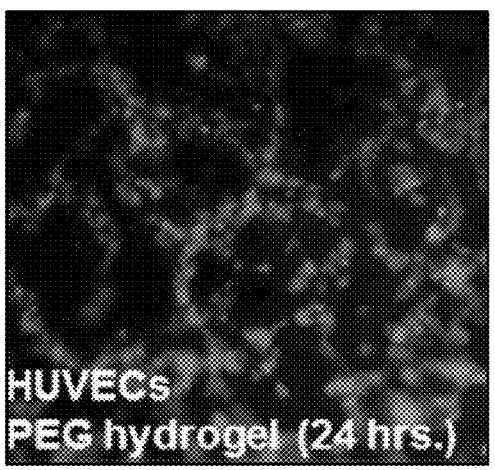
Figure 22E:
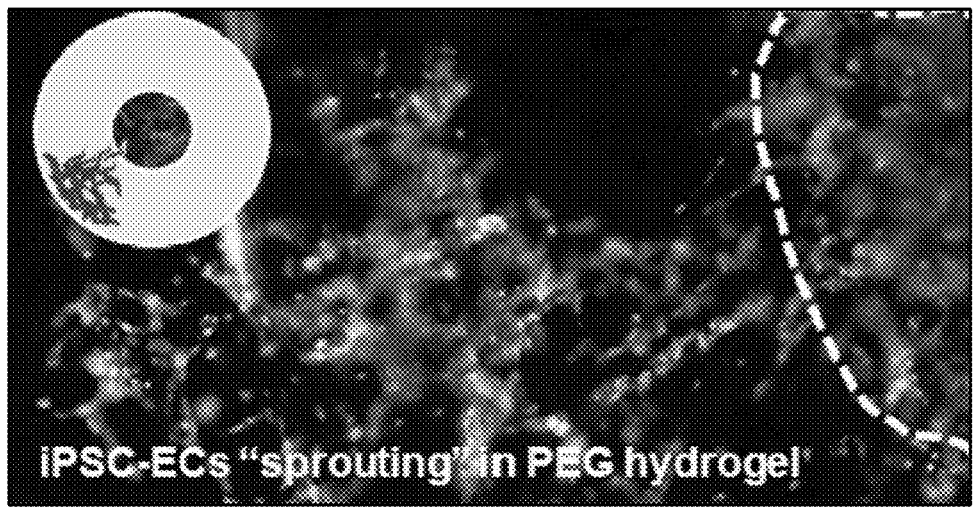

Poly(ethylene glycol) (PEG) hydrogel arrays were formed using thiol-ene photopolymerization to couple thiol-containing peptides with multiarm PEG molecules functionalized with terminal norbornene groups as described above. For 3D cell culture, hydrogel arrays were formed with matrix metalloproteinase (MMP)-degradable crosslinks to allow proteolytic remodeling and pendant RGD-containing peptides to promote adhesion (see FIG. 21 for peptides used in arrays).

Network formation and sprouting for human umbilical vein endothelial cells (HUVECs) or induced pluripotent stem cell-derived endothelial cells (iPSC-ECs) encapsulated in PEG hydrogels with varying RGD concentrations were analyzed to tune adhesion and MMP-crosslinking density to change mechanical properties. HUVECs and iPSC-ECs were encapsulated in PEG hydrogels at different cell densities: (1) $5-40\times10^6$ cells/mL to monitor network assembly or (2) $40\times10^6$ cells/mL to form high density clusters, which were then surrounded by a second hydrogel layer to investigate sprouting.

Figure 23C:
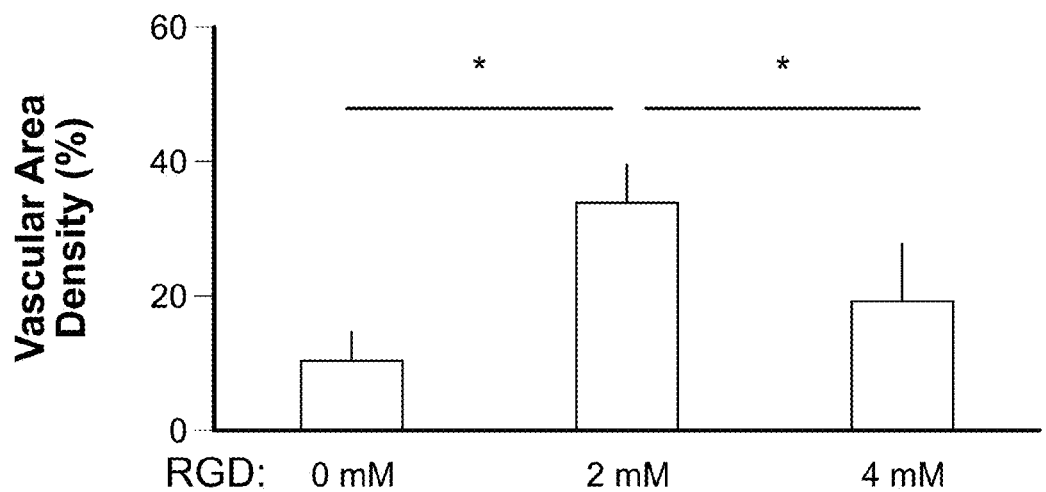
Figure 23D:
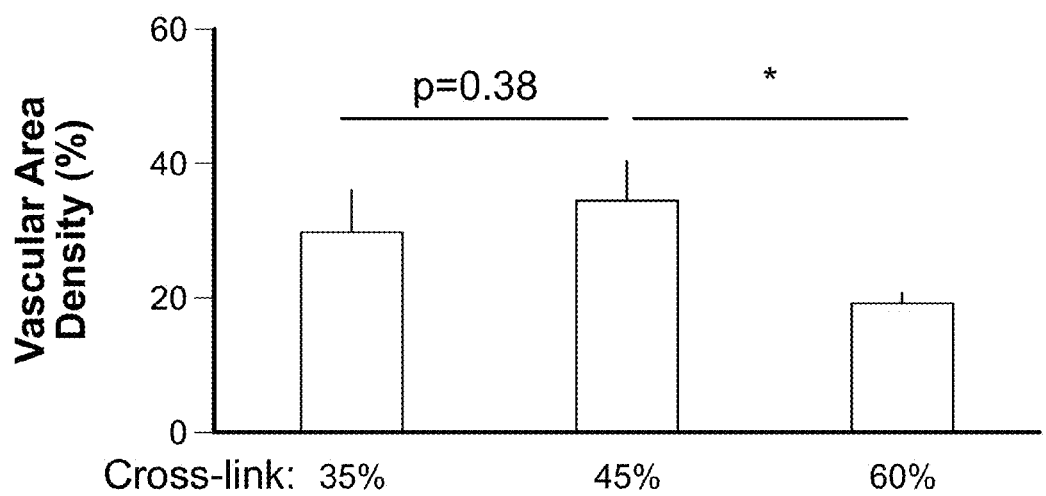
Figure 23E:
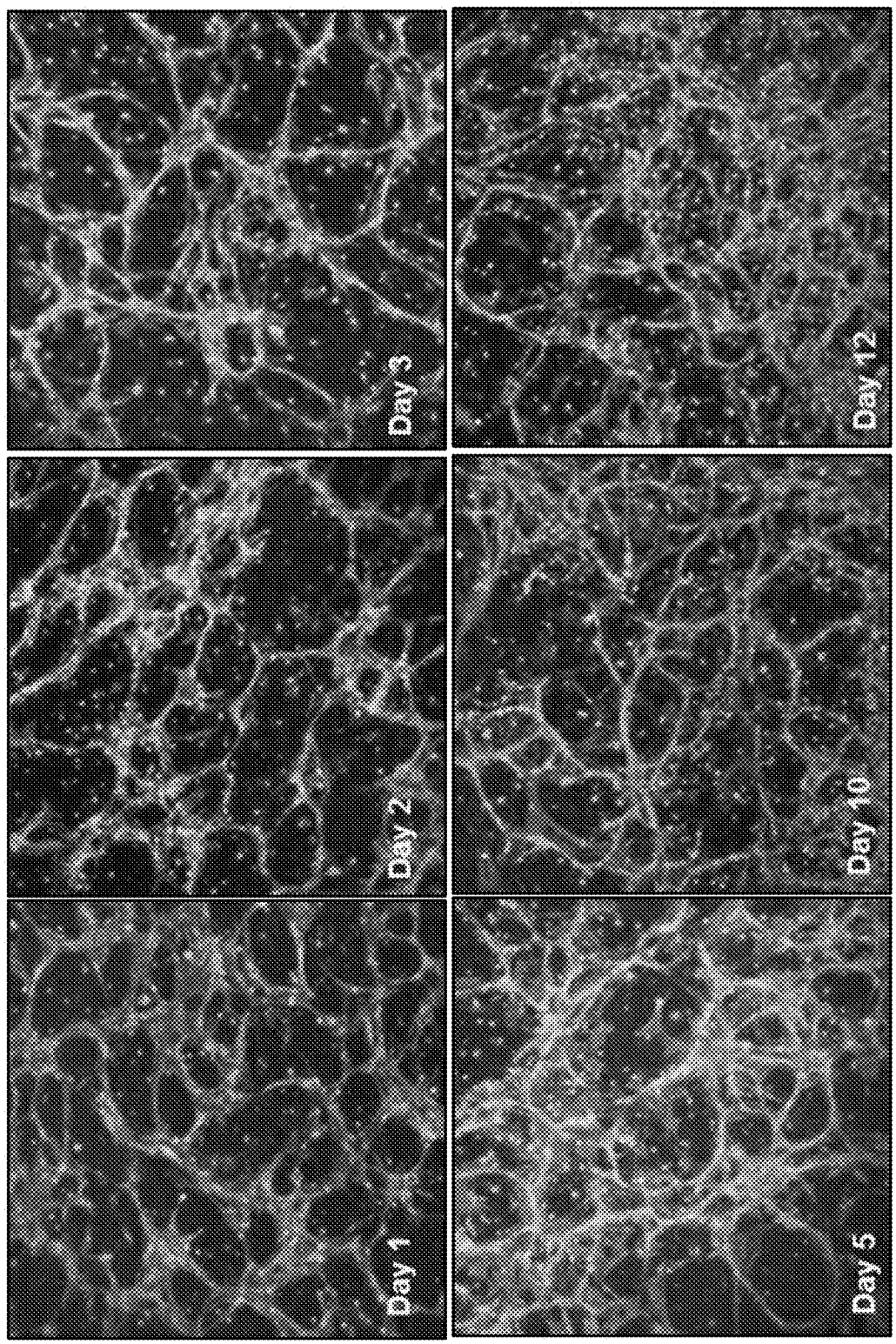

As shown in FIG. 22, the cells assembled into organized networks when encapsulated as dispersed cell suspensions in PEG hydrogel arrays while tube-like structures consistent with sprouting were observed when high density clusters were surrounded by cell-free PEG matrices. The networks were present until at least day 16. The extent of network formation was dependent on adhesion and crosslinking density (stiffness) and the stability of the resulting vascular structures was dependent on matrix properties (e.g., cell adhesion peptide concentration (hydrogel array stability/adhesion), crosslinking density (hydrogel array stiffness), culture media (e.g., incorporation of pericytes into networks), and the presence of support cells (see FIGS. 23A-23C)).

Example 6

In this Example, PEG-hydrogel array formulations with controlled stiffness and CRGDS (SEQ ID NO:2) were formed and analyzed for ability to support tubulogenesis within 24 hours of cell seeding.

Hydrogel solutions were created by combining 45 or 62 mg/mL 20 kDa 8-arm norbornene-functionalized PEG with 0 to 2 mM CRGDS (SEQ ID NO:2) adhesion peptide, additional CRDGS (SEQ ID NO:32) scrambled adhesion peptide to maintain a total pendant peptide concentration of 3 mM, KCGPQGIWGQCK (SEQ ID NO:27) crosslinking peptide at a 2× molar excess concentration to PEG, and 0.05% IRGACURE 2959 photoinitiator in phosphate buffered saline. The solutions were polymerized into hydrogels under UV light (90 mW/cm$^2$, 365 nm, 3 seconds). HUVECs were seeded at a density of $8.5\times10^4$ cells/cm$^2$ on hydrogel arrays and incubated in M199 supplemented with EGM2 growth supplement and photographed 1 hour after seeding and every hour up to 24 hours.

Figures 24A, 24B:
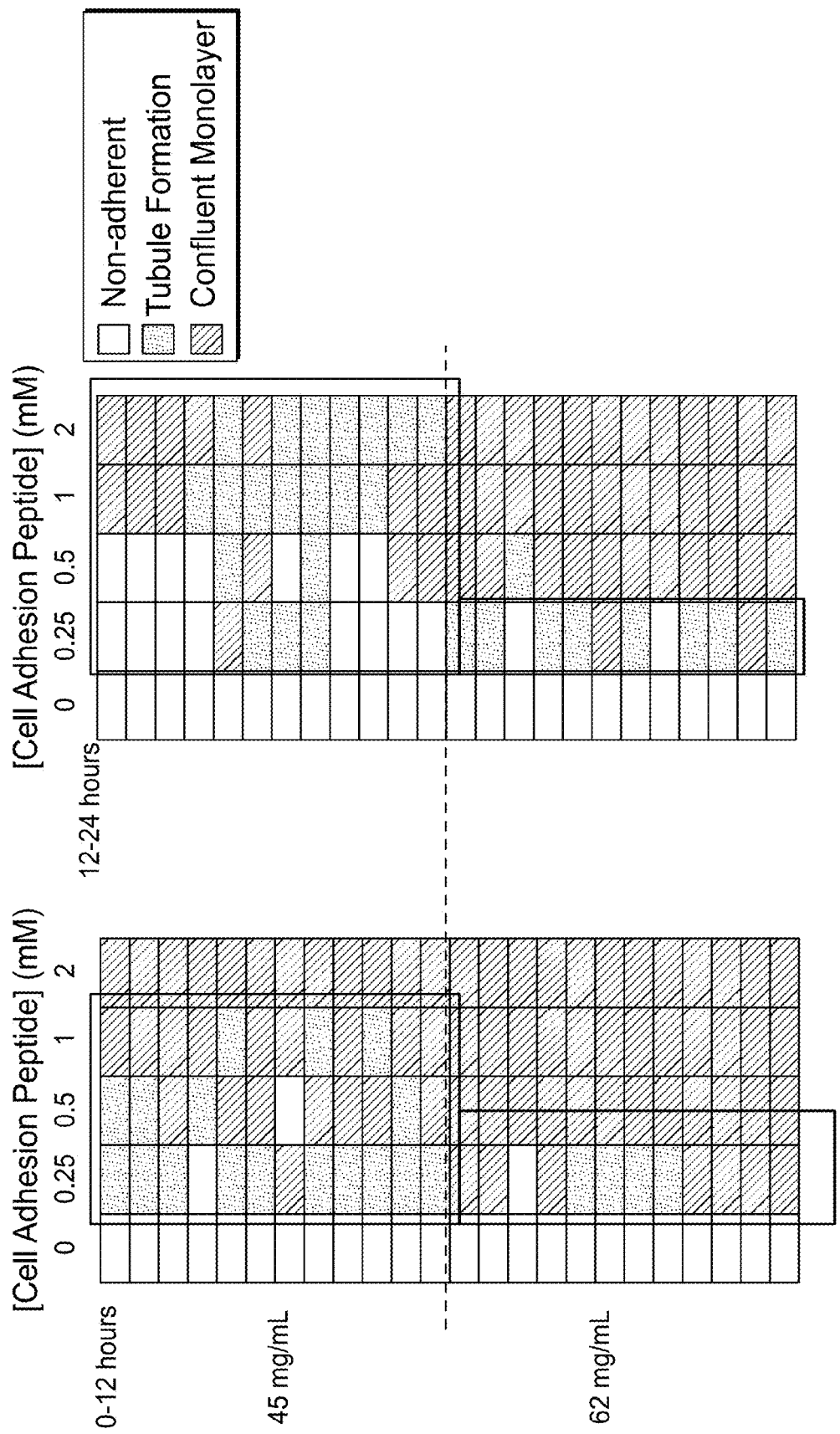
FIGS. 24A & 24B depict heat maps illustrating which PEG hydrogel surfaces support tubule network formation by HUVECs between 0 and 12 hours or 12 and 24 hours post-seeding when hydrogels present CRGDS (SEQ ID NO:2) adhesion peptide as analyzed in Example 6.
Figure 25A:
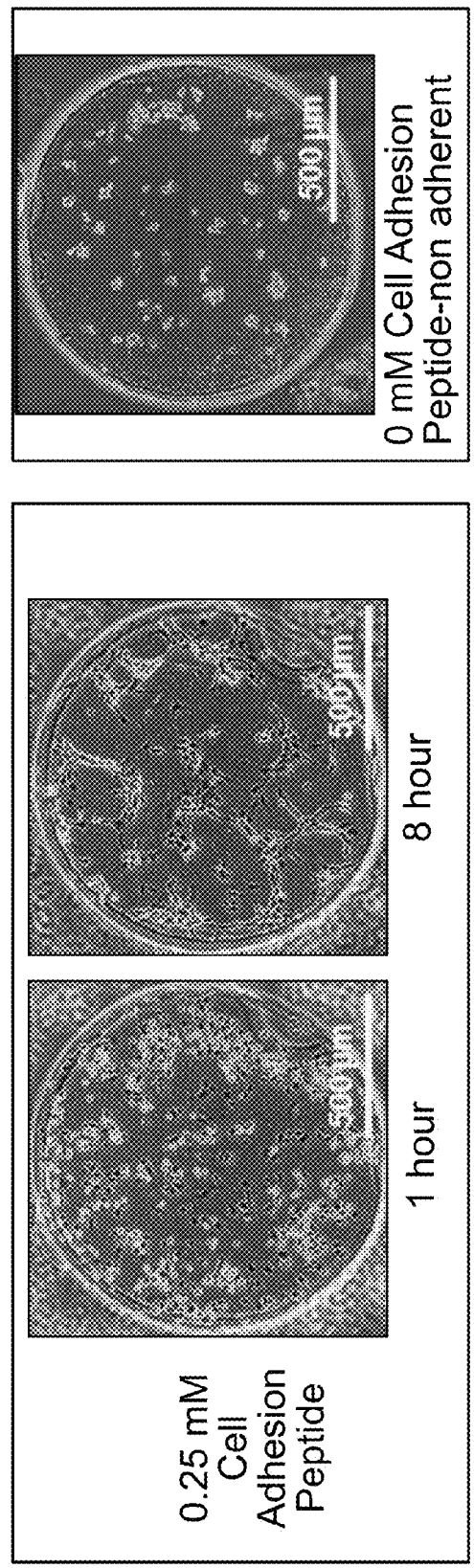
FIGS. 25A-25C depicts photographs of HUVECs forming tubule networks on PEG hydrogel surfaces, as well as examples of HUVECs failing to form tubule networks in Example 6.
Figure 25B:
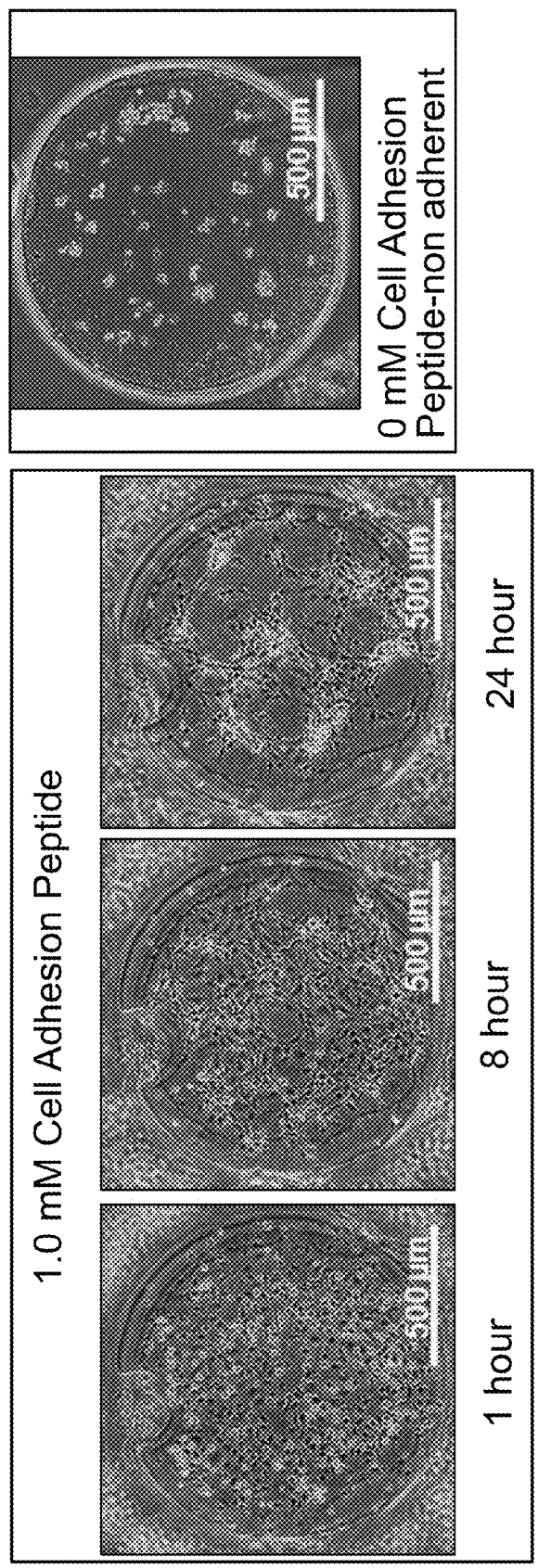
Figure 25C:
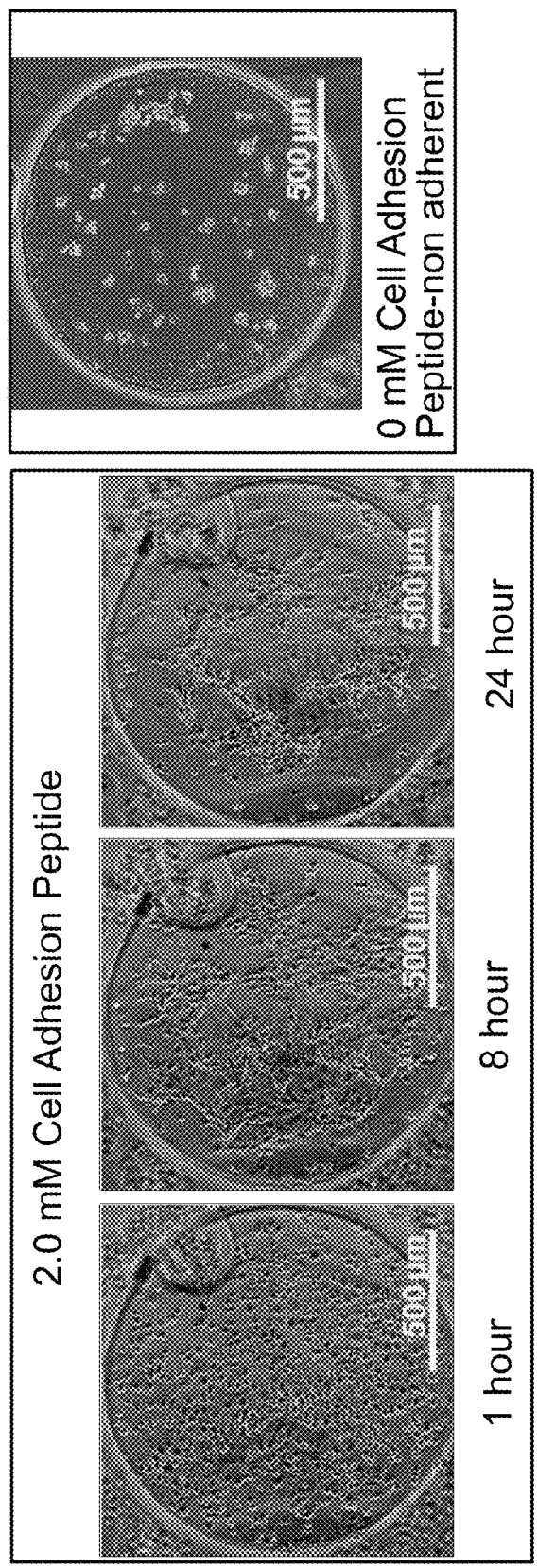

Tubulogenesis was scored as non-adhesion, monolayer formation, and network formation between 1-12 hours and 12-24 hours and all trials were accumulated over 3 separate experiments per hydrogel stiffness. As shown in FIGS. 24A & 24B, four conditions consistently generated tubule networks: 45 mg/mL, 0.25 mM CRGDS (SEQ ID NO:2) before 12 hours; 62 mg/mL, 0.25 CRGDS (SEQ ID NO:2) after 12 hours; 45 mg/mL, 1 mM CRGDS (SEQ ID NO:2) after 12 hours; and 45 mg/mL, 2 mM CRGDS (SEQ ID NO:2) after 12 hours. Further, FIGS. 25A-25C depict tubule networks formed in this Example.

Example 7

In this Example, PEG-hydrogel array formulations with controlled stiffness and cyclic RGD were formed and analyzed for ability to support tubulogenesis for up to 48 hours of cell seeding.

Figure 26A:
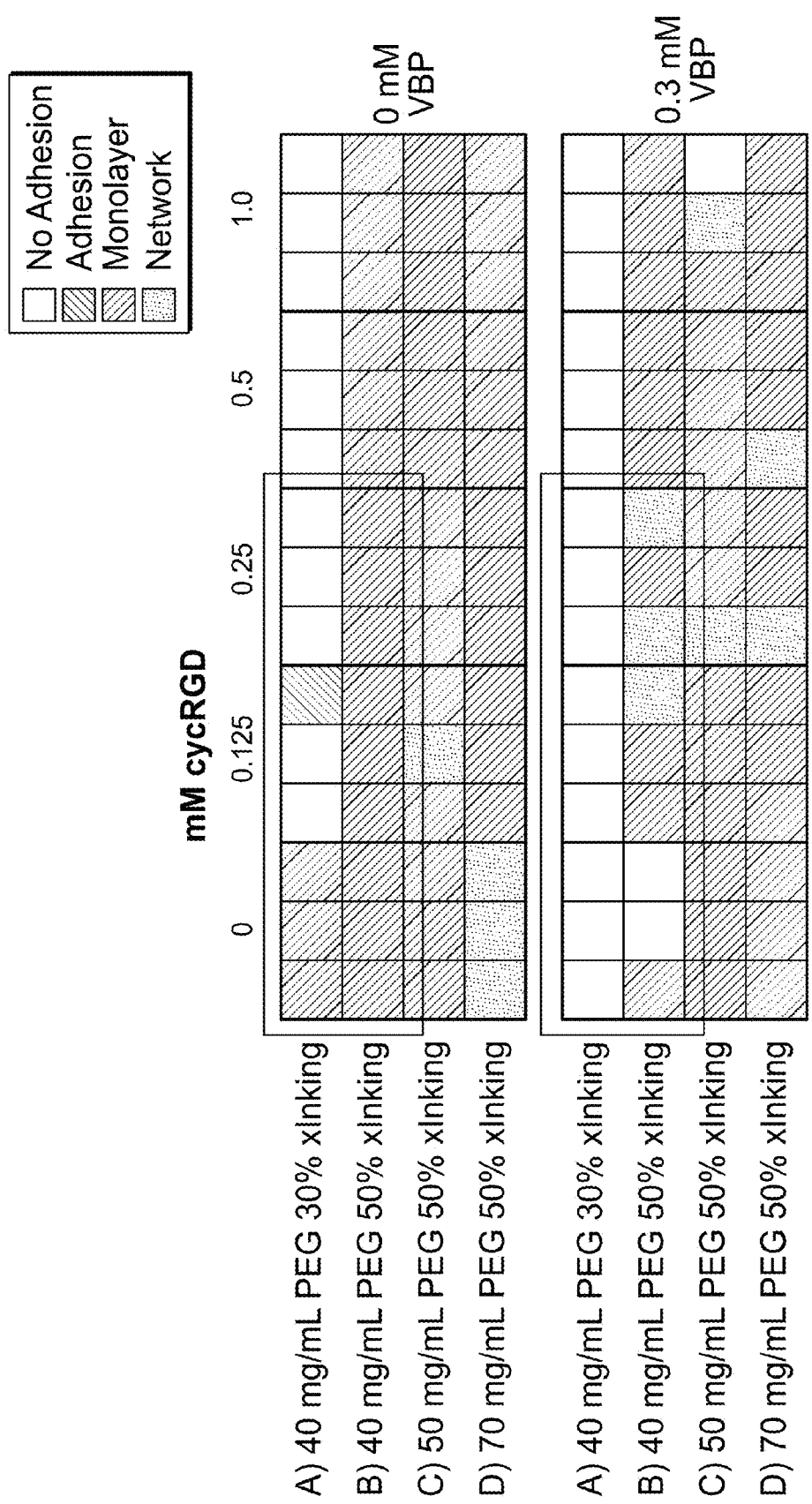
FIGS. 26A & 26B depict heat maps illustrating which PEG hydrogel surfaces support tubule network formation by HUVECs 24 hours post-seeding when surfaces present cyclic RGD rather than CRGDS (SEQ ID NO:2) adhesion peptide as analyzed in Example 7.
Figure 26B:
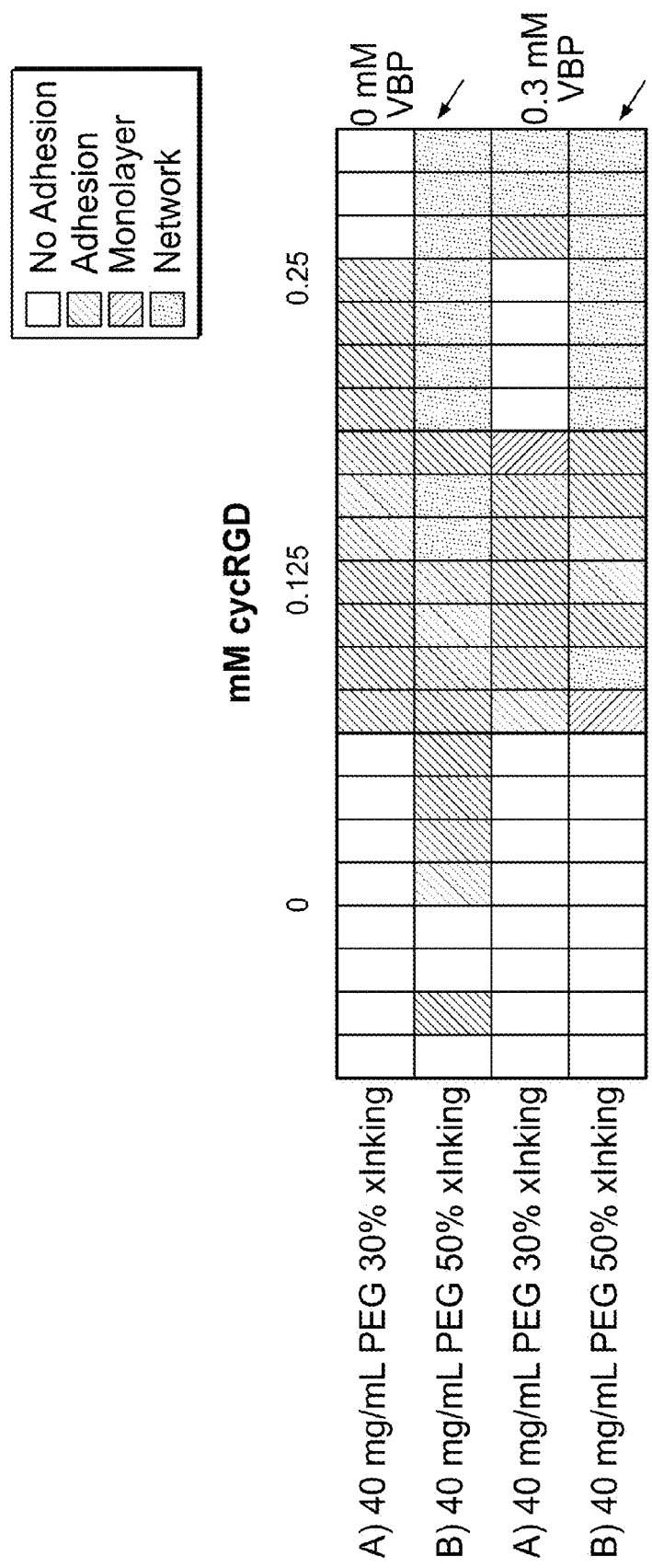

Hydrogel array solutions were created by combining 40, 50 or 70 mg/mL 20 kDa 8-arm norbornene-functionalized PEG with 0 to 1 mM cyclic RGD{Fd}C (SEQ ID NO:33) adhesion peptide, additional CRDGS (SEQ ID NO:32) scrambled adhesion peptide to maintain a total adhesion peptide concentration of 1 mM, 0.3 mM of either CE{Fd}{Ad}{Yd}{Ld}IDFNWEYPASK (SEQ ID NO:35) VEGF binding peptide or the scrambled version CD{Ad}PYN{Fd}EFAWE{Yd}VIS{Ld}K (SEQ ID NO:36), KCGGPQGIWGQCGK (SEQ ID NO:27) crosslinking peptide at molar excess concentrations of either 1.2 or 2× to PEG, and 0.05% IRGACURE 2959 photoinitiator in phosphate buffered saline. The solutions were polymerized into hydrogels under UV light (90 mW/cm$^2$, 365 nm, 3 seconds). HUVECs were seeded at a density of $8.5\times10^4$ cells/cm$^2$ on hydrogel arrays and incubated in M199 supplemented with EGM2 growth supplement and photographed 24 hours after seeding. Tubulogenesis was scored as non-adhesion, single cell/colony adhesion, monolayer formation, and network formation. The results are shown in FIGS. 26A & 26B. Specifically, as shown in FIG. 26B, formulation B with 0.25 mM cyclic RGD containing either 0 or 0.3 mM VBP consistently generated tubules.

Example 8

In this Example, PEG-hydrogel array formulations with controlled stiffness and cyclic RGD were formed and analyzed for ability to support tubulogenesis for up to 48 hours of cell seeding.

Figure 27A:
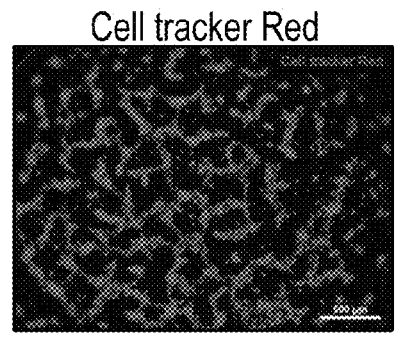
FIGS. 27A-27C depict photographs of HUVECs forming tubule networks on hydrogel surfaces as analyzed in Example 8. Particularly
Figure 27A:
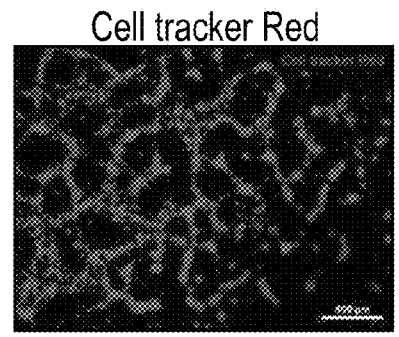
Figure 27B:
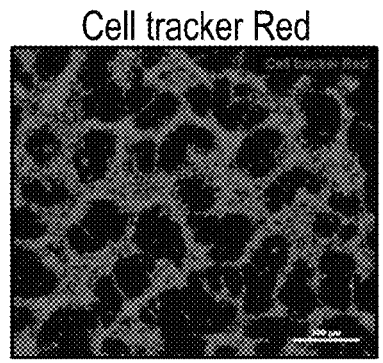
Figure 27B:
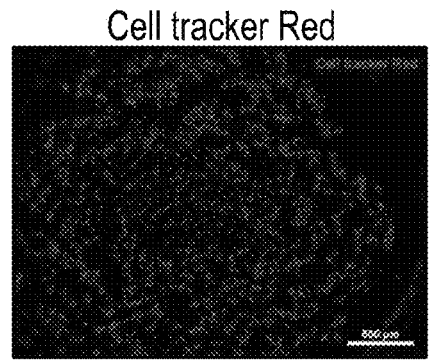
Figure 27C:
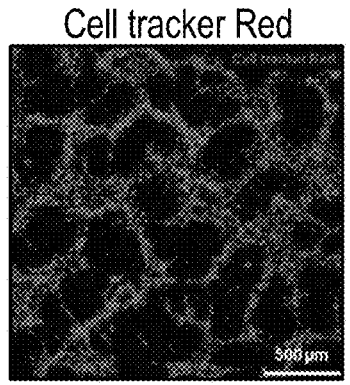
Figure 27C:
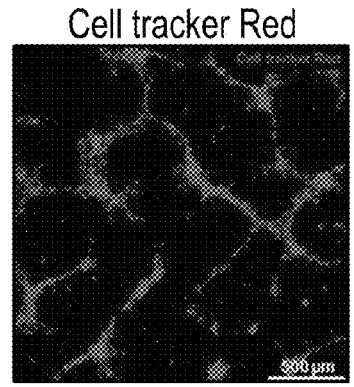

Hydrogel array solutions were created by combining 40 mg/mL 20 kDa 8-arm norbornene-functionalized PEG with 0.25 mM cyclic RGD{Fd}C (SEQ ID NO:33) adhesion peptide, 0 to 0.3 mM of either CE{Fd}{Ad}{Yd}{Ld}IDFNWEYPASK (SEQ ID NO:35) VEGF binding peptide or the scrambled version CD {Ad}PYN{Fd}EFAWE{Yd}VIS {Ld}K (SEQ ID NO:36), KCGGPQGIWGQCGK (SEQ ID NO:27) crosslinking peptide at a 2× molar excess concentration to PEG and 0.05% IRGACURE 2959 photoinitiator in phosphate buffered saline. The solutions were polymerized into hydrogels under UV light (4.5 mW/cm$^2$, 365 nm, 2 minutes). HUVECs were seeded at a density of $1.2\times10^5$ cells/cm$^2$ on hydrogel arrays and incubated in M199 supplemented with EGM2 growth supplement, where the VEGF concentration in EGM2 was defined at 5 ng/mL. The cells were photographed 24 hours and 48 hours after seeding. Results are shown in FIGS. 27A-27C.

Example 9

In this Example, PEG-hydrogel array formulations with controlled stiffness and CRGDS (SEQ ID NO:2) were formed and analyzed for ability to support tubulogenesis by encapsulated HUVECs for 24 to 48 hours after cell seeding.

Figures 28A, 28B:
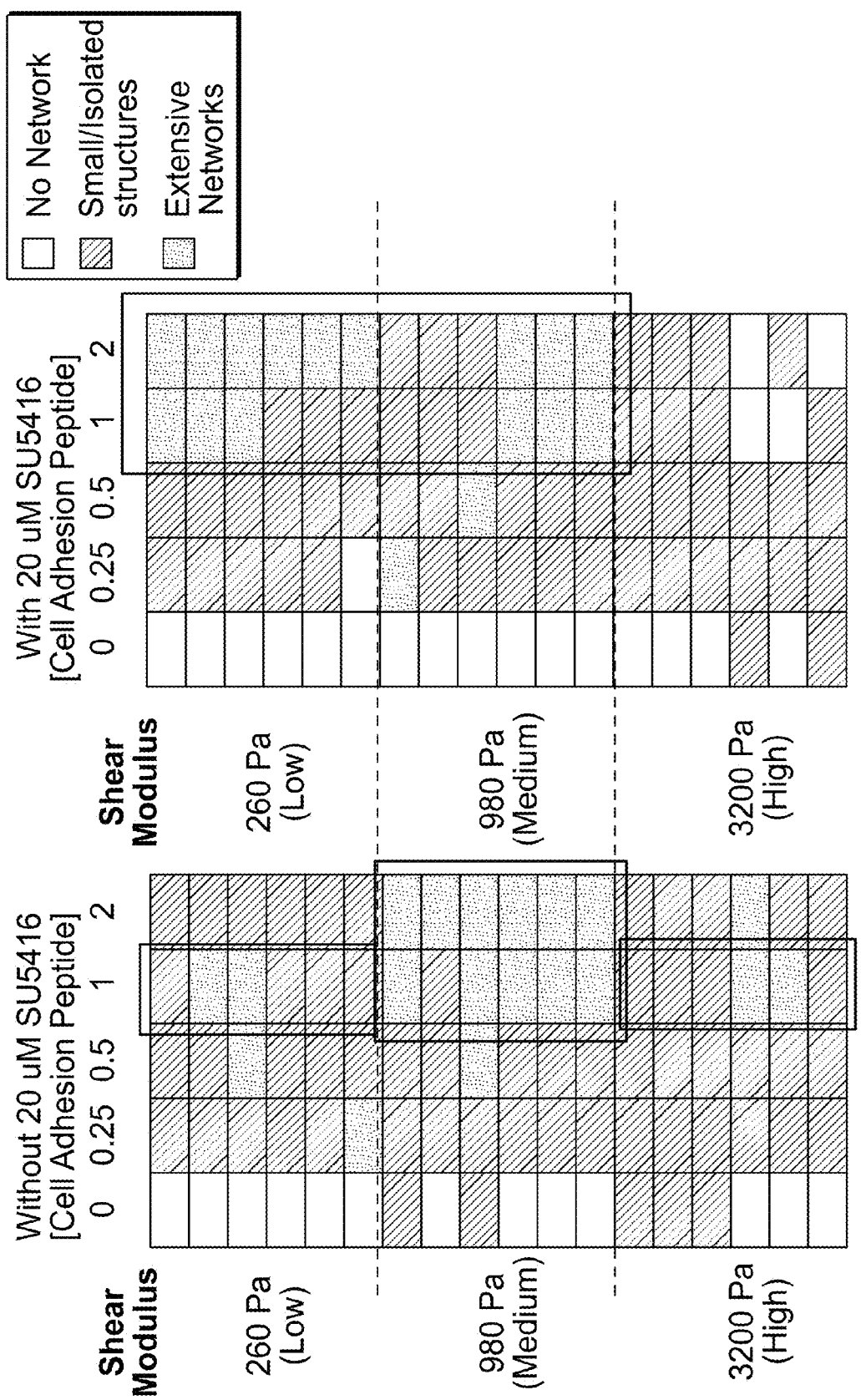
FIGS. 28A & 28B depict heat maps illustrating which PEG hydrogels support 3D tubule formation by HUVECs 24 hours post-encapsulation as analyzed in Example 9.
Figure 29A:
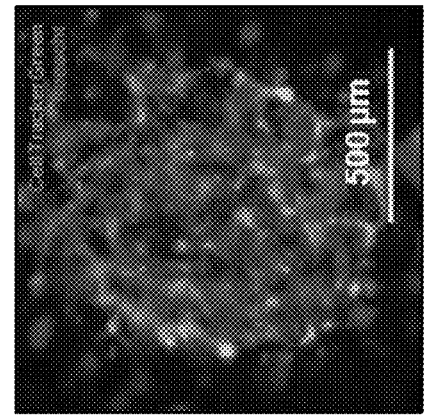
FIGS. 29A & 29B depict photographs of HUVECs forming 3D tubule structures in PEG hydrogels 24 hours post-encapsulation well as examples of HUVECs failing to form tubule structures as analyzed in Example 9.
Figure 29A:
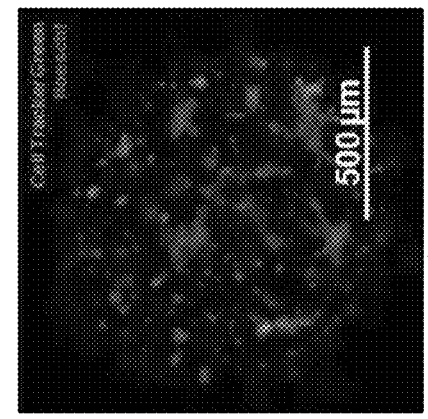
Figure 29A:
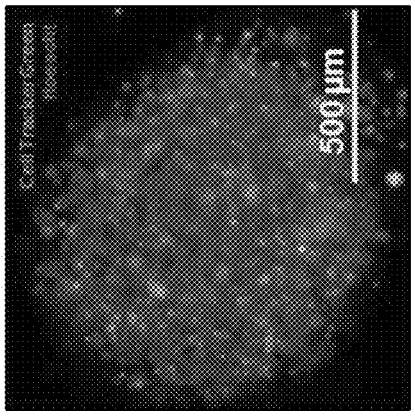
Figure 29B:
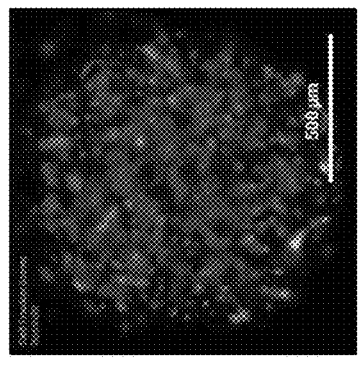
Figure 29B:
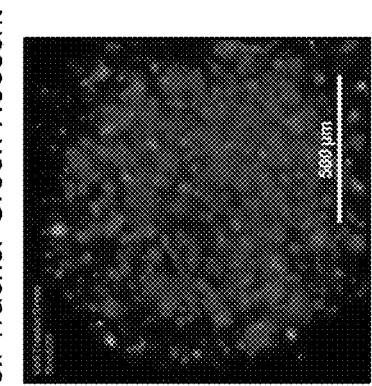

Hydrogel solutions were created by combining 36, 42 or 60 mg/mL 20 kDa 8-arm norbornene-functionalized PEG with 0 to 2 mM CRGDS (SEQ ID NO:2) adhesion peptide, additional CRDGS (SEQ ID NO:32) scrambled adhesion peptide to maintain a total adhesion peptide concentration of 2 mM, KCGGPQGIWGQCGK (SEQ ID NO:27) crosslinking peptide at a 2× molar excess concentration to PEG and 0.05% IRGACURE 2959 photoinitiator in phosphate buffered saline. The solutions were polymerized into hydrogels under UV light (90 mW/cm$^2$, 365 nm, 2 seconds). HUVECs were encapsulated at a density of 2.0×10$^7$ cells/cm$^2$ in hydrogels and incubated in M199 supplemented with EGM2 growth supplement. The cells were stained with Cell Tracker Green CMFDA, photographed 24 hours after seeding and scored for total tubule length in the spots. Results are shown FIGS. 18, 28 and 29. Specifically, as shown in FIGS. 28A & 28B, medium modulus gels containing 1 or 2 mM CRDGS (SEQ ID NO:2), or low modulus gels containing 2 mM CRGDS (SEQ ID NO:2) in the presence of SU5416 VEGF inhibitor consistently generated tubules.

Example 10

Similar to Example 9, in this Example, PEG-hydrogel array formulations with controlled stiffness and CRGDS (SEQ ID NO:2) were formed and analyzed for ability to support tubulogenesis by encapsulated HUVECs for 24, 48 and even up to 72 hours after cell seeding.

Figure 30A:
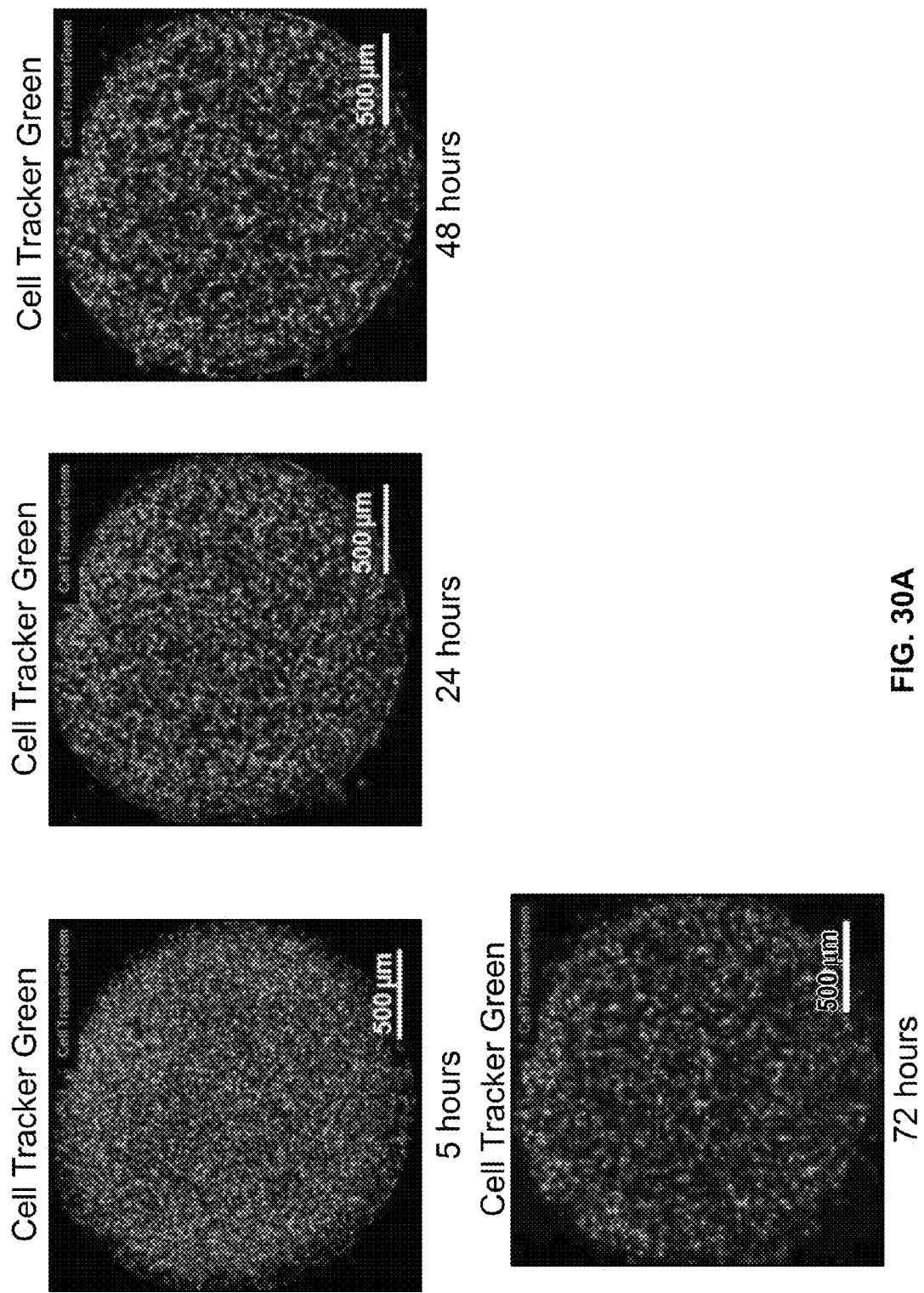
FIGS. 30A & 30B depict photographs of HUVECs forming 3D tubule networks in PEG hydrogels 24 and 48 hours post-encapsulation and networks destabilizing after 72 hours as analyzed in Example 10.
Figure 30B:
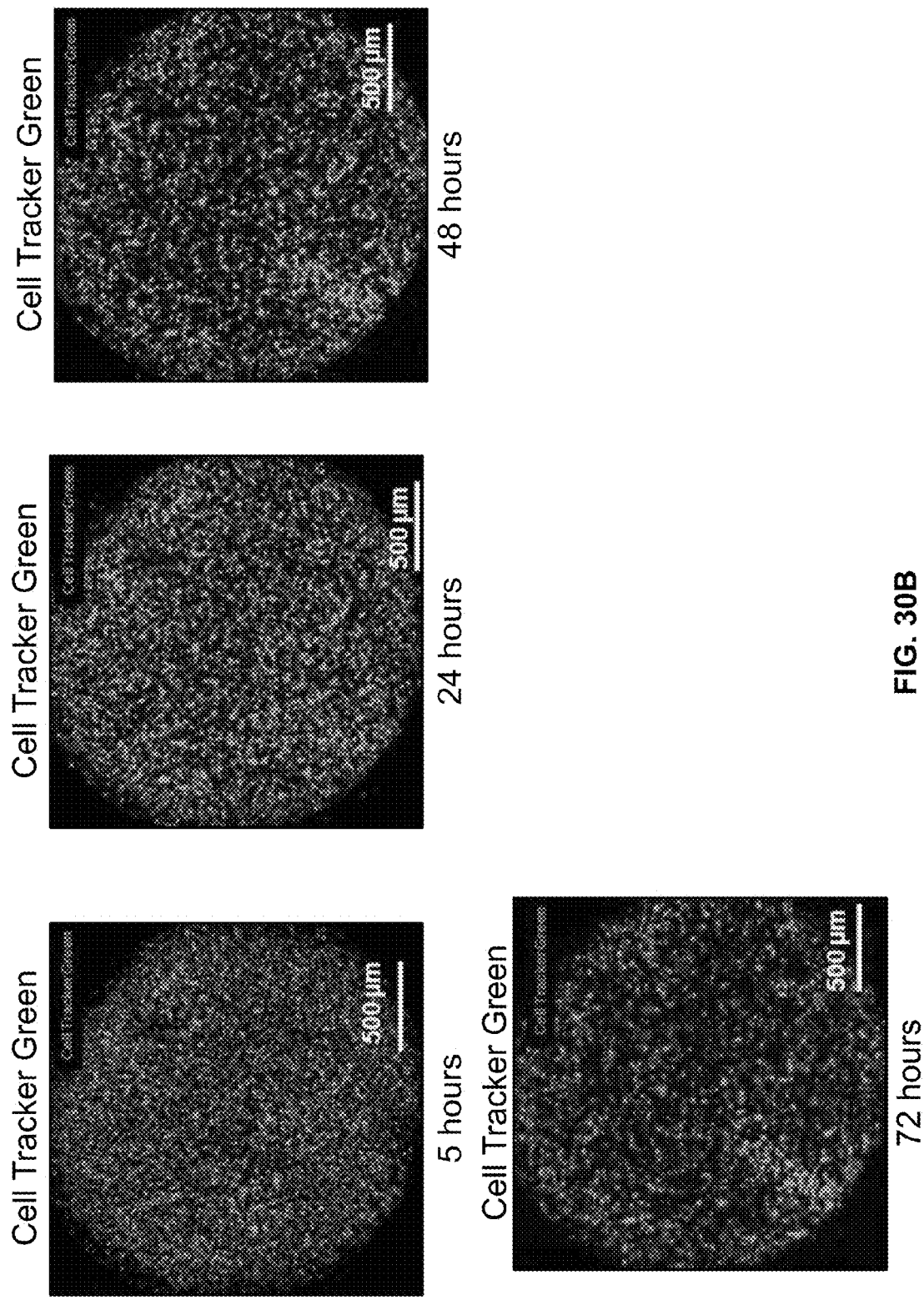
Figures 33A, 33B:
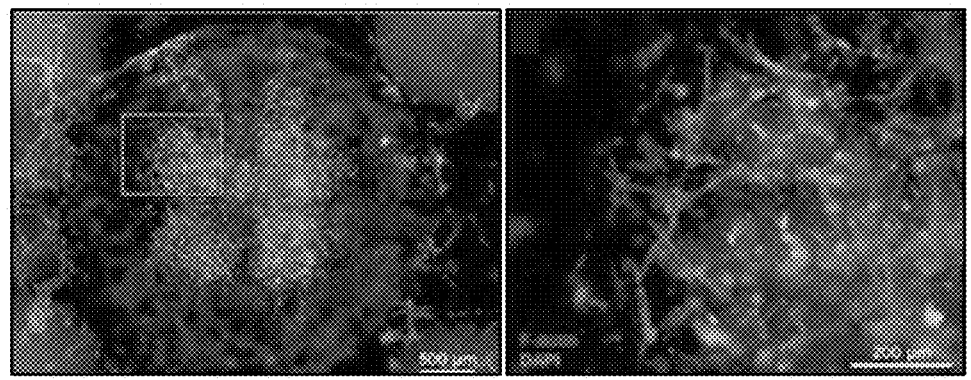
FIGS. 33A-33D illustrates the effects of adding a reinforcing hydrogel to an existing pro-tubulogenic hydrogel to enhance tubule network stability as well as the process of implementing reinforcing hydrogels as analyzed in Example 12.
Figure 33C:
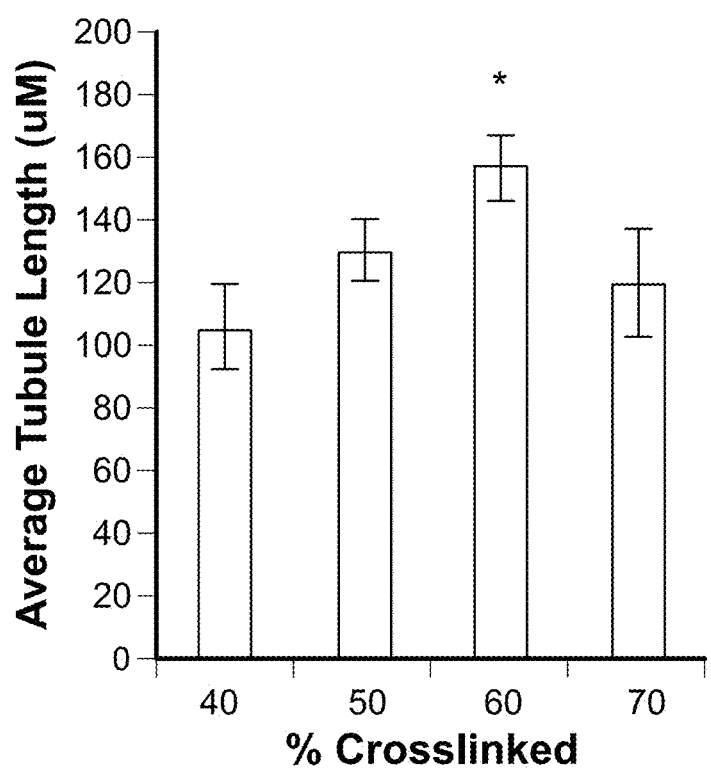
Figure 33D:
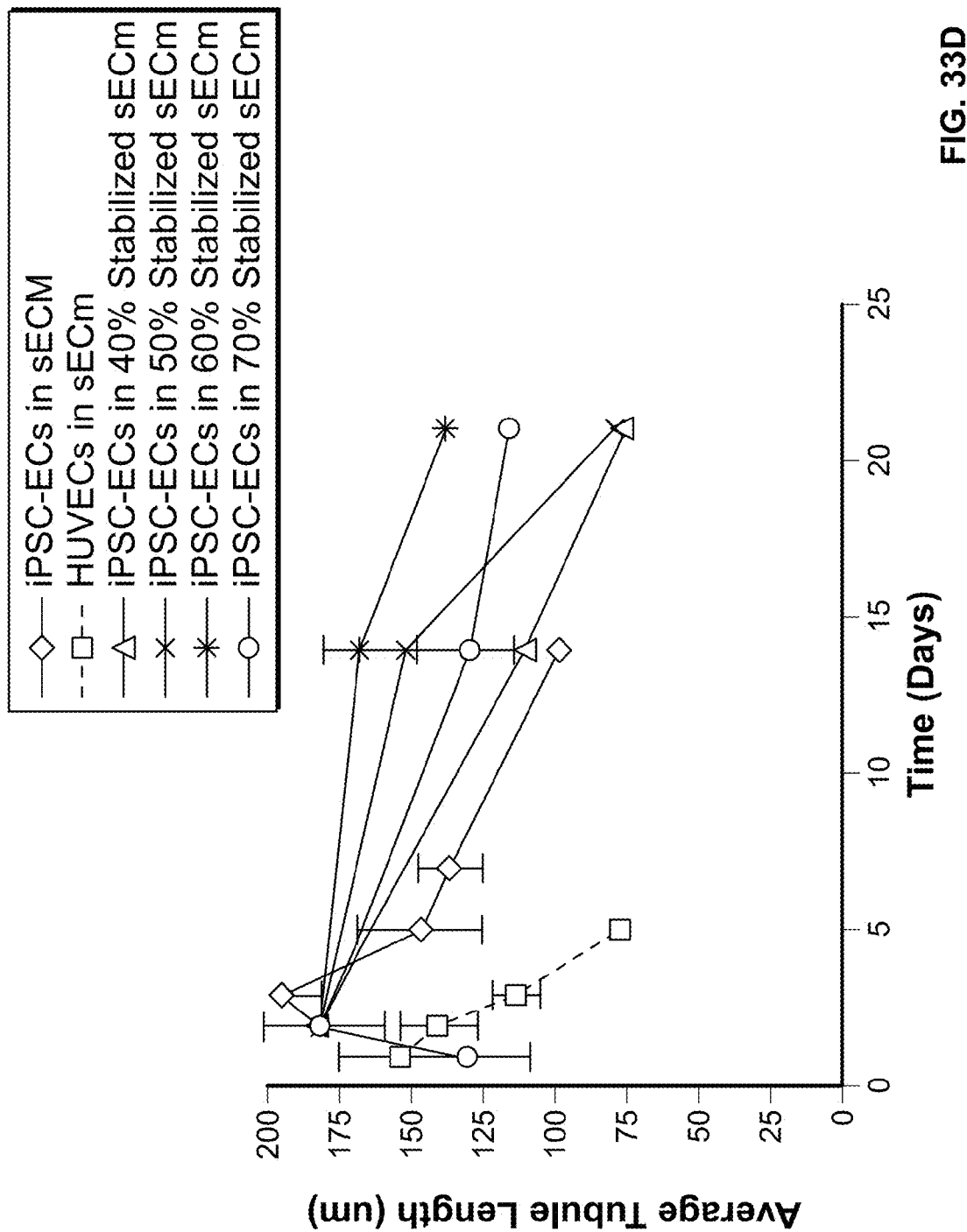

Hydrogel solutions were created by combining 40 mg/mL 20 kDa 8-arm norbornene-functionalized PEG with 2 mM CRGDS (SEQ ID NO:2) adhesion peptide, 0 or 0.07 mM CE{Fd}{Ad}{Yd}{Ld}IDFNWEYPASK (SEQ ID NO:35) VEGF binding peptide, additional CD{Ad}PYN{Fd}EFAWE{Yd}VIS{Ld}K (SEQ ID NO:36) scrambled VEGF binding peptide to maintain a total binding peptide concentration of 0.3 mM, KCGGPQGIWGQCGK (SEQ ID NO:27) crosslinking peptide at a 2× molar excess concentration to PEG and 0.05% IRGACURE 2959 photoinitiator in phosphate buffered saline. The solutions along with HUVECs were polymerized into hydrogels under UV light (90 mW/cm$^2$, 365 nm, 3 seconds). HUVECs were encapsulated at a density of 2.0×10$^7$ cells/cm$^2$ and incubated in M199 supplemented and EGM2 growth supplement with VEGF concentration defined at 10 ng/mL. The cells were stained with Cell Tracker Green CMFDA, photographed 5, 24, 48 and 72 hours after seeding and scored for total tubule length in the spots. As shown in FIGS. 30A & 30B, the tubular networks were stable for up to 72 hours in culture.

Example 11

In this Example, PEG-hydrogel array formulations with controlled stiffness and CRGDS (SEQ ID NO:2) were formed and analyzed for ability to support tubulogenesis by encapsulated iPSC-derived endothelial cells beyond 48 hours after cell seeding.

Hydrogel solutions were created by combining 40 mg/mL 20 kDa 8-arm norbornene-functionalized PEG with 2 mM CRGDS (SEQ ID NO:2) adhesion peptide, KCGGPQGIWGQCGK (SEQ ID NO:27) crosslinking peptide at a 2× molar excess concentration to PEG and 0.05% IRGACURE 2959 photoinitiator in phosphate buffered saline. The solutions along with iPSC-derived endothelial cells were polymerized into hydrogels under UV light (90 mW/cm$^2$, 365 nm, 3 seconds) inside PDMS microchannels. iPSC-derived endothelial cells were encapsulated at a density of 1.0 and 8.5×10$^7$ cells/cm$^2$ in hydrogels and incubated in VASCULIFE basal medium, endothelial growth supplement from Cellular Dynamics International (CDI) (Madison, Wis.) and 200-1000 ng/mL VEGF. The cells were photographed 8 and 9 days after cell encapsulation. As shown in FIGS. 31A & 31B, iPSC-derived endothelial cells encapsulated in the formulation created tubular networks that were stable for at least up to 9 days.

Example 12

Similar to Example 11, in this Example, PEG-hydrogel array formulations with controlled stiffness and CRGDS (SEQ ID NO:2) were formed and analyzed for ability to support tubulogenesis by encapsulated iPSC-derived endothelial cells beyond 48 hours after cell seeding.

Hydrogel solutions were created by combining 40 mg/mL 20 kDa 8-arm norbornene-functionalized PEG with 2 mM CRGDS (SEQ ID NO:2) adhesion peptide, KCGGPQGIWGQCGK (SEQ ID NO:27) crosslinking peptide at a 2× molar excess concentration to PEG and 0.05% IRGACURE 2959 photoinitiator in phosphate buffered saline. The solutions and IPSC-derived endothelial cells were polymerized into hydrogels under UV light (5-10 mW/cm$^2$, 365 nm, 2 minutes). The IPSC-derived endothelial cells were encapsulated at a density of 5.0×10$^6$ cells/cm$^2$ in hydrogels and incubated in VASCULIFE basal medium and endothelial growth supplement from CDI. The cells were photographed 1, 2, 3 and 5 days after cell encapsulation. As shown in FIGS. 32A & 32B, iPSC-derived endothelial cells encapsulated in the formulation created tubular networks that were stable for at least up to 5 days.

Further, 24 hours after encapsulation, a second hydrogel solution consisting of 40 mg/mL 20 kDa 8-arm norbornene-functionalized PEG, no adhesion peptide, KCGGPQGIWGQCGK (SEQ ID NO:27) crosslinking peptide at a 2.4× molar excess concentration to PEG and 0.05% IRGACURE 2959 photoinitiator in phosphate buffered saline was pipetted to surround the initial hydrogel array. The reinforcing hydrogels were cured under UV light (5-10 mW/cm$^2$, 365 nm 2 minutes). The cells were incubated in VASCULIFE basal medium and endothelial growth supplement from CDI and photographed 14 days after hydrogel reinforcement. Results are shown in FIGS. 33A-33D.

Example 13

Figure 34A:
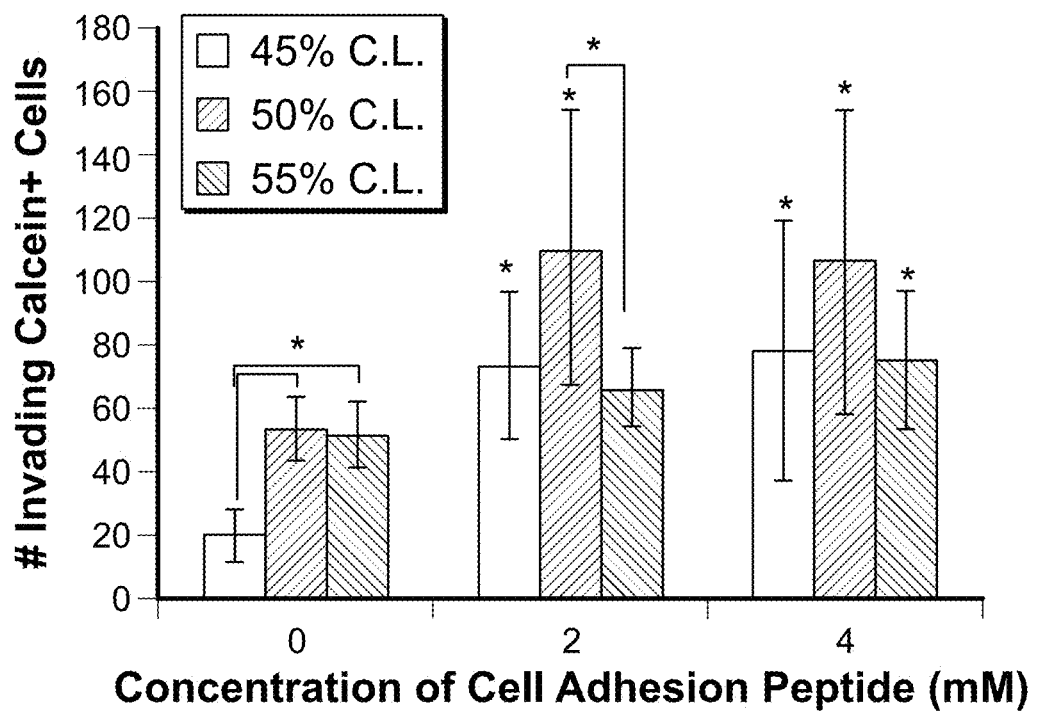
FIGS. 34A & 34B illustrates the effects of varying crosslinking density and CRGDS (SEQ ID NO:2) adhesion peptide concentration on capillary sprouting from a centralized source of IPSC-ECs as analyzed in Example 13.
Figure 34B:
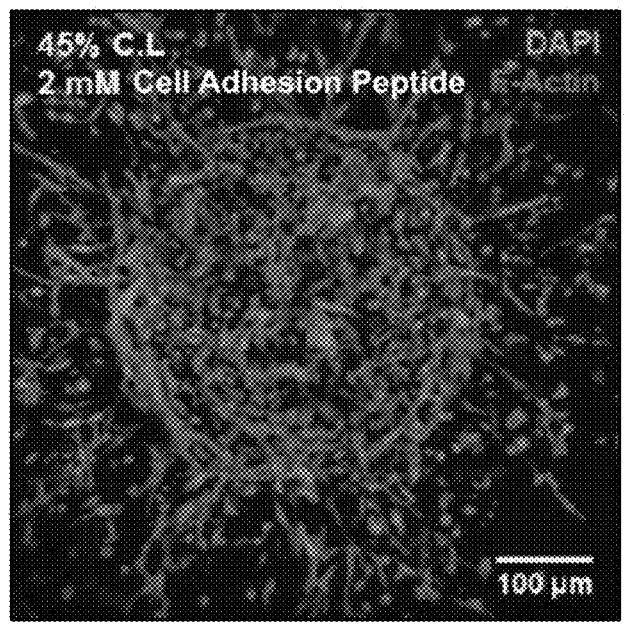

In this Example, PEG-hydrogel array formulations with controlled stiffness and CRGDS (SEQ ID NO:2) were formed and analyzed for ability to support tubule angiogenic sprouting from an endothelial cell source.

iPSC-derived endothelial cells at a density of 4.0×10$^7$ cells/mL were encapsulated in a 0.5 μL hydrogel sphere consisting of 40 mg/mL 20 kDa 8-arm norbornene-functionalized PEG with 2 to 4 mM CRGDS (SEQ ID NO:2) adhesion peptide, KCGGPQGIWGQCGK (SEQ ID NO:27) crosslinking peptide at a 1.8 to 2.2× molar excess concentration to PEG and 0.05% IRGACURE 2959 photoinitiator in phosphate buffered saline. The sphere was cured at the end of a pipet tip under UV light (175 mW/cm$^2$, 365 nm, 1.2 seconds). The spheres were incubated overnight in VASCULIFE basal medium and endothelial growth supplement from CDI before 10 μL of a second identical hydrogel formulation was delivered around the initial sphere. The second hydrogel array was cured under UV light (4.5 mW/cm$^2$, 365 nm, 30 seconds) and the cells were incubated in VASCULIFE basal medium and endothelial growth supplement from CDI for 3 more days. As shown in FIGS. 34A & 34B, the hydrogel array formulations that contained CRGDS (SEQ ID NO:2) supported endothelial capillary sprouting from a localized cell source.

Example 14

In this Example, two sets of hydrogel arrays were formed and analyzed for their ability to incorporate peptides therein.

Figure 35A:
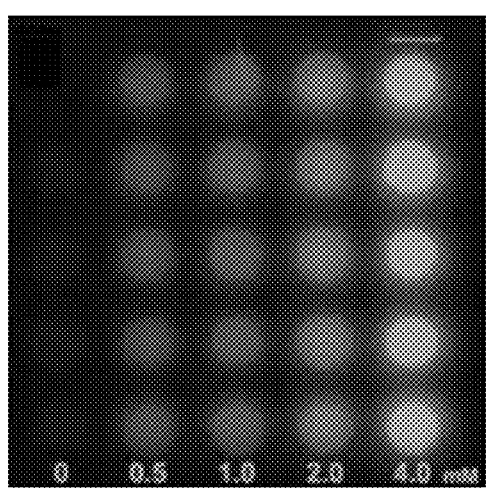
FIGS. 35A & 35B illustrates the effects of varying adhesion peptide concentration in hydrogel precursor solutions on peptide presentation in cured hydrogels as analyzed in Example 14.
Figure 35A:
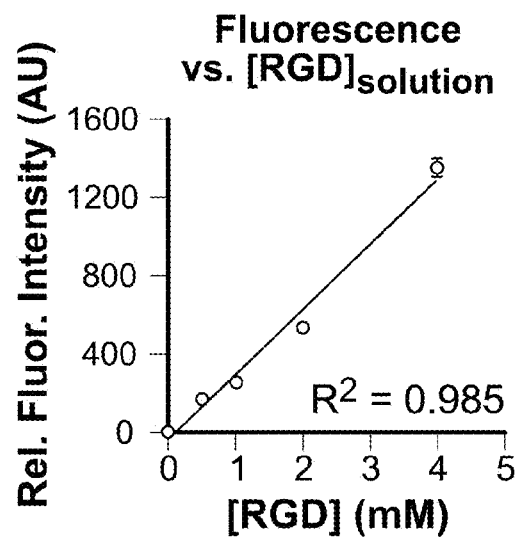
Figure 35B:
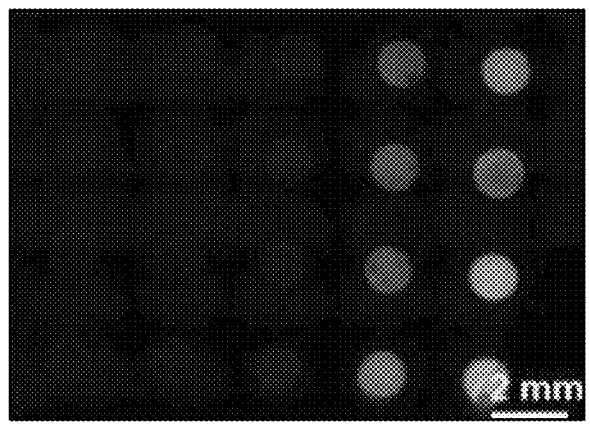
Figure 35B:
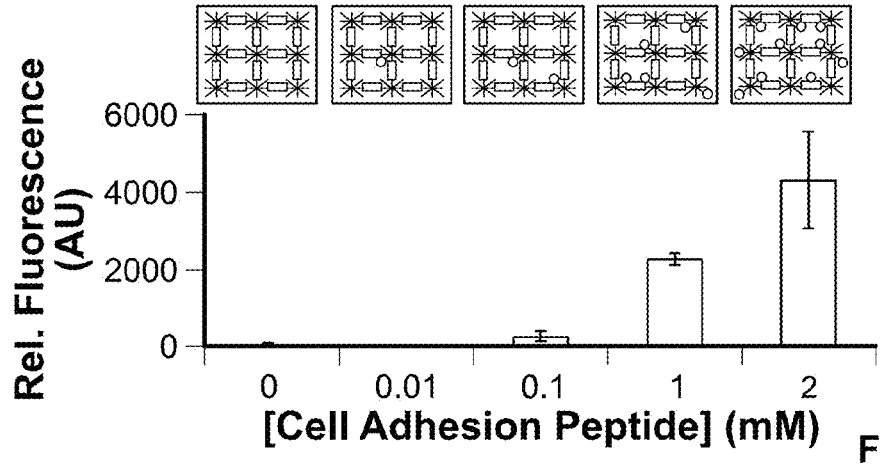

The first hydrogel array was prepared using 80 mg/mL 20 kDa 8-arm norbornene-functionalized PEG with 0 to 4 mM CRGDS (SEQ ID NO:2) adhesion peptide, 3.4 kDa dithiolated PEG crosslinker at a 1:1 molar ratio to 8-arm PEG and 0.05% IRGACURE 2959 photoinitiator in phosphate buffered saline. The second hydrogel array was prepared using 90 mg/mL 20 kDa 8-arm norbornene-functionalized PEG with 0 to 2 mM CRGDS (SEQ ID NO:2) adhesion peptide, 3.4 kDa dithiolated PEG crosslinker at a 2× molar excess concentration to 8-arm PEG and 0.05% IRGACURE 2959 photoinitiator in phosphate buffered saline. A sulfodichlorophenol ester mediated reaction labeled the N-termini of pendant peptides with Fluorescein and the spots were photographed under an epifluorescence microscope. As shown in FIGS. 35A & 35B, fluorescence intensity increased proportionally with initial peptide concentration, indicating controlled peptide incorporation into the hydrogel arrays.

Example 15

In this Example, norbornene-functionalized 20 kDa 8-arm molecules were reacted to CRGDS (SEQ ID NO:2) peptides to evaluate efficiency of bonding peptide to PEG via the thiol-ene reaction.

Figure 36A:
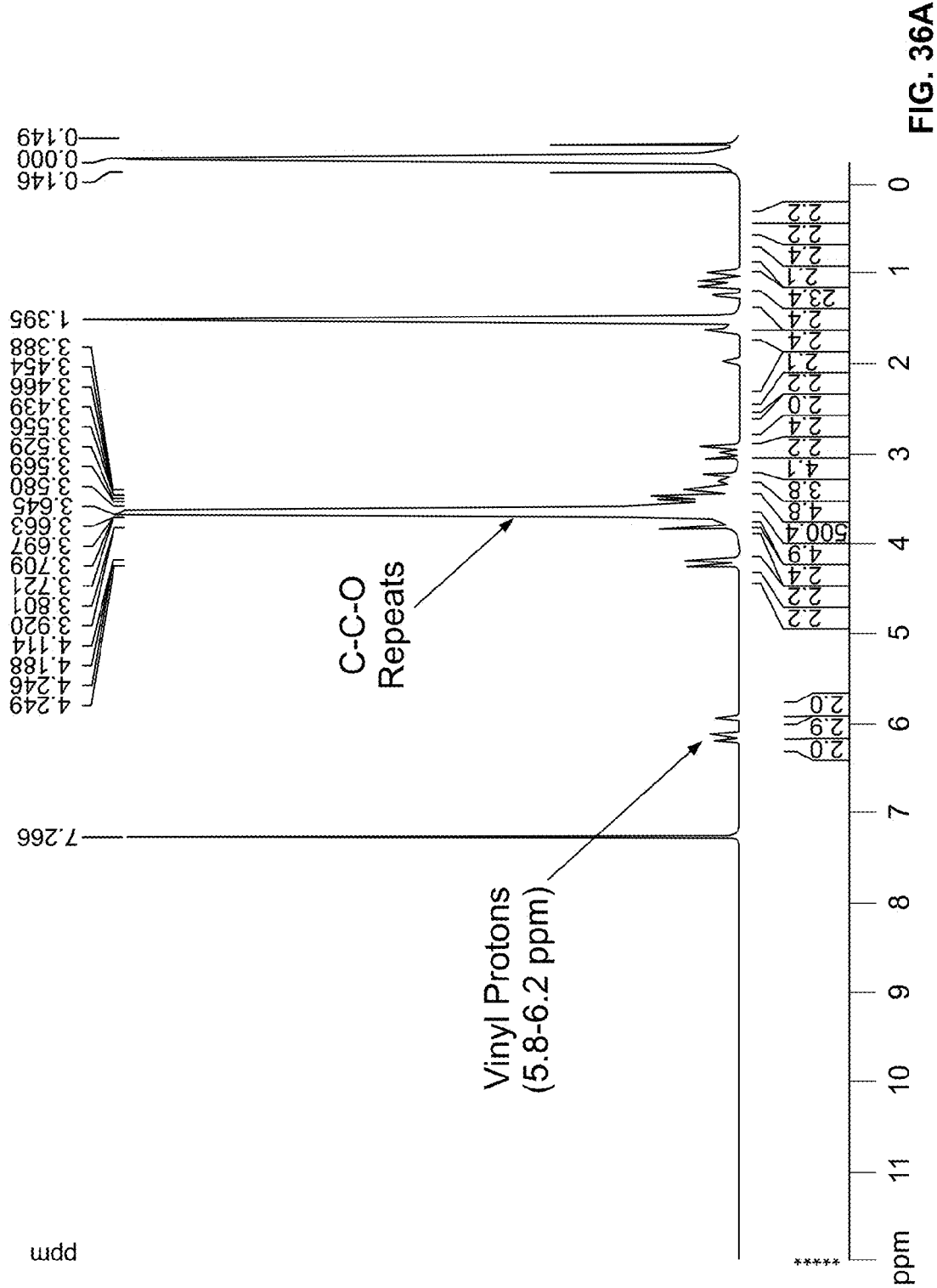
FIGS. 36A-36C illustrates a method using NMR to measure efficiency of coupling pendant peptides to PEG molecules as analyzed in Example 15.
Figure 36B:
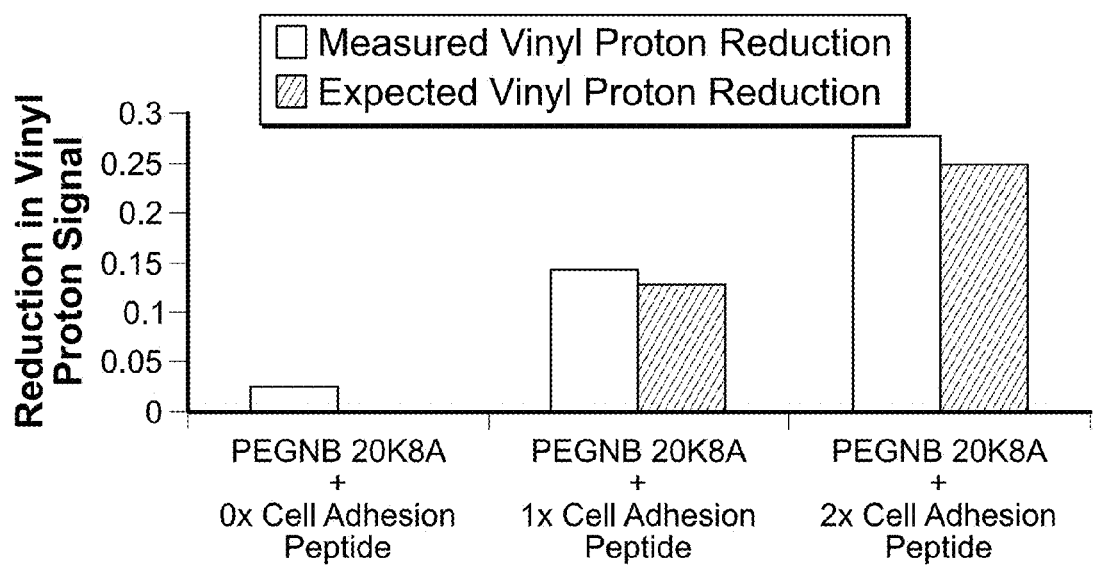
Figure 36C:
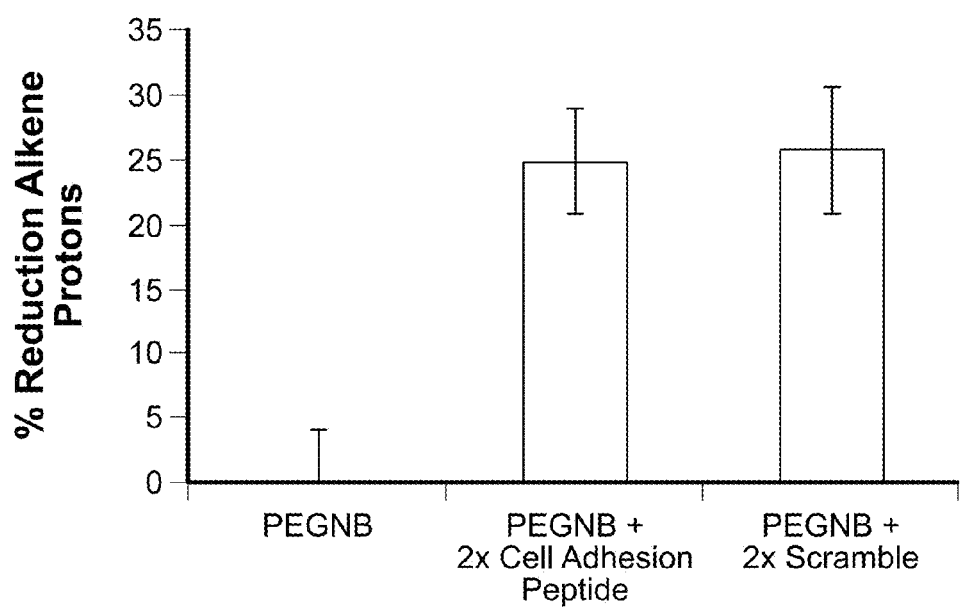
Figure 37A:
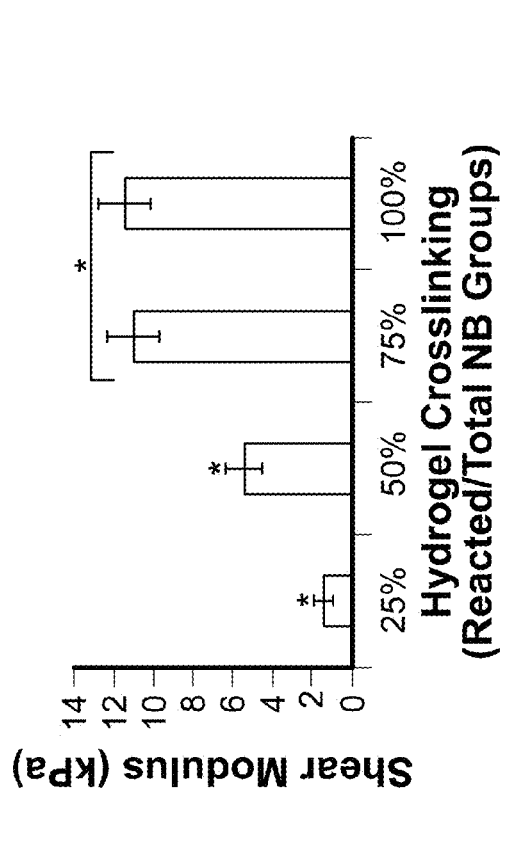
FIGS. 37A-37D illustrates the effects of varying PEG concentrations in hydrogel precursor solutions and crosslinking percent on PEG hydrogel shear modulus as analyzed in Example 16.
Figure 37B:
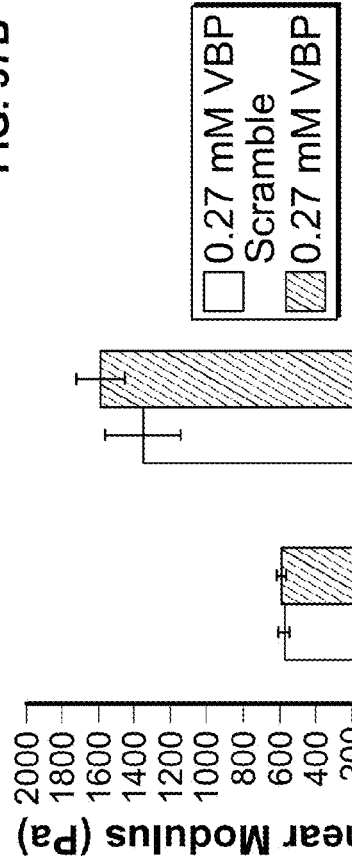
Figure 37C:
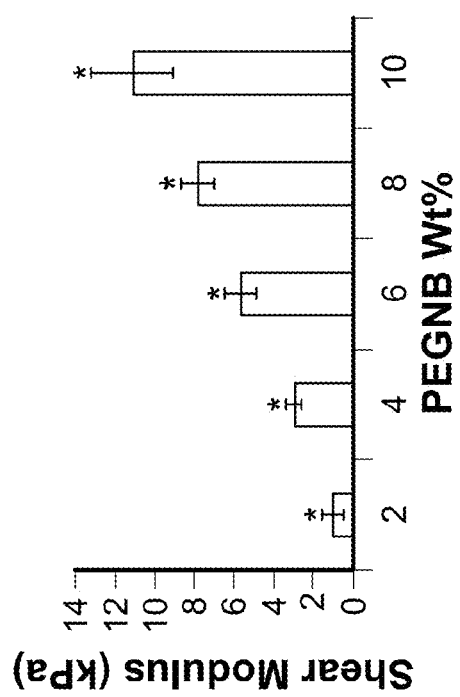
Figure 37D:
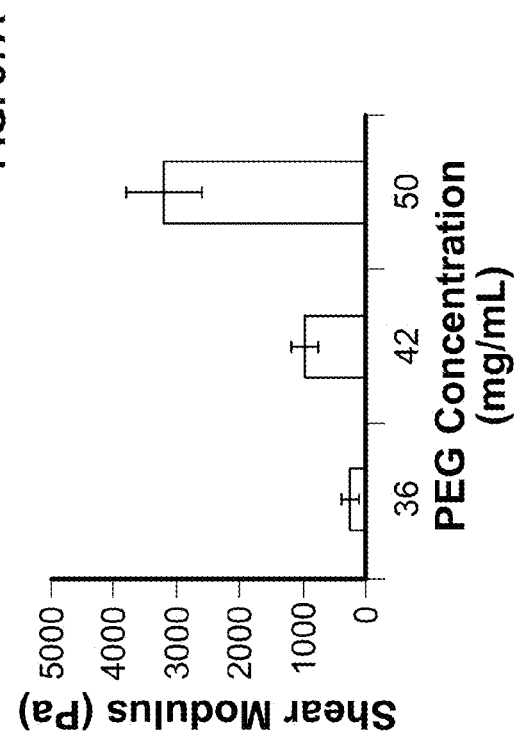
Figures 38A, 38B:
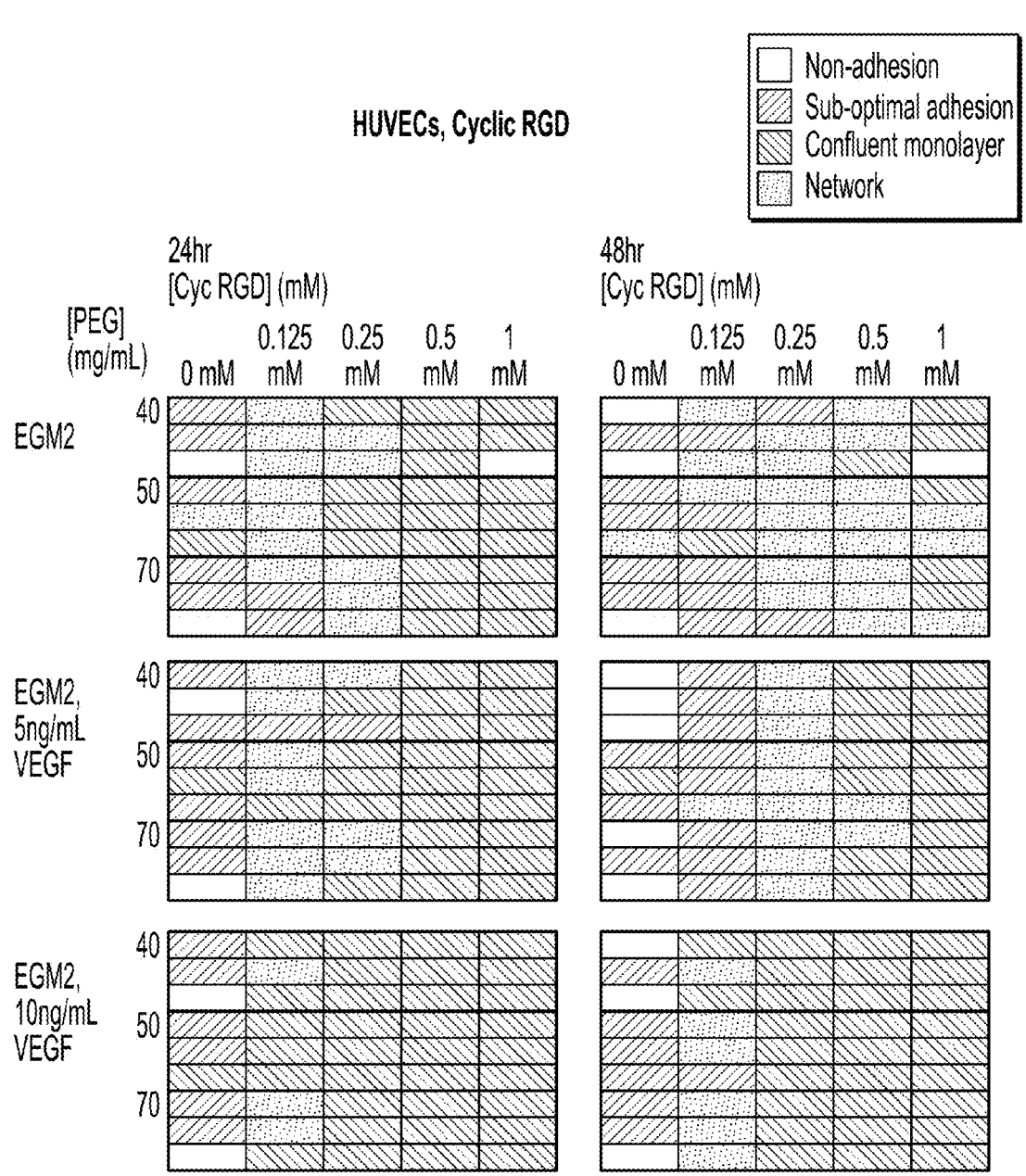
FIGS. 38A & 38B depict heat maps illustrating which PEG hydrogels including cyclic RGD adhesion peptide support tubule formation by HUVECs 24 hours and 48 hours post-seeding as analyzed in Example 17.
Figures 39A, 39B:
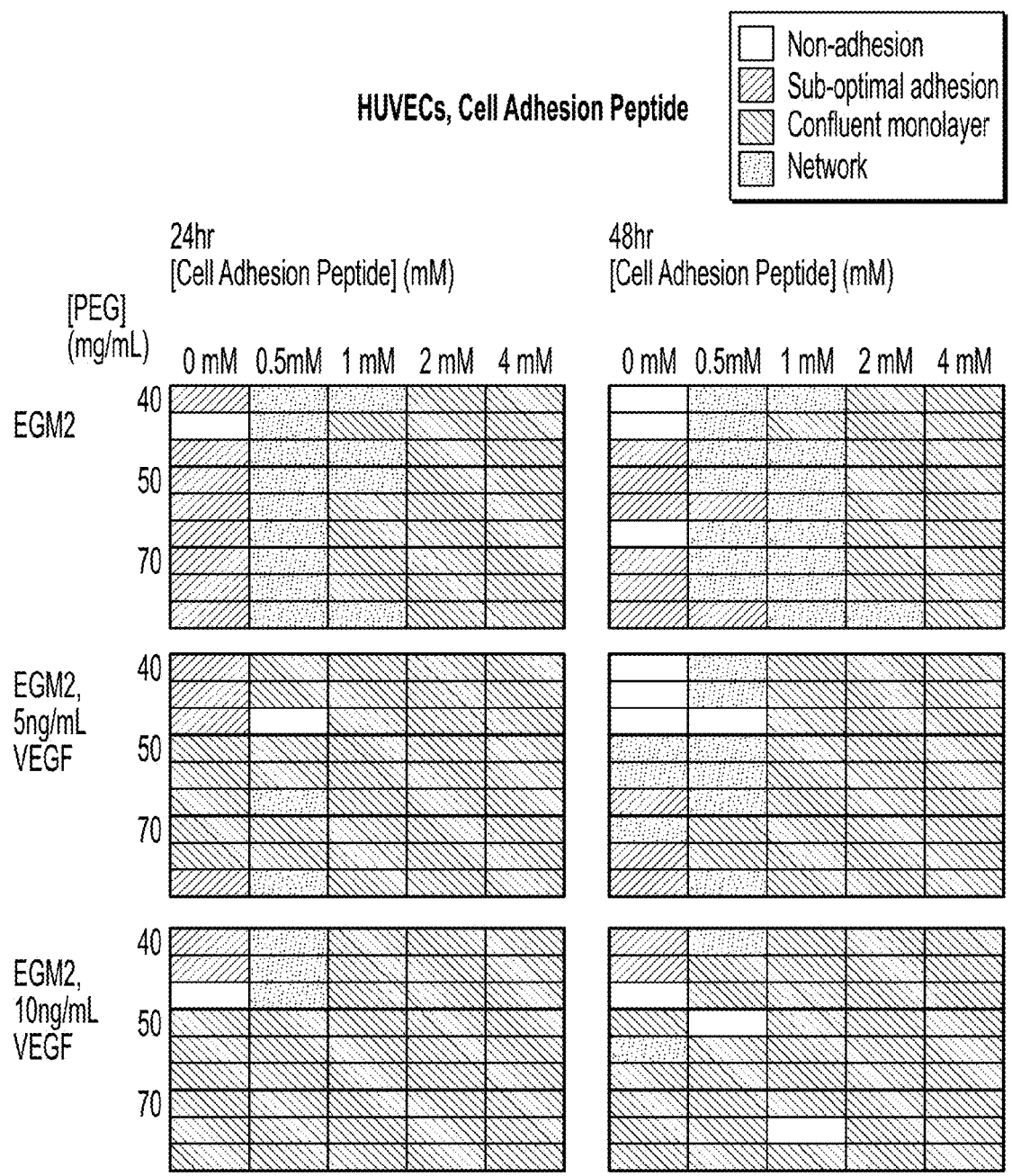
FIGS. 39A & 39B depict heat maps illustrating which PEG hydrogels including CRGDS (SEQ ID NO:2) adhesion peptide support tubule formation by HUVECs 24 hours and 48 hours post-seeding as analyzed in Example 17.
Figure 40A:
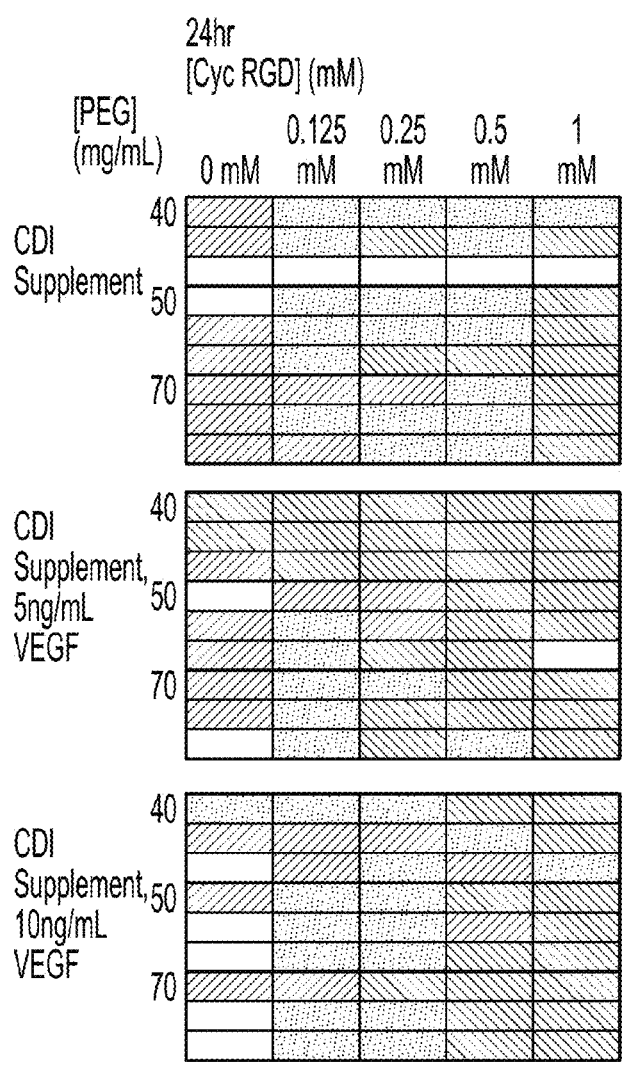
FIGS. 40A & 40B depict heat maps illustrating which PEG hydrogels including cyclic RGD adhesion peptide support tubule formation by iPSC-derived ECs 24 hours and 48 hours post-seeding as analyzed in Example 17.
Figure 40B:
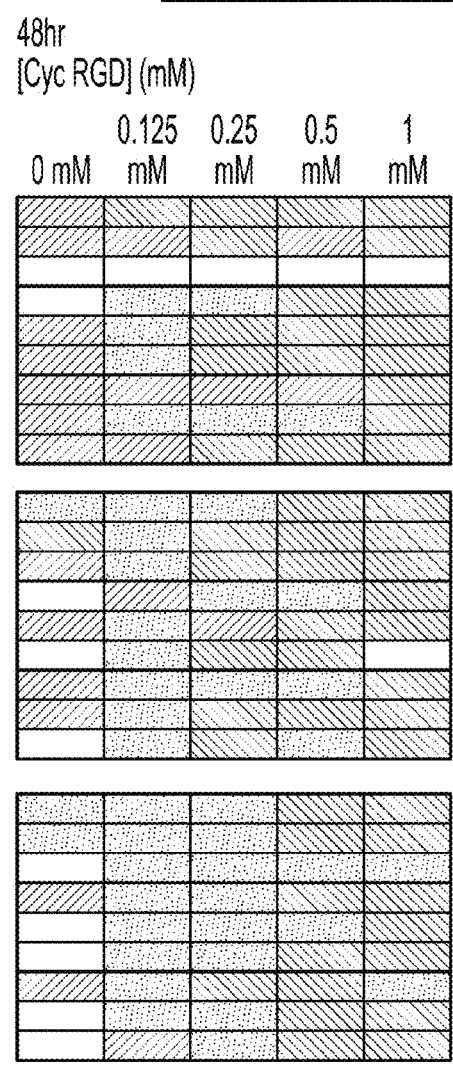
Figure 41A:
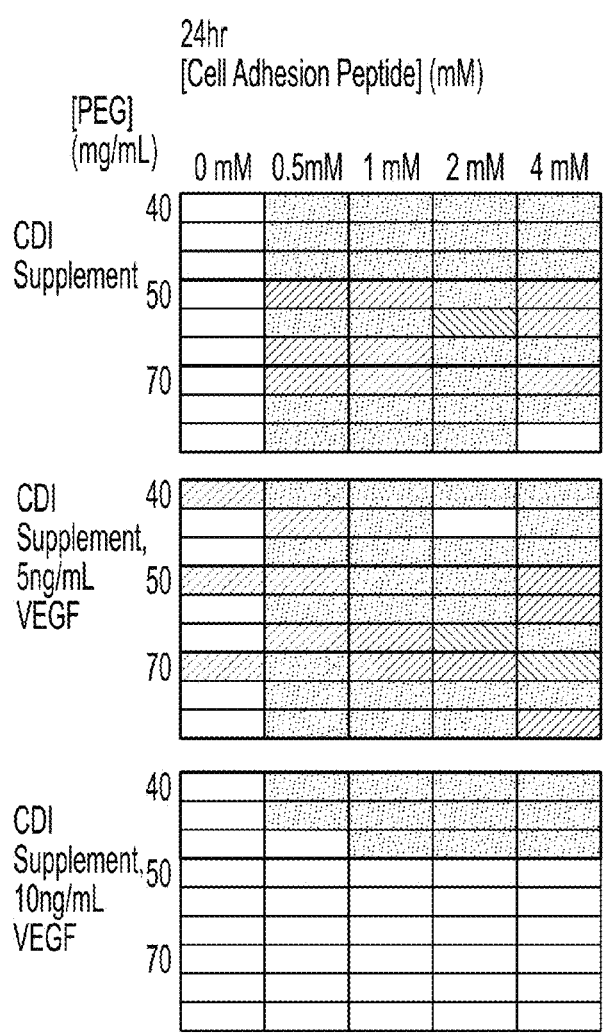
FIGS. 41A & 41B depict heat maps illustrating which PEG hydrogels including CRGDS (SEQ ID NO:2) adhesion peptide support tubule formation by iPSC-derived ECs 24 hours and 48 hours post-seeding as analyzed in Example 17.
Figure 41B:
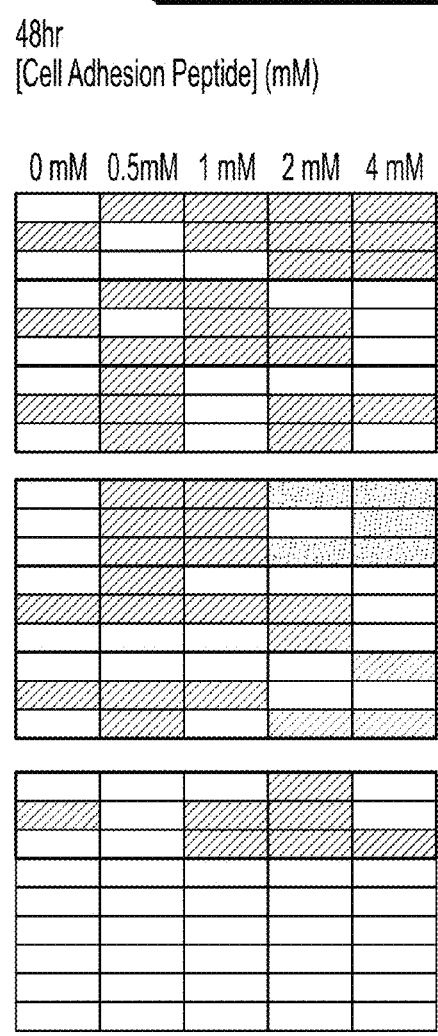

PEG was combined with 0, 1 or 2× molar excess of CRGDS (SEQ ID NO:2) and 0.05% IRGACURE 2959 photoinitiator in phosphate buffered saline. The solutions were reacted with UV light (4.5 mW/cm$^2$, 365 nm, 3 minutes) and dialyzed in de-ionized water. The product was lyophilized and dissolved in $CDCl_3$ for NMR analysis. As shown in FIGS. 36A-36C, coupling efficiency of pendant peptides to PEG can be observed by calculating NMR peak reduction at 5.8-6.2 ppm area compared to non-reacted PEGNB. Further, signal reduction increased proportionally with molar excess peptide.

Example 16

In this Example, hydrogel arrays were formed using various concentrations of PEG and/or various concentrations of crosslinking molecules and analyzed for shear modulus.

Hydrogel solutions were created by combining 20 to 100 mg/mL 20 kDa 8-arm norbornene-functionalized PEG with 0.27 mM VEGF binding peptide or scrambled equivalent, 3.4 kDa dithiolated PEG crosslinking molecule or KCGG-PQGIWGQCGK (SEQ ID NO:27) crosslinking peptide at a 1-4× molar excess concentration to PEG and 0.05% IRGACURE 2959 photoinitiator in phosphate buffered saline. The solutions were polymerized into hydrogels under UV light (365 nm). After 24 hours swelling in phosphate buffered saline, the samples were cut to 8 mm diameter discs and tested for shear modulus under a parallel plate rheometer. As shown in FIGS. 37A-37D, shear modulus increased with PEG concentration and increased crosslinking density.

Example 17

In this Example, PEG-hydrogel surfaces were analyzed to determine ability to support tubule network formation by HUVECs and IPSC-derived endothelial cells at 24 hours and 48 hours post-seeding when hydrogels present either CRGDS (SEQ ID NO:2) or cyclic RGD adhesion peptides and 0-10 ng/mL VEGF is added to endothelial growth media.

Hydrogel precursor solutions were prepared by combining 40, 50 or 70 mg/mL 20 kDa 8-arm norbornene-functionalized PEG with either 0 to 1 mM cyclic RGD{Fd}C (SEQ ID NO:33) adhesion peptide or 0 to 4 mM CRGDS (SEQ ID NO:2) adhesion peptide, additional CRDGS (SEQ ID NO:32) scrambled adhesion peptide to maintain a total adhesion peptide concentration of 1 or 4 mM respectively, KCGGPQGIWGQCGK (SEQ ID NO:27) crosslinking peptide at molar excess concentrations of 2× to PEG, and 0.05% IRGACURE 2959 photoinitiator in phosphate buffered saline. The solutions were polymerized into hydrogels under UV light (4.5 mW/cm$^2$, 365 nm, 4 minutes). Either HUVECs or IPSC-derived ECs were seeded at a density of $8.5 \times 10^4$ cells/cm$^2$ on hydrogel arrays and incubated in either Media 199 supplemented with EGM2 growth supplement (HUVECS) or VASCULIFE basal medium supplemented with endothelial growth supplement from CDI (IPSC-derived ECs). In certain conditions 5 or 10 ng/mL VEGF was supplemented into the media. The cells were photographed 24 and 48 hours after seeding and tubulogenesis was scored as non-adhesion, low cell adhesion, monolayer formation, and network formation. Results are shown in FIGS. 38-41.

What is claimed is:

1. A method of screening for pro-tubulogenic agents and anti-tubulogenic agents, the method comprising:
preparing a hydrogel composition, wherein the hydrogel composition comprises an 8-arm, 20 kDa polyethylene glycol functionalized with norbornene, a crosslinking peptide, a cell adhesion peptide, and a soluble factor binder peptide;
providing an agent suspected of promoting or reducing tubulogenesis;
contacting a cell with the hydrogel composition and agent; and
analyzing the cell.

2. The method of claim 1 wherein the agent is coupled to the hydrogel composition.

3. The method of claim 1 wherein the agent is contained within a cell culture medium, and wherein the cell culture medium is contacted with the hydrogel composition.

4. The method of claim 1 wherein the cell adhesion peptide is selected from the group consisting of CRGDS (SEQ ID NO: 2), acetylated-GCYGRGDSPG (SEQ ID NO:31), cyclic RGD{Fd}C (SEQ ID NO:33), CRGD-(G)$_{13}$-PHSRN (SEQ ID NO:29), CPHSRN-(SG)$_5$-RGD (SEQ ID NO:30), RKRLQVQLSIRT (SEQ ID NO:37), IKVAV (SEQ ID NO:38), YIGSR (SEQ ID NO:39), KRTGQYKL (SEQ ID NO:40), TYRSRKY (SEQ ID NO:41), KRTGQYKLGSKTGPGQK (SEQ ID NO:42), QAKHKQRKRLKSSC (SEQ ID NO:43), and SPKHHSQRARKKKNKNC (SEQ ID NO:44).

5. The method of claim 1 wherein the crosslinking peptide comprises an amino acid sequence selected from the group consisting of KCGGPQGIWGQGCK (SEQ ID NO:27) and KCGGPQGIAGQGCK (SEQ ID NO:28).

6. The method of claim 1 wherein the soluble factor binder comprises an amino acid sequence selected from the group consisting of SEQ ID NOs:22-26.

7. The method of claim 1 wherein the cell is selected from the group consisting of an embryonic stem cell, an embryonic stem cell-derived neuron, an embryonic stem cell-derived neural progenitor cell, an embryonic stem cell-derived astrocyte, an embryonic stem cell-derived microglial cell, an embryonic stem cell-derived endothelial cell, an embryonic stem cell-derived retinal pigment epithelial cell, an induced pluripotent stem cell, an induced pluripotent stem cell-derived neural progenitor cell, an induced pluripotent stem cell-derived astrocyte, an induced pluripotent stem cell-derived microglial cell, an induced pluripotent stem cell-derived endothelial cell, an induced pluripotent stem cell-derived retinal pigment epithelial cell, a mesenchymal stem cell, an umbilical vein endothelial cell, an NIH 3T3 fibroblast, a dermal fibroblast, a fibrosarcoma cell, a valvular interstitial cell, a cardiomyocyte, an induced pluripotent stem cell-derived cardiomyocyte, an endothelial progenitor cell, a circulating angiogenic cell, a neuron, a pericyte, a cancer cell, a hepatocyte, a pancreatic beta cell, a pancreatic islet cell and combinations thereof.

8. A method of promoting tubulogenesis, the method comprising:
preparing a hydrogel composition, wherein the hydrogel composition comprises an 8-arm, 20 kDa polyethylene glycol functionalized with norbornene, a crosslinking peptide, a cell adhesion peptide, and a soluble factor binder peptide;
providing a culture media in contact with the hydrogel composition;
contacting a cell in the culture media in contact with the hydrogel composition; and
analyzing the cell.

9. The method of claim 8 wherein the cell adhesion peptide is selected from the group consisting of CRGDS (SEQ ID NO: 2), acetylated-GCYGRGDSPG (SEQ ID NO:31), cyclic RGD{Fd}C (SEQ ID NO:33), CRGD-(G)$_{13}$-PHSRN (SEQ ID NO:29), CPHSRN-(SG)$_5$-RGD (SEQ ID NO:30), RKRLQVQLSIRT (SEQ ID NO:37), IKVAV (SEQ ID NO:38), YIGSR (SEQ ID NO:39), KRTGQYKL (SEQ ID NO:40), TYRSRKY (SEQ ID NO:41), KRTGQYKLGSKTGPGQK (SEQ ID NO:42), QAKHKQRKRLKSSC (SEQ ID NO:43), and SPKHHSQRARKKKNKNC (SEQ ID NO:44).

10. The method of claim 8 wherein the crosslinking peptide comprises an amino acid sequence selected from the group consisting of KCGGPQGIWGQGCK (SEQ ID NO:27) and KCGGPQGIAGQGCK (SEQ ID NO:28).

11. The method of claim 8 wherein the soluble factor binder comprises an amino acid sequence selected from the group consisting of SEQ ID NOs:22-26.

12. The method of claim 8 wherein the cell is selected from the group consisting of an embryonic stem cell, an embryonic stem cell-derived neuron, an embryonic stem cell-derived neural progenitor cell, an embryonic stem cell-derived astrocyte, an embryonic stem cell-derived microglial cell, an embryonic stem cell-derived endothelial cell, an embryonic stem cell-derived retinal pigment epithelial cell, an induced pluripotent stem cell, an induced pluripotent stem cell-derived neural progenitor cell, an induced pluripotent stem cell-derived astrocyte, an induced pluripotent stem cell-derived microglial cell, an induced pluripotent stem cell-derived endothelial cell, an induced pluripotent stem cell-derived retinal pigment epithelial cell, a mesenchymal stem cell, an umbilical vein endothelial cell, an NIH 3T3 fibroblast, a dermal fibroblast, a fibrosarcoma cell, a valvular interstitial cell, a cardiomyocyte, an induced pluripotent stem cell-derived cardiomyocyte, an endothelial progenitor cell, a circulating angiogenic cell, a neuron, a pericyte, a cancer cell, a hepatocyte, a pancreatic beta cell, a pancreatic islet cell and combinations thereof.

13. The method of claim 8 wherein the tubulogenesis comprises endothelial cell tubule network formation.

14. A hydrogel composition comprising an 8-arm, 20 kDa polyethylene glycol functionalized with norbornene, a crosslinking peptide, a cell adhesion peptide and a soluble factor binder peptide.

15. The hydrogel composition of claim 14 wherein the cell adhesion peptide is selected from the group consisting of CRGDS (SEQ ID NO: 2), CRGD-(G)$_{13}$-PHSRN (SEQ ID NO:29), and CPHSRN-(SG)$_5$-RGD (SEQ ID NO:30), Acetylated-GCYGRGDSPG (SEQ ID NO:31), CRDGS (SEQ ID NO:32), cyclic RGD{Fd}C (SEQ ID NO:33), RKRLQVQLSIRT (SEQ ID NO:37), IKVAV (SEQ ID NO:38), YIGSR (SEQ ID NO:39), KRTGQYKL (SEQ ID NO:40), TYRSRKY (SEQ ID NO:41), KRTGQYKLGSKTGPGQK (SEQ ID NO:42), QAKHKQRKRLKSSC (SEQ ID NO:43), and SPKHHSQRARKKKNKNC (SEQ ID NO:44).

16. The hydrogel composition of claim 14 wherein the soluble factor binder comprises an amino acid sequence selected from the group consisting of SEQ ID NOs:22-26.

17. The hydrogel composition of claim 14 having an elastic modulus range of from about 0.1 kPa to about 300 kPa.

18. The hydrogel composition of claim 14 wherein the concentration of polyethylene glycol is from about 36 mg/mL to about 70 mg/mL.

19. The hydrogel composition of claim 14 comprising an extent of crosslinking, wherein the extent of crosslinking is from about 30% to about 70%.

* * * * *